US011149019B2

(12) United States Patent
Kim et al.

(10) Patent No.: US 11,149,019 B2
(45) Date of Patent: Oct. 19, 2021

(54) PHENYLPYRIDINE DERIVATIVE AND PHARMACEUTICAL COMPOSITION COMPRISING THE SAME

(71) Applicant: Daewoong Pharmaceutical Co., Ltd., Gyeonggi-do (KR)

(72) Inventors: Wol-Young Kim, Gyeonggi-do (KR); Jung-eun Park, Gyeonggi-do (KR); Keuk-Chan Bang, Gyeonggi-do (KR); Joon-Seok Park, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/650,441

(22) PCT Filed: Oct. 11, 2018

(86) PCT No.: PCT/KR2018/011913
§ 371 (c)(1),
(2) Date: Mar. 25, 2020

(87) PCT Pub. No.: WO2019/074275
PCT Pub. Date: Apr. 18, 2019

(65) Prior Publication Data
US 2020/0223821 A1 Jul. 16, 2020

(30) Foreign Application Priority Data
Oct. 11, 2017 (KR) .................. 10-2017-0131349

(51) Int. Cl.
| C07D 401/12 | (2006.01) |
| C07D 401/14 | (2006.01) |
| C07D 413/14 | (2006.01) |
| C07D 417/12 | (2006.01) |
| C07D 417/14 | (2006.01) |

(52) U.S. Cl.
CPC ......... *C07D 401/12* (2013.01); *C07D 401/14* (2013.01); *C07D 413/14* (2013.01); *C07D 417/12* (2013.01); *C07D 417/14* (2013.01)

(58) Field of Classification Search
CPC .. C07D 401/12; C07D 401/14; C07D 413/14; C07D 417/12; C07D 417/14
See application file for complete search history.

(56) References Cited

U.S. PATENT DOCUMENTS

| 2008/0139557 A1 | 6/2008 | Blomgren et al. |
| 2010/0222325 A1 | 9/2010 | Berthel et al. |
| 2011/0059944 A1 | 3/2011 | Blomgren et al. |
| 2012/0082702 A1 | 4/2012 | DeLucca et al. |
| 2015/0175601 A1 | 6/2015 | Qian et al. |
| 2016/0228432 A1 | 8/2016 | Crawford et al. |
| 2016/0324878 A1 | 11/2016 | He |
| 2017/0050936 A1 | 2/2017 | Qian et al. |
| 2017/0196881 A1 | 7/2017 | Qian et al. |
| 2018/0125855 A1 | 5/2018 | Qian et al. |

FOREIGN PATENT DOCUMENTS

| CL | 200602024 | | 8/2006 |
| CL | 2007002640 | A1 | 6/2008 |
| CL | 2011002115 | | 3/2012 |
| EA | 201490858 | A1 | 8/2014 |
| JP | 2012-529535 | A | 11/2012 |
| KR | 2016-0090786 | A | 8/2016 |
| RU | 2470923 | C2 | 12/2012 |
| WO | WO-2002/50071 | A1 | 6/2002 |
| WO | WO-2005/056785 | A2 | 6/2005 |
| WO | WO-2005/066335 | A1 | 7/2005 |
| WO | WO-2007/017169 | A1 | 2/2007 |
| WO | WO-2008/039218 | A2 | 4/2008 |
| WO | WO-2008/154026 | A1 | 12/2008 |
| WO | WO-2010-009342 | A2 | 1/2010 |
| WO | 2012-035055 | * | 3/2012 |
| WO | WO-2012/035055 | A1 | 3/2012 |
| WO | WO-2012/041476 | A1 | 4/2012 |
| WO | WO-2014/036016 | A1 | 3/2014 |
| WO | WO-2014/055934 | A2 | 4/2014 |
| WO | WO-2015/061247 | A2 | 4/2015 |
| WO | WO-2015/151006 | A1 | 10/2015 |
| WO | WO-2015/157556 | A1 | 10/2015 |

OTHER PUBLICATIONS

Sahu, Gurr Top Med CHem, 2009, vol. 9(8), 690-703. (Year: 2009).*
McGee, J Leukoc Biol, vol. 109, 2021, 49-51. (Year: 2021).*
Vargas, Scandinivian J Imunology, 2013, 130-139. (Year: 2013).*
Santos-Garcia, "QSAR Analysis of Nicotinamidic Compounds and Design of Potential Bruton's Tyrosine Kinase (Btk) Inhibitors", Journal of Biomolecular Structure and Dynamics, vol. 34, No. 7, pp. 1421-1440.
Office Action in JP Application No. 2020-519093 dated Dec. 22, 2020, 6 pages.
Office Action in RU Application No. 2020115083 dated Dec. 21, 2020, 12 pages.
Extended European Search Report in EP Application No. 18865651.6 dated Feb. 17, 2021, 5 pages.
Office Action in Chilean Application No. 940-2020 dated Feb. 15, 2021, 21 pages.
Doebelin et al., "Trisubstitution of Pyridine Through Sequential and Regioselective Palladium Cross-coupling Reactions Affording Analogs of Known GPR54 Antagonists", RSC Advances, Royal Society of Chemistry, vol. 3, No. 26, 2013, pp. 10296-10300.
Leipe et al., "Role of Th17 Cells in Human Autoimmune Arthritis" Arthritis and Rheumatism, vol. 62, No. 10, Oct. 2010, pp. 2876-2885.

(Continued)

*Primary Examiner* — D Margaret M Seaman
(74) *Attorney, Agent, or Firm* — Marshall, Gerstein & Borun LLP

(57) ABSTRACT

The present disclosure relates to a novel phenylpyridine derivative represented by Chemical Formula 1 and a pharmaceutical composition comprising the same, and the compound according to the present disclosure can be usefully used for the prevention or treatment of autoimmune diseases or cancers.

13 Claims, No Drawings

(56) References Cited

OTHER PUBLICATIONS

Sahu et al., "ITK Inhibitors in Inflammation and Immune-Mediated Disorders" Current Topics in Medicinal Chemistry, 9, 2009, pp. 690-703.
Ho Yin Lo, "Itk Inhibitors: a Patent Review", Expert Opin. Ther, Patents, vol. 20, 2010, pp. 459-469.
Fowell et al., "Impaired NFATc Translocation and Failure of Th2 Development in Itk-deficient CD4$^+$ T Cells", Immunity, vol. 11, Oct. 1999, pp. 399-409.
Horwood et al., "Bruton's Tyrosine Kinase is Required for Lipopolysaccharide-induced Tumor Necrosis Factor α Production", J. Exp. Med., vol. 197, No. 12, Jun. 16, 2003, pp. 1603-1611.
Xu et al., "Quantitative Structure-activity Relationship Study on BTK Inhibitors by Modified Multivariate Adaptive Regression Spline and CoMSIA Methods", SAR and QSAR in Environmental Research, vol. 26, No. 4, 2015, pp. 279-300.
Liang et al., "Structure-Activity Relationship Study of QL47: A Broad-Spectrum Antiviral Agent", ACS Medicinal Chemistry Letters, 8, 2017, pp. 344-349.
Schaeffer et al., "Mutation of Tec Family Kinases Alters T Helper Cell Differentiation", http://immunol.nature.com, vol. 2, No. 12, Dec. 2001, pp. 1183-1188.
Iwaki et al., "Btk Plays a Crucial Role in the Amplification of FcεRI-mediated Mast Cell Activation by Kit", The Journal of Biological Chemistry, vol. 280, No. 48, Dec. 2, 2005, pp. 40261-40270.
Zhong et al., "Targeting Interleukin-2-inducible T-cell Kinase (ITK) and Resting Lymphocyte Kinase (RLK) Using a Novel Covalent Inhibitor PRN694", The Journal of Biological Chemistry, vol. 290, No. 10, Mar. 6, 2015, pp. 5960-5978.
Gomez-Rodriguez, "Itk-mediated Integration of T Cell Receptor and Cytokine Signaling Regulates the Balance Between Th17 and Regulatory T Cells", The Journal of Experimental Medicine, vol. 211, No. 3, 2014, pp. 529-543.
Search Report and Written Opinion in International Application No. PCT/KR2018/011913 dated Jan. 17, 2019, 9 pages (partial translation of search report).

\* cited by examiner

PHENYLPYRIDINE DERIVATIVE AND PHARMACEUTICAL COMPOSITION COMPRISING THE SAME

TECHNICAL FIELD

The present disclosure relates to a novel phenylpyridine derivative useful as BTK (Bruton's Tyrosince Kinase) inhibitor and a pharmaceutical composition comprising the same.

BACKGROUND ART

BTK (Bruton's Tyrosince Kinase) and ITK (Interleukin-2 Tyrosine Kinase), are a type of tyrosine kinase, together with Tec (tyrosine kinase expressed in hepatocellular carcinoma), RLK (Resting Lymphocyte Kinase) and BMX (Bone-Marrow tyrosine kinase gene on chromosome X), which does not have a receptor and acts on various immune responses.

BTK acts as a regulator of early B-cell development as well as of mature B-cell activation, signaling and survival. The B-cell is signaled by a B cell receptor (BCR) that recognizes an antigen attached to the surface of an antigen-resenting cell and is activated into a mature antibody-producing cell. However, aberrant signaling via BCR leads to abnormal B-cell proliferation and the formation of pathologic autoantibodies, and thereby can induce cancer, autoimmune and/or inflammatory diseases. Thus, in the abnormal B-cell proliferation, signaling via BCR may be blocked when BTK is deficient. Thus, inhibition of BTK can block B-cell mediated disease processes, and the use of BTK inhibitors may be a useful approach for the treatment of B-cell mediated diseases.

Furthermore, BTK can be expressed by other cells that may be associated with disease besides B-cells. For example, BTK is important components for Fc-gamma signaling in bone marrow cells, and is expressed by mast cells. Specifically, BTK-deficient bone marrow-induced mast cells exhibit impaired antigen-induced degranulation, and inhibition of BTK activity is known to be useful for treating pathological mast cell responses such as allergy and asthma (Iwaki et al. J. Biol Chem. 2005 280: 40261). In addition, it is known that monocytes from XLA patients, in which BTK activity is absent, decreases in TNF alpha production following stimulation and thus TNF alpha-mediated inflammation could be inhibited by BTF inhibitors (see, Horwood et al., J. Exp. Med. 197: 1603, 2003).

ITK is expressed not only in T cells but also in NK cells and mast cells, and plays an important role in T-cell proliferation and production of important cytokines such as IL-2, IL-4, IL-5, IL-10, IL-13 and IL-17 (Schaeffer et al. Nat. Immune 2001, 2, 1183; Fowell et al. Immunity, 1999, 11, 399). T cells are activated by TCR signaling, and the activated T cells produce inflammatory cytokine and activate B cells and macrophages, causing autoimmune diseases such as RA (Sahu N. et al. Curr Top Med Chem. 2009, 9, 690). Previously, it was known that T cells are activated by Th1 cells to induce RA diseases, but recently, it has been reported that not only Th17/Treg but also Th1 cells act as a pathogenesis of RA (J Leipe J. et al. Arthritis Rheum. 2010, 62, 2876). In addition, the ITK has been previously developed as an immunotherapeutic drug target such as asthma, but no ITK has been developed as a therapeutic for RA (Lo H. Y Expert Opin Ther Pat. 2010, 20, 459). Recently, however, it has been reported to regulate the development of Th17 and Treg cells via ITK−/−mice, and it has ample potential as a therapeutic target for RA (Gomez-Rodriguez J. et al. J. Exp. Med. 2014, 211, 529).

In a study using the ITK inhibitor PRN694, a study on the reduction of TNF-alpha which is a typical inflammatory cytokine of RA diseases, has been reported, confirming the possibility of development as a therapeutic agent for RA by regulating Th17 expression through ITK inhibition (Zhong Y. ey al. THE JOURNAL OF BIOLOGICAL CHEMISTRY 2015, 290, 5960).

At present, there has been no case where it has been developed as a substance that dually inhibits BTK and ITK. As the BTK inhibitor, WO 2008/039218 discloses 4-aminopyrazolo[3,4-d]pyrimidinylpiperidine derivatives, and WO2015/061247 discloses hetero compounds such as pyridine, pyrimidine, pyrazine and pyridazine, and WO2014/055934 discloses pyrimidinyl phenyl acrylamide derivatives. As the ITK inhibitor, WO2005/066335 discloses aminobenzimidazoles, WO2005/056785 discloses pyridones, WO2002/050071 discloses aminothiazole derivatives, and recently, WO2014/036016 discloses benzimidazole derivatives.

In view of the above, as a result of studying novel compounds, the present inventors has found that a compound having a chemical structure different from BTK inhibitors reported so far has excellent BTK and ITK dual-activity inhibitory effect, thereby completing the present disclosure. The compounds belonging to the present disclosure mainly have BTK and ITK inhibitory activity on their own, but do not exclude a possibility of exhibiting a pharmacological action as an efficacious agent by a special body environment or by products of metabolic process, after absorption into the body.

DETAILED DESCRIPTION OF THE INVENTION

Technical Problem

It is one object of the present disclosure to provide a novel phenylpyridine derivative useful as a BTK inhibitor, and a pharmaceutical composition comprising the same.

Technical Solution

In order to achieve the above objects, the present disclosure provides a compound represented by the following Chemical Formula 1, or a pharmaceutically acceptable salt thereof:

[Chemical Formula 1]

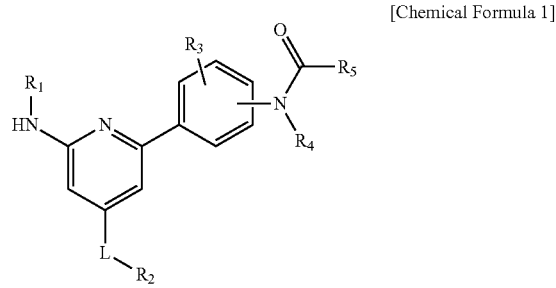

wherein, in Chemical Formula 1, $R_1$ is —CO—($C_{1-4}$ alkyl); —CO—($C_{3-6}$ cycloalkyl); —CONH—($C_{1-4}$ alkyl); or 5- or 6-membered heteroaryl including 1 to 3 heteroatoms each independently selected from the group consisting of N, O and S, with the proviso that the 5- or 6-membered heteroaryl contains at least one N, the 5- or 6-membered heteroaryl is unsubstituted or substituted with $C_{1-4}$ alkyl, $C_{1-4}$ haloalkyl, $C_{3-6}$ cycloalkyl, phenyl, phenoxyphenyl, —($C_{1-4}$ alkylene)-(phenyl unsubstituted or substituted with $C_{1-4}$ alkyl), or —CONH— (phenyl unsubstituted or substituted with $C_{1-4}$ alkyl and/or halogen), L is a bond, $C_{1-4}$ alkylene, or —CO—, $R_2$ is hydrogen; $C_{1-4}$ alkyl; $C_{1-4}$ haloalkyl; amino; NH($C_{1-10}$ alkyl); N($C_{1-10}$ alkyl)$_2$; phenyl; pyridinyl; or heterocycloalkyl selected from the group consisting of diazefanyl, morpholino, piperazinyl, piperidinyl, and pyrrolidinyl, the heterocycloalkyl is unsubstituted or substituted with $C_{1-4}$ alkyl, two $C_{1-4}$ alkyl, $C_{1-4}$ haloalkyl, $C_{3-6}$ cycloalkyl, $C_{1-4}$ alkyl substituted with $C_{1-4}$ alkoxy, $C_{1-4}$ hydroxyalkyl, —CO—($C_{1-4}$ alkyl), —CO—($C_{3-6}$ cycloalkyl), or —CONH—($C_{1-4}$ alkyl), $R_3$ is hydrogen, $C_{1-4}$ alkyl, or halogen, $R_4$ is hydrogen, or $C_{1-4}$ alkyl, and $R_5$ is $C_{2-4}$ alkenyl, or $C_{2-4}$ alkynyl.

Preferably, the 5- or 6-membered heteroaryl of $R_1$ is isoxazolyl, oxadiazolyl, pyrazolyl, pyridinyl, thiadiazolyl, or thiazolyl.

Preferably, the $R_1$ is —CO-(ethyl); —CO-(cyclopropyl); —CONH-(methyl); isoxazolyl substituted with methyl; oxadiazolyl substituted with methyl; pyrazolyl unsubstituted or substituted with methyl, ethyl, cyclopropyl, cyclopentyl, phenyl, phenoxyphenyl, methylbenzyl, 1-(methylphenyl)ethyl, or phenethyl; unsubstituted pyridinyl; thiadiazolyl unsubstituted or substituted with methyl; or thiazolyl substituted with methyl, trifluoromethyl, or —CONH— (phenyl substituted with methyl and chloro).

Preferably, L is a bond, methylene, or —CO—.

Preferably, $R_2$ is hydrogen; methyl; trifluoromethyl; dimethylamino; 3,3-dimethylbutan-2-ylamino; phenyl; pyridinyl; diazefanyl substituted with methyl; morpholino unsubstituted or substituted with two methyls; piperazinyl substituted with methyl, ethyl, propyl, isopropyl, 2,2,2-trifluoroethyl, cyclopropyl, 2-methoxyethyl, 2-hydroxyethyl, —CO-(methyl), —CO-(ethyl)-, —CO-(isopropyl), —CO-(cyclopropyl), —CONH-(methyl), —CONH-(ethyl)-, or —CO-(isopropyl); unsubstituted piperidinyl; or unsubstituted pyrrolodinyl.

Preferably, $R_3$ is hydrogen, methyl, fluoro, or chloro.

Preferably, $R_4$ is hydrogen, methyl, or ethyl.

Preferably, $R_5$ is —CH=CH$_2$, —CH=CHCH$_3$, or —C≡CH.

Preferably, Chemical Formula 1 is represented by the following Formula 1-1:

[Chemical Formula 1-1]

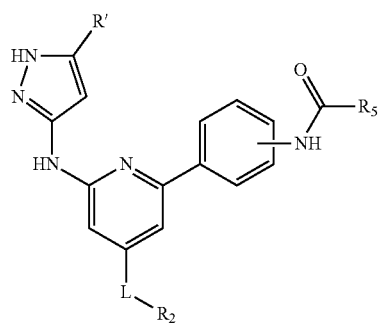

wherein, in Chemical Formula 1-1,

R' is hydrogen, $C_{1-4}$ alkyl, $C_{3-6}$ cycloalkyl, phenyl, phenoxyphenyl, —($C_{1-4}$ alkylene)-(phenyl unsubstituted or substituted with $C_{1-4}$ alkyl), or —CONH-(phenyl unsubstituted or substituted with $C_{1-4}$ alkyl and/or halogen), L is a bond, $C_{1-4}$ alkylene, or —CO—, $R_2$ is hydrogen; $C_{1-4}$ alkyl; $C_{1-4}$ haloalkyl; amino; NH($C_{1-10}$ alkyl); N($C_{1-10}$ alkyl)2; phenyl; pyridinyl; morpholino; or piperidinyl, and $R_5$ is $C_{2-4}$ alkenyl, or $C_{2-4}$ alkynyl.

Preferably, Chemical Formula 1 is represented by the following Chemical Formula 1-2:

[Chemical Formula 1-2]

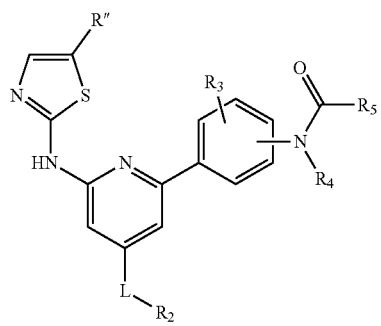

wherein, in Chemical Formula 1-2,

R'' is $C_{1-4}$ alkyl, $C_{1-4}$ haloalkyl, or —CONH-(phenyl unsubstituted or substituted with $C_{1-4}$ alkyl and/or halogen), L is a bond, $C_{1-4}$ alkylene, or —CO—, $R_2$ is $C_{1-4}$ alkyl; amino; NH($C_{1-10}$ alkyl); N($C_{1-10}$ alkyl)$_2$; pyridinyl; or heterocycloalkyl selected from the group consisting of diazefanyl, morpholino, piperazinyl, and pyrrolodinyl, the heterocycloalkyl is unsubstituted or substituted with $C_{1-4}$ alkyl, two $C_{1-4}$ alkyls, $C_{1-4}$ haloalkyl, $C_{3-6}$ cycloalkyl, $C_{1-4}$ alkyl substituted with $C_{1-4}$ alkoxy, $C_{1-4}$ hydroxyalkyl, —CO—($C_{1-4}$ alkyl), —CO—($C_{3-6}$ cycloalkyl), or —CONH—($C_{1-4}$ alkyl), $R_3$ is hydrogen, $C_{1-4}$ alkyl, or halogen, $R_4$ is hydrogen or $C_{1-4}$ alkyl, and $R_5$ is $C_{2-4}$ alkenyl, or $C_{2-4}$ alkynyl.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

As the free acid, an organic acid and an inorganic acid can be used. Examples of the inorganic acids include hydrochloric acid, phosphoric acid, sulfuric acid, nitric acid, tartaric acid and the like. Examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto. Preferably, the salt may be a hydrochloride salt.

In addition, a pharmaceutically acceptable metal salt can be obtained by a conventional method using a base. For example, a compound represented by Chemical Formula 1 is dissolved in an excessive amount of an alkali metal hydroxide or an alkaline earth metal hydroxide solution, the non-soluble salt is filtered, and the filtrate is evaporated and dried to obtain a pharmaceutically acceptable metal salt. At this time, it is particularly preferable to prepare a sodium salt, a potassium salt or a calcium salt as the metal salt.

A pharmaceutically unacceptable salt or solvate of the compound of Chemical Formula 1 may be used as an intermediate when preparing the compound of Chemical Formula 1, or the pharmaceutically acceptable salt or the solvate thereof.

The compound of Chemical Formula 1 according to the present invention includes not only pharmaceutically acceptable salts thereof, but also solvates such as hydrates that can be prepared therefrom, and includes all possible stereoisomers, but are not limited thereto. The solvate and the stereoisomer of the compound of Chemical Formula 1 may be prepared from the compound of Chemical Formula 1 using common methods known in the art.

In addition, the compound of Chemical Formula 1 according to the present invention may be prepared either in a crystalline form or in a non-crystalline form, and when the compound of Chemical Formula 1 is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

Representative examples of the compound represented by Chemical Formula 1 or a pharmaceutically acceptable salt thereof are as follows:

1) N-(4-(4-benzyl-6-(5-methyl-1H-pyrazol-3-ylamino)pyridin-2-yl)phenyl)acrylamide,
2) N-(3-(4-benzyl-6-(5-methyl-1H-pyrazol-3-ylamino)pyridin-2-yl)phenyl)acrylamide,
3) N-(4-(4-benzyl-6-(5-methyl-1H-pyrazol-3-ylamino)pyridin-2-yl)phenyl)propiolamide,
4) N-(3-(4-benzyl-6-(5-cyclopentyl-1H-pyrazol-3-ylamino)pyridin-2-yl)phenyl)acrylamide,
5) N-(3-(4-benzyl-6-(5-phenyl-1H-pyrazol-3-ylamino)pyridin-2-yl)phenyl)acrylamide,
6) N-(3-(4-benzyl-6-(5-methyl-1H-pyrazol-3-ylamino)pyridin-2-yl)phenyl)propiolamide,
7) N-(3-(4-benzyl-6-(5-(4-phenoxyphenyl)-1H-pyrazol-3-ylamino)pyridin-2-yl)phenyl)acrylamide,
8) N-(3-(4-benzyl-6-(5-(4-methylbenzyl)-1H-pyrazol-3-ylamino)pyridin-2-yl)phenyl)acrylamide,
9) N-(3-(4-benzyl-6-((5-(1-p-tolylethyl)-1H-pyrazol-3-yl)amino)pyridin-2-yl)phenyl)acrylamide,
10) N-(3-(4-benzyl-6-(5-phenethyl-1H-pyrazol-3-ylamino)pyridin-2-yl)phenyl)acrylamide,
11) N-(3-(6-(1H-pyrazol-3-ylamino)-4-benzylpyridin-2-yl)phenyl)acrylamide,
12) N-(3-(6-(5-methyl-1H-pyrazol-3-ylamino)pyridin-2-yl)phenyl)acrylamide,
13) N-(3-(6-(5-cyclopentyl-1H-pyrazol-3-ylamino)pyridin-2-yl)phenyl)acrylamide,
14) N-(3-(6-(5-phenyl-1H-pyrazol-3-ylamino)pyridin-2-yl)phenyl)acrylamide,
15) N-(3-(6-(1H-pyrazol-3-ylamino)pyridin-2-yl)phenyl)acrylamide,
16) N-(3-(4-methyl-6-(5-methyl-1H-pyrazol-3-ylamino)pyridin-2-yl)phenyl)acrylamide,
17) N-(3-(6-(5-methyl-1H-pyrazol-3-ylamino)-4-(trifluoromethyl)pyridin-2-yl)phenyl)acrylamide,
18) N-(3-(4-methyl-6-(pyridin-2-ylamino)pyridin-2-yl)phenyl)acrylamide,
19) N-(3-(4-(((3,3-dimethylbutan-2-ylamino)methyl)-6-(5-methyl-1H-pyrazol-3-ylamino)pyridin-2-yl)phenyl)acrylamide,
20) 2-(3-acrylamidophenyl)-N-(3,3-dimethylbutan-2-yl)-6-(5-methyl-1H-pyrazol-3-ylamino)isonicotinamide,
21) 2-(3-acrylamidophenyl)-N,N-dimethyl-6-(5-methyl-1H-pyrazol-3-ylamino)isonicotinamide,
22) N-(3-(6-(5-methyl-1H-pyrazol-3-ylamino)-4-(morpholinomethyl)pyridin-2-yl)phenyl)acrylamide,
23) N-(3-(6-(5-methyl-1H-pyrazol-3-ylamino)-4-phenylpyridin-2-yl)phenyl)acrylamide,
24) N-(3-(6-(5-ethyl-1H-pyrazol-3-ylamino)-4-methylpyridin-2-yl)phenyl)acrylamide,
25) N-(3-(6-(5-cyclopropyl-1H-pyrazol-3-ylamino)-4-methylpyridin-2-yl)phenyl)acrylamide,
26) N-(3-(4-methyl-6-(5-methylthiazol-2-ylamino)pyridin-2-yl)phenyl)acrylamide,
27) N-(3-(6-(5-cyclopropyl-1H-pyrazol-3-ylamino)-4-(morpholinomethyl)pyridin-2-yl)phenyl)acrylamide,
28) N-(3-(6-(5-cyclopropyl-1H-pyrazol-3-ylamino)-4-(morpholine-4-carbonyl)pyridin-2-yl)phenyl)acrylamide,
29) N-(3-(6-(5-methylthiazol-2-ylamino)-4-(morpholine-4-carbonyl)pyridin-2-yl)phenyl)acrylamide,
30) N-(3-(6-(5-methylthiazol-2-ylamino)-4-(morpholinomethyl)pyridin-2-yl)phenyl)acrylamide,
31) N-(3-(6-(5-methyl-1H-pyrazol-3-ylamino)-4-(morpholine-4-carbonyl)pyridin-2-yl)phenyl)acrylamide,
32) N-(3-(6-(5-methyl-1H-pyrazol-3-ylamino)-4-(piperidin-1-ylmethyl)pyridin-2-yl)phenyl)acrylamide,
33) 2-(6-(3-acrylamidophenyl)-4-(morpholinomethyl)pyridin-2-ylamino)-N-(2-chloro-6-methylphenyl)thiazole-5-carboxamide,
34) N-(3-(4-((2,6-dimethylmorpholino)methyl)-6-(5-methylthiazol-2-ylamino)pyridin-2-yl)phenyl)acrylamide,
35) N-(3-(4-(dimethylamino)-6-(5-methylthiazol-2-ylamino)pyridin-2-yl)phenyl)acrylamide,
36) N-(3-(6-(5-methylthiazol-2-ylamino)-4-morpholinopyridin-2-yl)phenyl)acrylamide,
37) N-(3-(4-((4-methylpiperazin-1-yl)methyl)-6-(5-methylthiazol-2-ylamino)pyridin-2-yl)phenyl)acrylamide,
38) (E)-N-(3-(4-benzyl-6-(5-methyl-1H-pyrazol-3-ylamino)pyridin-2-yl)phenyl)but-2-enamide,
39) N-(3-(6-(5-methyl-1,3,4-thiadiazol-2-ylamino)-4-(morpholinomethyl)pyridin-2-yl)phenyl)acrylamide,
40) N-(3-(6-(5-methylisoxazol-3-ylamino)-4-(morpholinomethyl)pyridin-2-yl)phenyl)acrylamide,
41) N-(3-(6-(5-methyl-1,3,4-oxadiazol-2-ylamino)-4-(morpholinomethyl)pyridin-2-yl)phenyl)acrylamide,
42) N-(6-(3-acrylamidophenyl)-4-(morpholinomethyl)pyridin-2-yl)cyclopropanecarboxamide,
43) N-(3-(4-((4-(2-hydroxyethyl)piperazin-1-yl)methyl)-6-(5-methylthiazol-2-ylamino)pyridin-2-yl)phenyl)acrylamide,
44) N-(3-(6-(1,2,4-thiadiazol-5-ylamino)-4-(morpholinomethyl)pyridin-2-yl)phenyl)acrylamide,
45) N-(3-(4-((4-cyclopropylpiperazin-1-yl)methyl)-6-(5-methylthiazol-2-ylamino)pyridin-2-yl)phenyl)acrylamide,
46) N-(3-(4-(((2S,6R)-2,6-dimethylmorpholino)methyl)-6-(5-methylthiazol-2-ylamino)pyridin-2-yl)phenyl)acrylamide, 47) N-(3-(6-(5-methylthiazol-2-ylamino)-4-(pyrrolidin-1-ylmethyl)pyridin-2-yl)phenyl)acrylamide,
48) N-(3-(6-(5-methylthiazol-2-ylamino)-4-((4-propylpiperazin-1-yl)methyl)pyridin-2-yl)phenyl)acrylamide,
49) N-(3-(4-((4-(2-methoxyethyl)piperazin-1-yl)methyl)-6-(5-methylthiazol-2-ylamino)pyridin-2-yl)phenyl)acrylamide,
50) N-(3-(6-(5-methylthiazol-2-ylamino)-4-((4-(2,2,2-trifluoroethyl)piperazin-1-yl)methyl)pyridin-2-yl)phenyl)acrylamide,
51) N-(3-(4-(morpholinomethyl)-6-(5-(trifluoromethyl)thiazol-2-ylamino)pyridin-2-yl)phenyl)acrylamide,
52) N-(4-fluoro-3-(6-(5-methylthiazol-2-ylamino)-4-(morpholinomethyl)pyridin-2-yl)phenyl)acrylamide,
53) N-(3-(4-((4-ethylpiperazin-1-yl)methyl)-6-(5-methylthiazol-2-ylamino)pyridin-2-yl)phenyl)acrylamide,
54) N-(3-(4-((4-isopropylpiperazin-1-yl)methyl)-6-(5-methylthiazol-2-ylamino)pyridin-2-yl)phenyl)acrylamide,
55) N-(3-(4-((4-methyl-1,4-diazepan-1-yl)methyl)-6-(5-methylthiazol-2-ylamino)pyridin-2-yl)phenyl)acrylamide,
56) N-(2-fluoro-5-(6-(5-methylthiazol-2-ylamino)-4-(morpholinomethyl)pyridin-2-yl)phenyl)acrylamide,
57) N-(3-fluoro-5-(6-(5-methylthiazol-2-ylamino)-4-(morpholinomethyl)pyridin-2-yl)phenyl)acrylamide,
58) N-(2-methyl-5-(6-(5-methylthiazol-2-ylamino)-4-(morpholinomethyl)pyridin-2-yl)phenyl)acrylamide,
59) N-(4-methyl-3-(6-(5-methylthiazol-2-ylamino)-4-(morpholinomethyl)pyridin-2-yl)phenyl)acrylamide,
60) N-(3-(4-((4-acetylpiperazin-1-yl)methyl)-6-(5-methylthiazol-2-ylamino)pyridin-2-yl)phenyl)acrylamide,
61) N-(3-(6-(5-methylthiazol-2-ylamino)-4-((4-propionylpiperazin-1-yl)methyl)pyridin-2-yl)phenyl)acrylamide,
62) N-(3-(4-((4-isobutyrylpiperazin-1-yl)methyl)-6-(5-methylthiazol-2-ylamino)pyridin-2-yl)phenyl)acrylamide,
63) N-(3-(4-((4-(cyclopropanecarbonyl)piperazin-1-yl)methyl)-6-(5-methylthiazol-2-ylamino)pyridin-2-yl)phenyl)acrylamide,
64) N-(4-chloro-3-(6-(5-methylthiazol-2-ylamino)-4-(morpholinomethyl)pyridin-2-yl)phenyl)acrylamide,
65) N-methyl-N-(3-(6-(5-methylthiazol-2-ylamino)-4-(morpholinomethyl)pyridin-2-yl)phenyl)acrylamide,
66) N-ethyl-N-(3-(6-(5-methylthiazol-2-ylamino)-4-(morpholinomethyl)pyridin-2-yl)phenyl)acrylamide,
67) N-(3-(6-(3-methylureido)-4-(morpholinomethyl)pyridin-2-yl)phenyl)acrylamide,
68) N-(3-(4-(morpholinomethyl)-6-propionamidopyridin-2-yl)phenyl)acrylamide,
69) 4-((2-(3-acrylamidophenyl)-6-(5-methylthiazol-2-ylamino)pyridin-4-yl)methyl)-N-ethylpiperazine-1-carboxamide,
70) 4-((2-(3-acrylamidophenyl)-6-(5-methylthiazol-2-ylamino)pyridin-4-yl)methyl)-N-isopropylpiperazine-1-carboxamide,
71) 4-((2-(3-acrylamidophenyl)-6-(5-methylthiazol-2-ylamino)pyridin-4-yl)methyl)-N-methylpiperazine-1-carboxamide,
72) N-(3-(6-(5-methyl-1H-pyrazol-3-ylamino)-4-(pyridin-3-ylmethyl)pyridin-2-yl)phenyl)acrylamide, and
73) N-(3-(6-(5-methylthiazol-2-ylamino)-4-(pyridin-3-ylmethyl)pyridin-2-yl)phenyl)acrylamide.

In addition, according to the present disclosure, when $R_4$ is hydrogen in the compound represented by Chemical Formula 1, the compound represented by Chemical Formula 1 may be prepared, for example, through Reaction Scheme 1 below.

[Reaction Scheme 1]

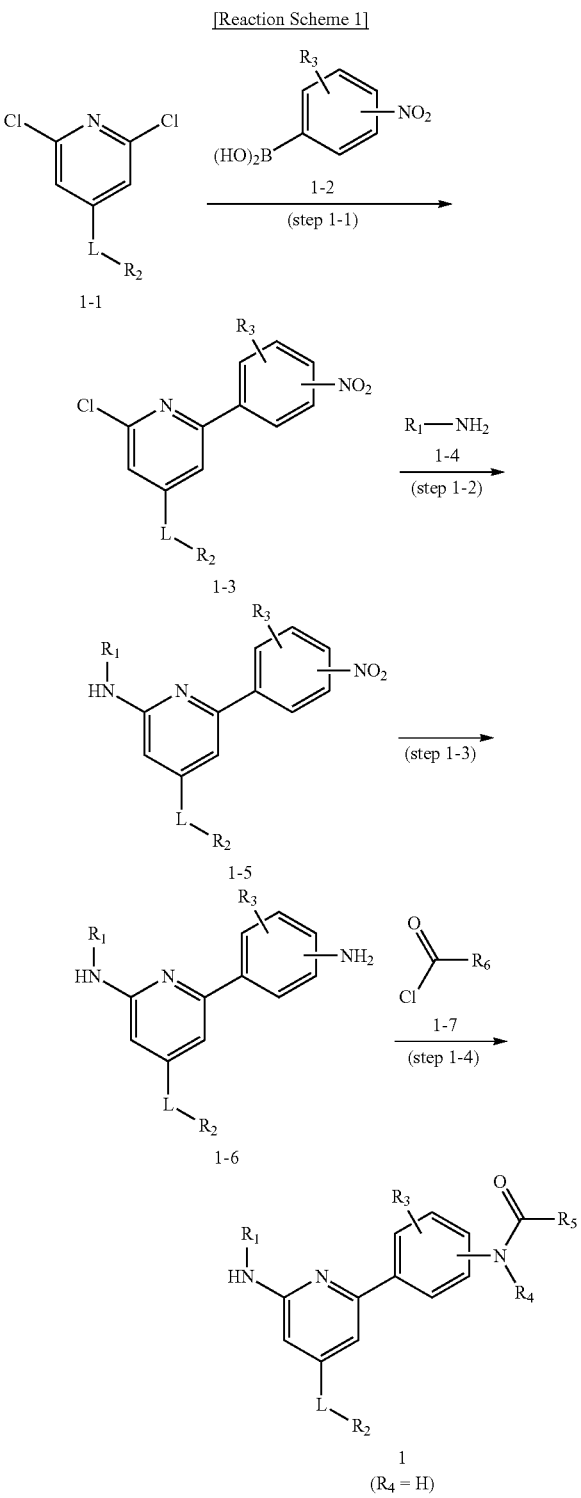

Step 1-1 is a step of reacting the compound represented by Chemical Formula 1-1 and the compound represented by Chemical Formula 1-2 to prepare a compound represented by Chemical Formula 1-3. The reaction is a Suzuki coupling reaction, which is preferably carried out in the presence of a palladium catalyst and a base.

Step 1-2 is a step of reacting the compound represented by Chemical Formula 1-3 and the compound represented by Chemical Formula 1-4 to prepare a compound represented by Chemical Formula 1-5. The reaction is an amine substitution reaction, which is preferably carried out in the presence of a palladium catalyst and a base.

Step 1-3 is a step of hydrogenating the compound represented by Chemical Formula 1-5 to prepare a compound represented by Chemical Formula 1-6. Through the hydrogenation reaction, a nitro group of the compound represented by Chemical Formula 1-5 is substituted with an amine group. The hydrogenation reaction is preferably carried out in the presence of a palladium/carbon catalyst.

Step 1-4 is a step of reacting the compound represented by Chemical Formula 1-6 with the compound represented by Chemical Formula 1-7 to prepare a compound represented by Chemical Formula 1. The reaction is an amidation reaction, which is preferably carried out in the presence of a tertiary amine.

Further, in Reaction Scheme 1, a reaction for protecting with a protecting group and a reaction for removing the protecting group depending on each substituent may be added.

According to another embodiment of the present disclosure, when $R_4$ is $C_{1-4}$ alkyl in the compound represented by Chemical Formula 1, the compound represented by Chemical Formula 1 may be prepared, for example, through Reaction Scheme 2 below.

[Reaction Scheme 2]

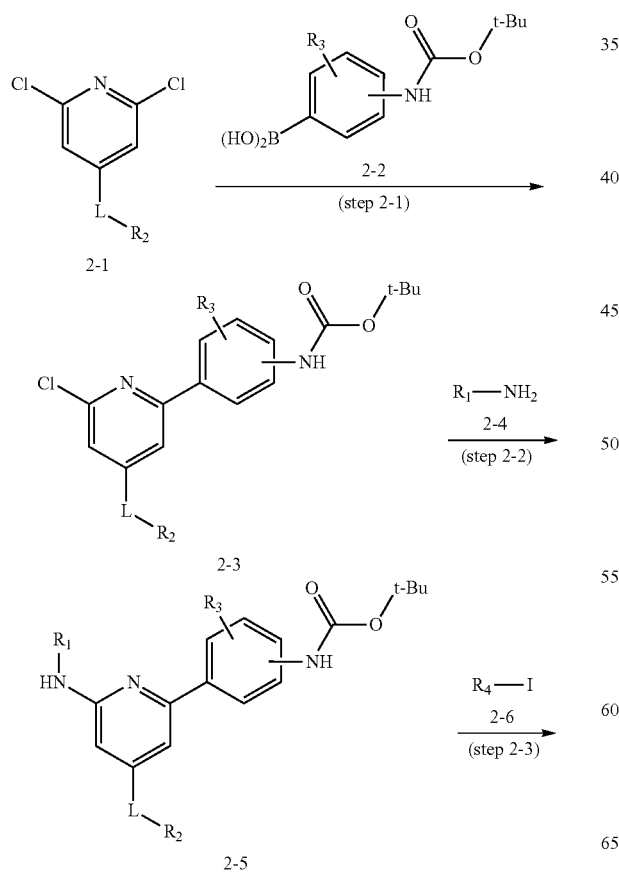

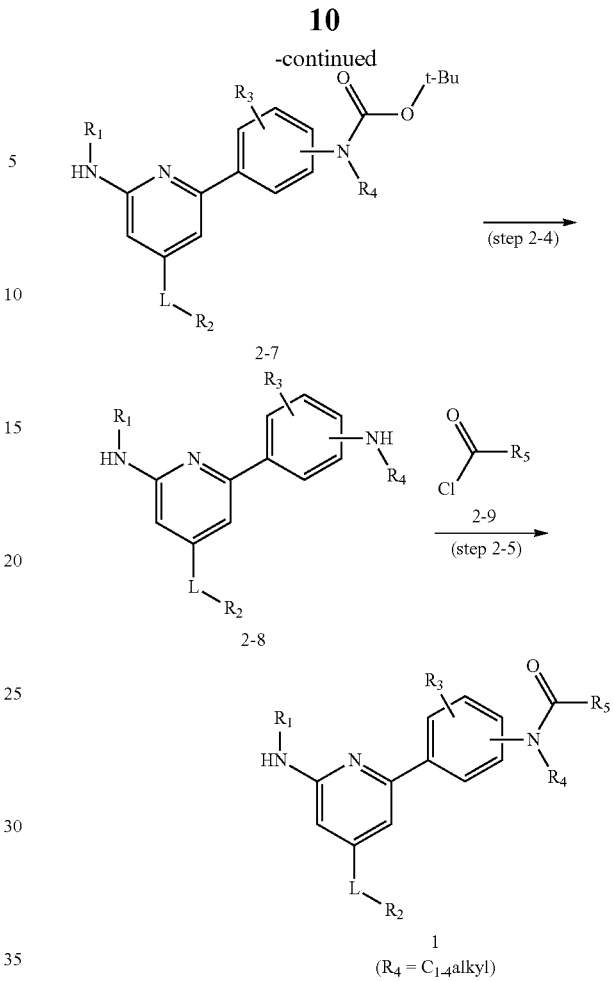

Step 2-1 is a step of reacting the compound represented by Chemical Formula 2-1 and the compound represented by Chemical Formula 2-2 to prepare a compound represented by Chemical Formula 2-3. The reaction is a Suzuki coupling reaction, which is preferably carried out in the presence of a palladium catalyst and a base.

Step 2-2 is a step of reacting the compound represented by Chemical Formula 2-3 and the compound represented by Chemical Formula 2-4 to prepare a compound represented by Chemical Formula 2-5. The reaction is an amine substitution reaction, which is preferably carried out in the presence of a palladium catalyst and a base.

Step 2-3 is a step of reacting the compound represented by Chemical Formula 2-5 and the compound represented by Chemical Formula 2-6 to prepare a compound represented by Chemical Formula 2-7. The reaction is preferably carried out in the presence of sodium hydride.

Step 2-4 is a step of reacting the compound represented by Chemical Formula 2-7 with acid to prepare a compound represented by Chemical Formula 2-8.

Step 2-5 is a step of reacting the compound represented by Chemical Formula 2-8 and the compound represented by Chemical Formula 2-9 to prepare a compound represented by Chemical Formula 1. The reaction is an amidation reaction, which is preferably carried out in the presence of a tertiary amine.

Further, in Reaction Scheme 2, a reaction for protecting with a protecting group and a reaction for removing the protecting group depending on each substituent may be added.

The production method of each step described above can be more embodied in the Examples described later.

According to a further embodiment of the present disclosure, there is provided a pharmaceutical composition for preventing or treating autoimmune diseases or cancer diseases, which is effective for BTK inhibitory actions, comprising the compound represented by Chemical Formula 1, or a pharmaceutically acceptable salt, hydrate, solvate or isomer thereof as an active ingredient.

In this case, the autoimmune diseases include rheumatoid arthritis, systemic lupus erythematosus, childhood diabetes, psoriasis, aphthous stomatitis, chronic thyroiditis, acquired aplastic anemia, primary cirrhosis, ulcerative colitis, Behcet's disease, Crohn's disease, Silicosis, asbestosis, Sjogren's syndrome, Guillain-Barre syndrome, dermatomyositis, polymyositis, multiple sclerosis, autoimmune hemolytic anemia, autoimmune encephalomyelitis, myasthenia gravis, Graves thyroid hyperplasia, nodular polyarteritis, ankylosing spondylitis, fibrositis, temporal arteritis, Wilson's disease, or Fanconi syndrome.

The cancer includes blood cancer, extranodal marginal zone B-cell lymphoma, glioblastoma, lymphoplasmacytic lymphoma, acute myelogenous leukemia, macroglobulinemia, B cell lymphoma, chronic lymphocytic leukemia, follicular lymphoma, non-hodgkin lymphoma, diffuse large B cell lymphoma, hariy cell leukemia, mantle cell lymphoma, glioblastoma, bladder cancer, pancreatic cancer, ovarian cancer, colorectal cancer, renal cancer, gastric cancer, transitional cell carcinoma, carcinoid tumor, breast cancer, non-small cell lung cancer, or multiple myeloma.

As used herein, the term "prevention" refers to any act to delay or inhibit occurrence, spread or recurrence of the above-mentioned diseases by administration of the composition of the present invention, and "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/ or glycine and the like. but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the Pharmaceutical composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present disclosure or a pharmaceutically acceptable salt, hydrate, solvate or isomer thereof can be usefully used for the prevention or treatment of autoimmune diseases or cancers.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Example 1: Preparation of N-(4-(4-benzyl-6-(5-methyl-1H-pyrazol-3-ylamino)pyridin-2-yl)phenyl) acrylamide Step 1-1: Preparation of 4-benzyl-2,6-dichloropyridine

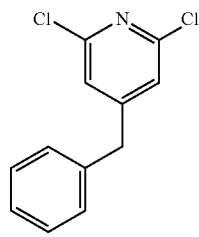 [SMILES: Clc1cc(Cc2ccccc2)cc(Cl)n1]

(2,6-Dichloropyridin-4-yl)boronic acid (7.0 g, 1.0 eq) was added to ethanol (70.0 mL) and toluene (20.0 mL) under nitrogen. Tetrakis(triphenylphosphine)palladium (4.2 g, 0.1 eq), sodium carbonate (15.3 g, 4.0 eq) and benzyl bromide (5.8 g 0.95 eq) were added sequentially, and then the mixture was reacted at 90 to 100° C. for 2 hours. After cooling to 30° C. or less, water (560.0 mL) and ethyl acetate (420.0 mL) were added thereto for extraction. The separated ethyl acetate layer was dried over anhydrous sodium sulfate and then concentrated under reduced pressure. The resulting residue was purified by column chromatography (ethyl acetate:hexane=1:10) to give the title compound (4.6 g, yield: 53.6%).

Step 1-2: Preparation of 4-benzyl-2-chloro-6-(4-nitrophenyl)pyridine

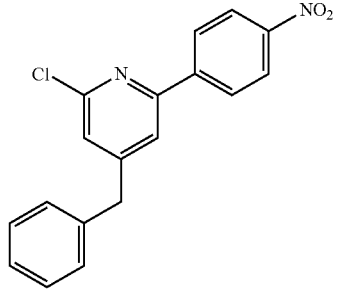 [SMILES: O=[N+]([O-])c1ccc(-c2cc(Cc3ccccc3)cc(Cl)n2)cc1]

After the intermediate (2.0 g, 1.0 eq) obtained in step 1-1 was dissolved in 1,4-dioxane (20.0 mL) under nitrogen, tetrakis(triphenylphosphine)palladium (485.3 mg, 0.1 eq), sodium carbonate (1.8 g, 4.0 eq) and 4-nitrophenylboronic acid (0.7 g, 1.0 eq) were added sequentially, and then the mixture was stirred under reflux for 6 hours to terminate the reaction. After cooling to 30° C. or less, water (40.0 mL) and ethyl acetate (40.0 mL) were added thereto for extraction. The separated ethyl acetate layer was dried over anhydrous sodium sulfate and then concentrated under reduced pressure. The resulting residue was purified by column chromatography (ethyl acetate:hexane=1:5) to give the title compound (272.8 mg, yield: 20.0%).

Step 1-3: Preparation of t-butyl 3-amino-5-methyl-1H-pyrazole-1-carboxylate

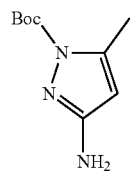

Dichloromethane (20.0 mL) was added to 5-methyl-1H-pyrazol-3-amine (2.0 g, 1.0 eq) and then cooled to 0~5° C. After di-t-butyl dicarbonate (6.9 mL, 1.5 eq) and 4-dimethylaminopyridine (0.2 g, 0.1 eq) were added, the mixture was stirred at room temperature for 30 minutes. Saturated sodium bicarbonate aqueous solution (20.0 mL) was added thereto, and then the separated dichloromethane layer was dried over anhydrous sodium sulfate, and then concentrated under reduced pressure. The resulting residue was purified by column chromatography (ethyl acetate:hexane=1:1) to give the title compound (1.8 g, yield: 50.0%).

Steps 1-4: Preparation of t-butyl 3-((4-benzyl-6-(4-nitrophenyl)pyridin-2-yl)amino)-5-methyl-1H-pyrazole-1-carboxylate

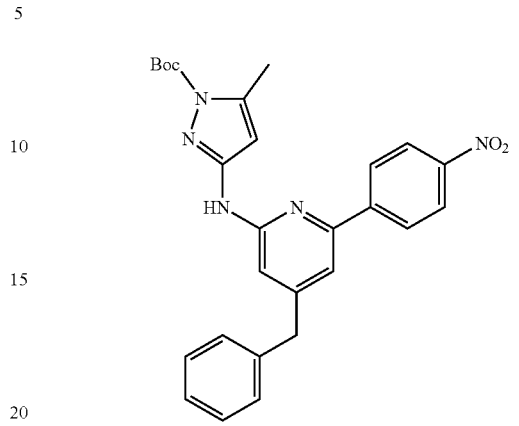

The intermediate (270.0 mg, 1.0 eq) obtained in step 1-2 was dissolved in 1,4-dioxane (2.7 mL). Tris(dibenzylideneacetone)dipalladium(0) (152.3 mg, 0.2 eq), Xantphos (145.8 mg, 0.3 eq), the intermediate (248.5 mg, 1.5 eq) obtained in step 1-3, and sodium carbonate (489.7 mg, 3.0 eq) were added sequentially. The mixture was stirred under reflux for 4 hours to complete the reaction. After cooling to 30° C. or less, water (6.0 mL) and ethyl acetate (6.0 mL) were added thereto for extraction. The separated ethyl acetate layer was dried over anhydrous sodium sulfate and then concentrated under reduced pressure. The resulting residue was purified by column chromatography (ethyl acetate:hexane=2:1) to give the title compound (265.1 mg, yield: 65.0%).

Steps 1-5: Preparation of t-butyl 3-((6-(4-aminophenyl)-4-benzylpyridin-2-yl)amino)-5-methyl-1H-pyrazole-1-carboxylate

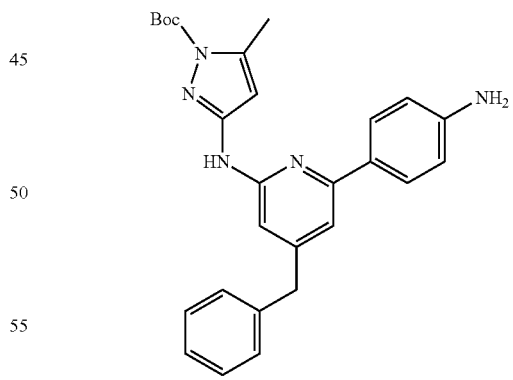

The intermediate (260.0 mg, 1.0 eq) obtained in step 1-4 was dissolved in methanol (2.6 mL) and dichloromethane (2.6 mL). After replacing the inside with nitrogen gas, 10% palladium/carbon (52.0 mg) was added. After replacing the inside of the reactor with hydrogen gas two or three times, the reaction was carried out for 2 hours at room temperature with a hydrogen gas balloon. The mixture was filtered through celite and washed with methanol (2.6 mL) and dichloromethane (2.6 mL), and the organic layer was concentrated under reduced pressure. The resulting residue was purified by column chromatography (ethyl acetate:hexane=2:1) to give the title compound (203.0 mg, yield: 83.3%).

Steps 1-6: Preparation of t-butyl 3-((6-(4-acrylamidophenyl)-4-benzylpyridin-2-yl)amino)-5-methyl-1H-pyrazole-1-carboxylate

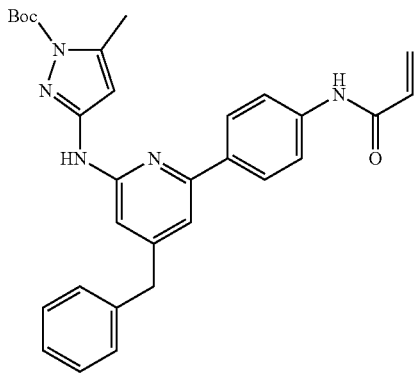 [SMILES: C=CC(=O)Nc1ccc(-c2cc(Cc3ccccc3)cc(Nc3cc(C)n(C(=O)OC(C)(C)C)n3)n2)cc1]

After the intermediate (70.0 mg, 1.0 eq) obtained in step 1-5 was dissolved in dichloromethane (700 uL), diisopropylethylamine (29.5 uL, 1.1 eq) was slowly added dropwise at 0~10° C. for 1 hour, Acryloyl chloride (11.3 uL, 0.9 eq) was slowly added dropwise and then stirred at 0~5° C. for 1 hour. Water (700 uL) was added to separate dichloromethane. The separated organic layer was dried over anhydrous sodium sulfate and then concentrated under reduced pressure. The resulting residue was purified by column chromatography (ethyl acetate:hexane=2:1) to give the title compound (55.7 mg, yield: 71.0%).

Step 1-7: Preparation of N-(4-(4-benzyl-6-(5-methyl-1H-pyrazol-3-ylamino)pyridin-2-yl)phenyl)acrylamide

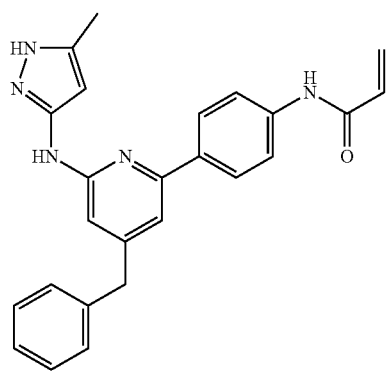 [SMILES: C=CC(=O)Nc1ccc(-c2cc(Cc3ccccc3)cc(Nc3cc(C)[nH]n3)n2)cc1]

The intermediate (55.0 mg, 1 eq) obtained in step 1-6 was dissolved in dichloromethane (550.0 uL) and then cooled to 0~10° C. Trifluoroacetic acid (165.4 uL, 20 eq) was slowly added dropwise and then the mixture was stirred for 3 hours. After adjusting the pH to 9~12 using saturated sodium bicarbonate aqueous solution, the separated dichloromethane layer was dried over anhydrous sodium sulfate, and then concentrated under reduced pressure. The resulting residue was purified by column chromatography (dichloromethane:methanol=15:1) to give the title compound (14.1 mg, yield: 32.0%).

1H NMR (500 MHz, MeOD): 7.91-7.89 (d, 2H), 7.73-7.72 (d, 2H), 7.31-7.24 (m, 4H), 7.21-7.20 (m, 1H), 7.06 (s, 1H), 6.67 (s, 1H), 6.44-6.39 (m, 2H), 6.0 (s, 1H), 5.78-5.76 (d, 1H), 3.94 (s, 2H), 2.24 (s, 3H)

Example 2: Preparation of N-(3-(4-benzyl-6-(5-methyl-1H-pyrazol-3-ylamino)pyridin-2-yl)phenyl)acrylamide Step 2-1: Preparation of 4-benzyl-2-chloro-6-(3-nitrophenyl)pyridine

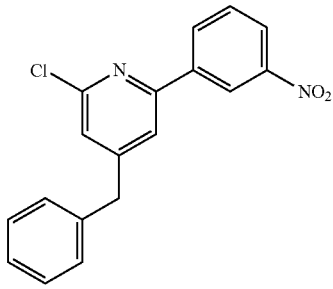 [SMILES: O=[N+]([O-])c1cccc(-c2cc(Cc3ccccc3)cc(Cl)n2)c1]

After the intermediate (5.0 g, 1.0 eq) obtained in step 1-1 of Example 1 was dissolved in 1,4-dioxane (200.0 mL), tetrakis(triphenylphosphine)palladium (2.4 mg, 0.1 eq), sodium carbonate (8.5 g, 4.0 eq) and 3-nitrophenylboronic acid (3.3 g, 1.0 eq) were added sequentially, and then the mixture was stirred under reflux for 6 hours to terminate the reaction. After cooling to 30° C. or less, water (100.0 mL) and ethyl acetate (100.0 mL) were added thereto for extraction. The separated ethyl acetate layer was dried over anhydrous sodium sulfate and then concentrated under reduced pressure. The resulting residue was purified by column chromatography (ethyl acetate:hexane=1:5) to give the title compound (2.3 mg, yield: 36.1%).

Step 2-2: Preparation of t-butyl 3-((4-benzyl-6-(3-nitrophenyl)pyridin-2-yl)amino)-5-methyl-1H-pyrazole-1-carboxylate

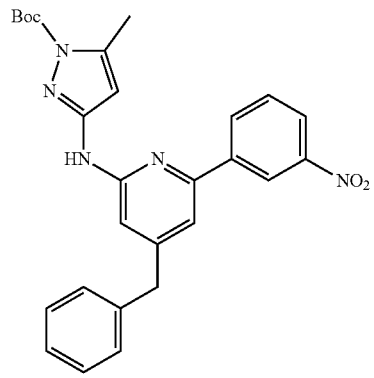 [SMILES: Cc1cc(Nc2cc(Cc3ccccc3)cc(-c3cccc(N)c3)n2)nn1C(=O)OC(C)(C)C]

The intermediate (500.0 mg, 1.0 eq) obtained in step 2-1 was dissolved in 1,4-dioxane (5.0 mL), tris(dibenzylideneacetone)dipalladium(0) (282.0 mg, 0.2 eq), Xantphos (267.3 mg, 0.3 eq), t-butyl 3-amino-5-methyl-1H-pyrazole-1-carboxylate (364.5 mg, 1.2 eq) which is the intermediate obtained in step 1-3 of Example 1, and sodium carbonate (489.7 mg, 3.0 eq) were added sequentially, and then the mixture was stirred under reflux to complete the reaction. After cooling to 30° C. or less, water (10.0 mL) and ethyl acetate (10.0 mL) were added, and the layers were separated. The ethyl acetate layer was dried over anhydrous sodium sulfate and concentrated under reduced pressure. The resulting residue was purified by column chromatography (ethyl acetate:hexane=1:1) to give the title compound (463.6 mg, yield: 62.0%).

Step 2-3: Preparation of t-butyl 3-((6-(3-aminophenyl)-4-benzylpyridin-2-yl)amino-5-methyl-1H-pyrazole-1-carboxylate

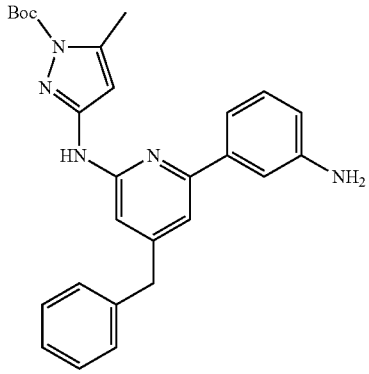

After the intermediate (200.0 mg, 1 eq) obtained in step 2-2 was dissolved in methanol (2.0 mL) and dichloromethane (2.0 mL), 10% palladium/carbon (40.0 mg) was added thereto, and then the mixture was stirred for 2 hours at room temperature using a hydrogen gas balloon to complete the reaction. The reaction mixture was filtered through celite and washed with methanol (2.0 mL) and dichloromethane (2.0 mL) and concentrated. The resulting residue was purified by column chromatography (ethyl acetate:hexane=1:1) to give the title compound (150.1 mg, yield: 80.0%).

Step 2-4: Preparation of t-butyl 3-((6-(3-acrylamidophenyl)-4-benzylpyridin-2-yl)amino)-5-methyl-1H-pyrazole-1-carboxylate

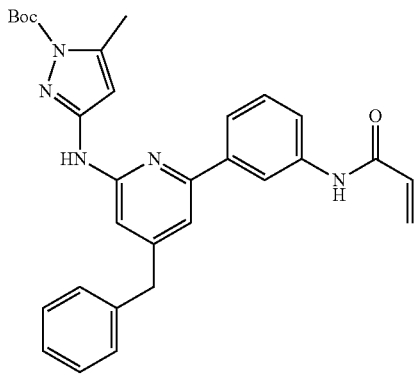 [SMILES: C=CC(=O)Nc1cccc(-c2cc(Cc3ccccc3)cc(Nc3cc(C)n(C(=O)OC(C)(C)C)n3)n2)c1]

The intermediate (150.0 mg, 1 eq) obtained in step 2-3 was dissolved in dichloromethane (1.5 mL) and then cooled to 0~10° C. Diisopropylamine (63.1 uL, 1.1 eq) was slowly added dropwise, followed by slow dropwise addition of acryloyl chloride (24.1 uL, 0.9 eq). The reaction mixture was stirred at 0~10° C. for 1 hour to complete the reaction. After adjusting the pH to 9~12 using saturated sodium bicarbonate aqueous solution, the dichloromethane layer was dried over anhydrous sodium sulfate and then concentrated under reduced pressure. The resulting residue was purified by column chromatography (ethyl acetate:hexane=1:1) to give the title compound (55.5 mg, yield: 71.0%).

Step 2-5: Preparation of N-(3-(4-benzyl-6-((5-methyl-1H-pyrazol-3-yl)amino)pyridin-2-yl)phenyl)acrylamide

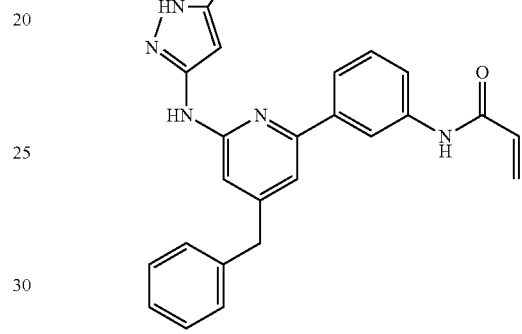

The title compound (14.1 mg, yield: 32%) was obtained in the same manner as in Step 1-7 of Example 1, except that in steps 1-7 of Example 1, the intermediate (55.0 mg, 1 eq) obtained in step 2-4 was used instead of the intermediate obtained in step 1-6.

1H NMR (500 MHz, MeOD): 8.27 (s, 1H), 7.68-7.65 (t, 2H), 7.42-7.39 (t, 1H), 7.32-7.25 (m, 4H), 7.22-7.20 (t, 1H), 7.09 (s, 1H), 6.70 (s, 1H), 6.45-6.37 (m, 2H), 6.1 (s, 1H), 5.77-5.76 (d, 1H), 3.96 (s, 2H), 2.25 (s, 3H)

Example 3: Preparation of N-(4-(4-benzyl-6-((5-methyl-1H-pyrazol-3-yl)amino)pyridin-2-yl)phenyl)propiolamide Step 3-1: Preparation of t-butyl 3-((4-benzyl-6-(4-propiolamidophenyl)pyridin-2-yl)amino)-5-methyl-1H-pyrazole-1-carboxylate

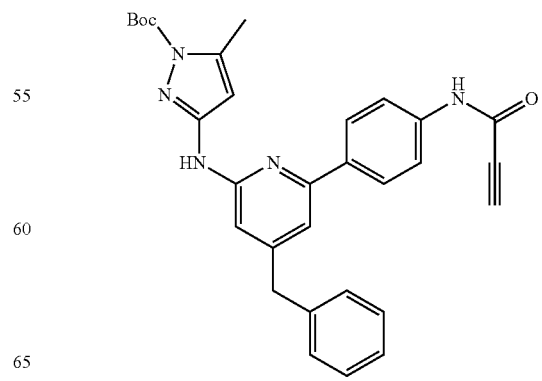

The title compound (18.9 mg, yield: 85%) was obtained in the same manner as in step 1-6 of Example 1, except that in step 1-6 of Example 1, propioloyl chloride was used instead of acryloyl chloride.

Step 3-2: Preparation of N-(4-(4-benzyl-6-((5-methyl-1H-pyrazol-3-yl)amino)pyridin-2-yl)phenyl) propionolamide

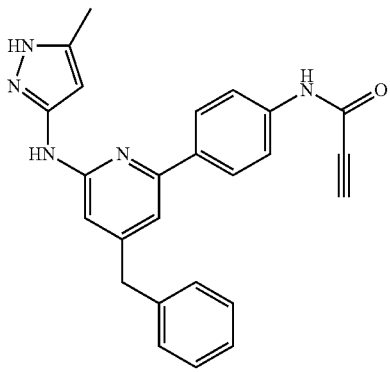 [SMILES: C#CC(=O)Nc1ccc(-c2cc(Cc3ccccc3)cc(Nc3cc(C)[nH]n3)n2)cc1]

The title compound (5.3 mg, yield: 35%) was obtained in the same manner as in step 1-7 of Example 1, except that in steps 1-7 of Example 1, the intermediate obtained in step 3-1 was used instead of the intermediate obtained in step 1-6.

1H NMR (500 MHz, MeOD): 7.91-7.89 (d, 2H), 7.67-7.66 (d, 2H), 7.31-7.20 (m, 5H), 7.08 (s, 1H), 6.68 (s, 1H), 6.0 (s, 1H), 3.95 (s, 2H), 3.75 (s, 1H), 2.25 (s, 3H)

Example 4: Preparation of N-(3-(4-benzyl-6-(5-cyclopentyl-1H-pyrazol-3-ylamino)pyridin-2-yl) phenyl)acrylamide Step 4-1: Preparation of 3-cyclopentyl-3-oxopropanenitrile

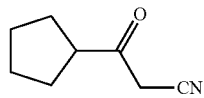

Methyl cyclopentane carboxylate (2.0 g, 1 eq) was dissolved in tetrahydrofuran (20.0 mL) at room temperature under nitrogen gas. Acetonitrile (3.3 mL, 4 eq) and 60% sodium hydride (749.3 mg, 1.2 eq) were added thereto. The mixture was stirred at 90° C. for 4 hours. Water (40.0 mL) and ethyl acetate (40.0 mL) were added to the reaction solution cooled to 30° C. or less, and then the pH was adjusted to 5~7 using 1N hydrochloric acid aqueous solution and the layer was separated. The separated ethyl acetate layer was dried over anhydrous sodium sulfate and then concentrated under reduced pressure. The resulting residue was purified by column chromatography (ethyl acetate: hexane=1:5) to give the title compound (1.1 g, yield: 52.2%).

Step 4-2: Preparation of 5-cyclopentyl-1H-pyrazol-3-amine

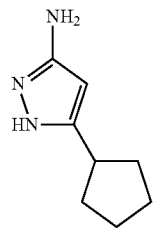 [SMILES: Nc1cc(C2CCCC2)[nH]n1]

The intermediate (1.1 g, 1 eq) obtained in step 4-1 was dissolved in 99% ethanol (5.5 mL). Hydrazine monohydrate (1.9 mL, 5 eq) was added thereto and then stirred at 90° C. for 4 hours. The reaction solution cooled to 30° C. or less was dried over anhydrous sodium sulfate, and then concentrated to give the title compound (1.1 g, yield: 94.0%) without separation.

Step 4-3: Preparation of t-butyl 3-amino-5-cyclopentyl-1H-pyrazole-1-carboxylate

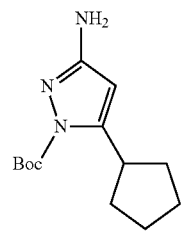

The title compound (420.1 mg, 23.0%) was obtained in the same manner as in step 1~3 of Example 1, except that in steps 1-3 of Example 1, the intermediate obtained in step 4-2 was used instead of 5-methyl-1H-pyrazol-3-amine.

Step 4-4: Preparation of t-butyl 3-((4-benzyl-6-(3-nitrophenyl)pyridin-2-yl)amino)-5-cyclopentyl-1H-pyrazole-1-carboxylate

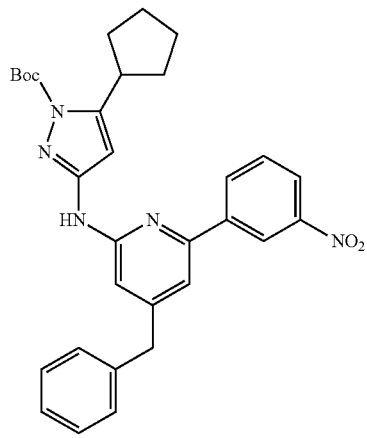 [SMILES: CC(C)(C)OC(=O)n1nc(Nc2cc(Cc3ccccc3)cc(-c3cccc([N+](=O)[O-])c3)n2)cc1C1CCCC1]

The intermediate (500.0 mg, 1 eq) obtained in step 2-1 of Example 2 was dissolved in 1,4-dioxane (5.0 mL). Tris (dibenzylideneacetone)dipalladium(0) (282.0 mg, 0.2 eq), Xantphos (267.3 mg, 0.3 eq), the intermediate (464.4 mg, 1.2 eq) obtained in step 4-3, and sodium carbonate (489.7 mg, 3.0 eq) were added sequentially. The mixture was stirred under reflux for 4 hours to complete the reaction. After cooling to 30° C. or less, water (10.0 mL) and ethyl acetate (10.0 mL) were added thereto for extraction. The separated ethyl acetate layer was dried over anhydrous sodium sulfate and concentrated under reduced pressure. The resulting residue was purified by column chromatography (ethyl acetate:hexane=1:1) to give the title compound (376.2 mg, yield: 45.3%).

Step 4-5: Preparation of t-butyl 3-((6-3-aminophenyl)-4-benzylpyridin-2-yl)amino)-5-cyclopentyl-1H-pyrazole-1-carboxylate

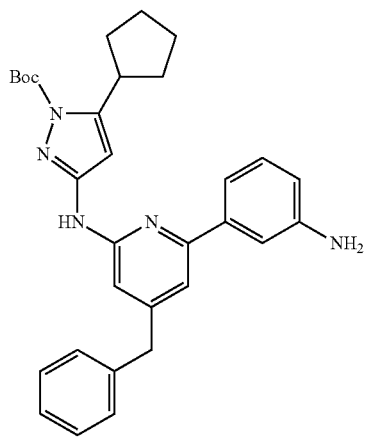

The title compound (160.0 mg, 80.0%) was obtained in the same manner as in step 1-5 of Example 1, except that in step 1-5 of Example 1, the intermediate obtained in step 4-4 was used instead of the intermediate obtained in step 1-4.

Step 4-6: Preparation of t-butyl 3-((6-3-acrylamidophenyl)-4-benzylpyridin-2-yl)amino)-5-cyclopentyl-1H-pyrazole-1-carboxylate

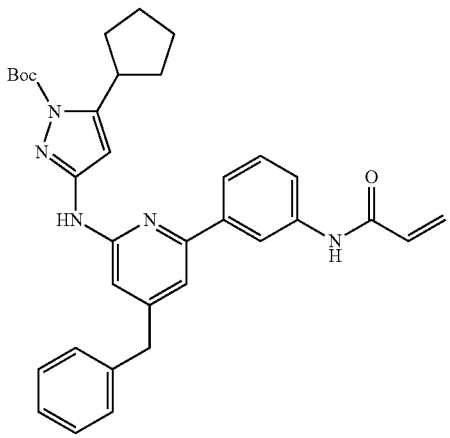 [SMILES: C=CC(=O)Nc1cccc(-c2cc(Cc3ccccc3)cc(Nc3cc(C4CCCC4)n(C(=O)OC(C)(C)C)n3)n2)c1]

The title compound (120.2 mg, 68.0%) was obtained in the same manner as in step 1-6 of Example 1, except that in step 1-6 of Example 1, the intermediate obtained in step 4-5 was used instead of the intermediate obtained in step 1-5.

Step 4-7: Preparation of N-(3-(4-benzyl-6-(5-cyclopentyl-1H-pyrazol-3-ylamino)pyridin-2-yl)phenyl)acrylamide

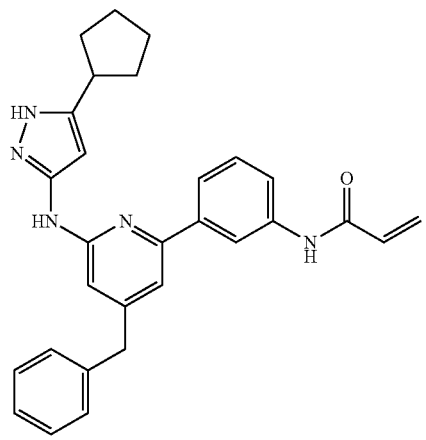 [SMILES: C=CC(=O)Nc1cccc(-c2cc(Cc3ccccc3)cc(Nc3cc(C4CCCC4)[nH]n3)n2)c1]

The title compound (37.5 mg, 32.0%) was obtained in the same manner as in step 1-7 of Example 1, except that in step 1-7 of Example 1, the intermediate obtained in step 4-6 was used instead of the intermediate obtained in step 1-6.

1H NMR (500 MHz, CDCl$_3$): 8.0 (s, 1H), 7.82-7.80 (m, 1H), 7.57-7.56 (m, 1H), 7.36-7.18 (m, 6H), 7.01 (s, 1H), 6.68 (s, 1H), 6.46-6.42 (d, 1H), 6.35-6.30 (m, 1H), 5.82 (s, 1H), 5.76-5.74 (d, 1H), 3.91 (s, 2H), 3.04-3.00 (m, 1H), 1.76-1.65 (m, 8H)

Example 5: Preparation of N-(3-(4-benzyl-6-((5-phenyl-1H-pyrazol-3-yl)amino)pyridin-2-yl)phenyl)acrylamide

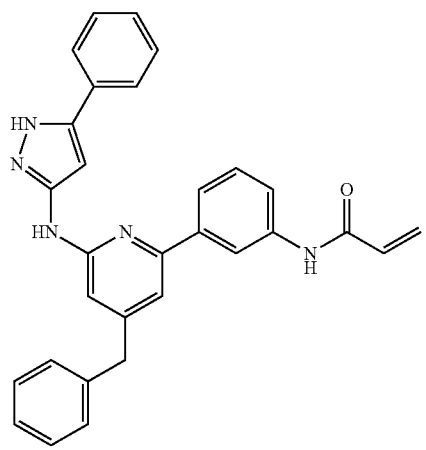 [SMILES: C=CC(=O)Nc1cccc(-c2cc(Cc3ccccc3)cc(Nc3cc(-c4ccccc4)[nH]n3)n2)c1]

The title compound (36.5 mg, 28.5%) was obtained in the same manner as in Example 4, except that in step 4-1 of Example 4, methyl benzoate was used instead of 3-cyclopentyl-3-oxopropanenitrile.

1H NMR (500 MHz, CDCl₃): 10.3 (s, 1H), 9.4 (s, 1H), 8.48 (s, 1H), 7.76-7.75 (d, 2H), 7.67-7.66 (d, 1H), 7.62-7.60 (d, 1H), 7.43-7.33 (m, 4H), 7.31-7.27 (m, 5H), 7.22-7.21 (m, 2H), 7.10 (s, 1H), 6.48-6.45 (m, 1H), 6.30-6.26 (d, 1H), 5.79-5.77 (d, 1H), 3.93 (s, 2H)

Example 6: Preparation of N-(3-(4-benzyl-6-((5-methyl-1H-pyrazol-3-yl)amino)pyridin-2-yl)phenyl)propiolamide

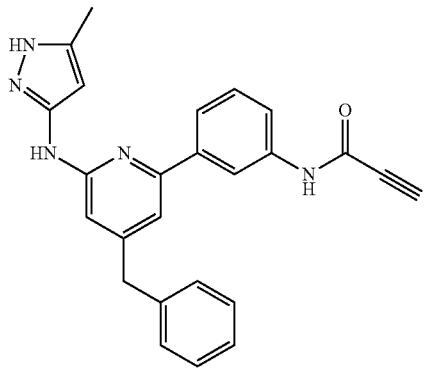 [SMILES: C#CC(=O)Nc1cccc(-c2cc(Cc3ccccc3)cc(Nc3cc(C)[nH]n3)n2)c1]

The title compound (5.6 mg, yield: 75%) was obtained in the same manner as in Example 2, except that in step 2-4 of Example 2, propioloyl chloride was used instead of acryloyl chloride.

1H NMR (500 MHz, CDCl₃): 8.16 (s, 1H), 7.68-7.37 (d, 1H), 7.56-7.54 (d, 1H), 7.41-7.37 (t, 1H), 7.33-7.22 (m, 5H), 7.12 (s, 1H), 7.07 (s, 1H), 6.99 (s, 1H), 6.51 (s, 1H), 3.97 (s, 2H), 2.93 (s, 1H), 2.54 (s, 3H)

Example 7: Preparation of N-(3-(4-benzyl-6-((5-(4-phenoxyphenyl)-1H-pyrazol-3-yl)amino)pyridin-2-yl)phenyl)acrylamide

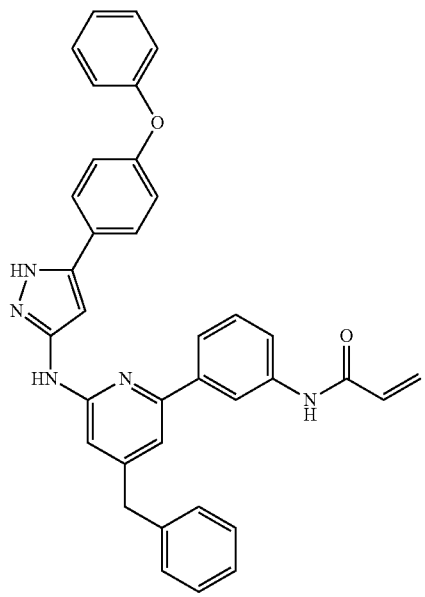 [SMILES: C=CC(=O)Nc1cccc(-c2cc(Cc3ccccc3)cc(Nc3cc(-c4ccc(Oc5ccccc5)cc4)[nH]n3)n2)c1]

The title compound (6.8 mg, 32.8%) was obtained in the same manner as in Example 4, except that in step 4-1 of Example 4, methyl 4-phenoxybenzoate was used instead of methyl cyclopentane carboxylate.

1H NMR (500 MHz, DMSO): 10.26 (s, 1H), 9.40 (s, 1H), 8.51 (s, 1H), 7.78-7.76 (d, 1H), 7.65 (d, 1H), 7.55 (s, 1H), 7.42-7.15 (m, 17H). 6.45-6.42 (m, 1H), 6.23-6.20 (d, 1H), 5.67-5.65 (d, 1H), 3.93 (s, 2H)

Example 8: Preparation of N-(3-(4-benzyl-6-(5-(4-methylbenzyl)-1H-pyrazol-3-yl)amino)pyridin-2-yl)phenyl)acrylamide

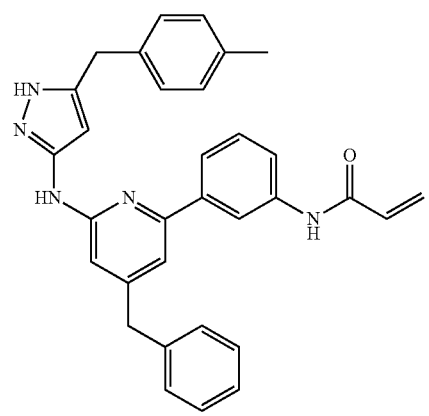 [SMILES: C=CC(=O)Nc1cccc(-c2cc(Cc3ccccc3)cc(Nc3cc(Cc4ccc(C)cc4)[nH]n3)n2)c1]

The title compound (7.5 mg, 35.8%) was obtained in the same manner as in Example 4, except that in step 4-1 of Example 4, methyl-2-(p-tosyl)acetate was used instead of methyl cyclopentane carboxylate.

1H NMR (500 MHz, CDCl₃): 8.16 (s, 1H), 8.00 (s, 1H), 7.77-7.76 (d, 1H), 7.54-7.53 (d, 1H), 7.32-7.06 (m, 10H), 6.98 (s, 1H), 6.50 (s, 1H), 6.43 (d, 1H), 6.31-6.27 (m, 1H), 5.7-5.68 (d, 1H), 4.14-4.10 (s, 2H), 3.89-3.84 (s, 2H), 2.29 (s, 3H)

Example 9: Preparation of N-(3-(4-benzyl-6-((5-(1-p-tolyl)ethyl)-1H-pyrazol-3-yl)amino)pyridin-2-yl)phenyl)acrylamide

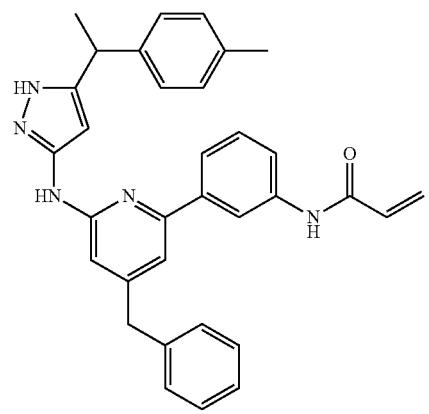 [SMILES: C=CC(=O)Nc1cccc(-c2cc(Cc3ccccc3)cc(Nc3cc(C(C)c4ccc(C)cc4)[nH]n3)n2)c1]

The title compound (3.5 mg, 35.8%) was obtained in the same manner as in Example 4, except that in step 4-1 of Example 4, methyl 2-(p-tolyl)propanoate was used instead of methyl cyclopentane carboxylate.

1H NMR (500 MHz, CDCl₃): 7.97 (s, 1H), 7.86-7.84 (d, 1H), 7.58-7.56 (d, 1H), 7.37-7.09 (m, 10H), 7.03 (s, 1H), 6.58 (s, 1H), 6.45-6.42 (d, 1H), 6.33-6.31 (m, 1H), 5.75-5.73 (d, 1H), 5.70 (s, 1H), 4.12-4.07 (q, 1H), 3.90 (s, 2H), 2.30 (s, 3H), 1.62-1.60 (d, 3H)

Example 10: Preparation of N-(3-(4-benzyl-6-((5-phenethyl-1H-pyrazol-3-yl)amino)pyridin-2-yl)phenyl)acrylamide

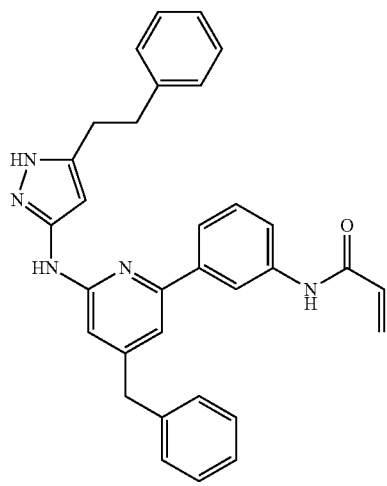 [SMILES: C=CC(=O)Nc1cccc(-c2cc(Cc3ccccc3)cc(Nc3cc(CCc4ccccc4)[nH]n3)n2)c1]

The title compound (5.2 mg, yield: 31.8%) was obtained in the same manner as in Example 4, except that in step 4-1 of Example 4, methyl-3-phenylpropanoate was used instead of methyl cyclopentane carboxylate.

1H NMR (500 MHz, CDCl₃): 8.20 (s, 1H), 8.06 (s, 1H), 7.73-7.72 (d, 1H), 7.54-7.52 (d, 1H), 7.44 (d, 1H), 7.31-7.13 (m, 10H), 6.97 (s, 1H), 6.54 (s, 1H), 6.42-6.38 (d, 1H), 6.31-6.25 (m, 1H), 5.75 (s, 1H), 5.69-5.67 (d, 1H), 3.84 (s, 1H), 2.93-2.89 (m, 4H)

Example 11: Preparation of N-(3-(6-(1H-pyrazol-3-yl)amino)-4-benzylpyridin-2-yl)phenyl)acrylamide

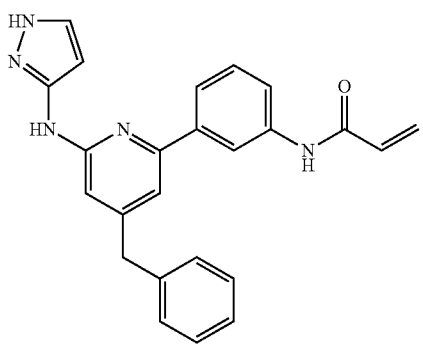 [SMILES: C=CC(=O)Nc1cccc(-c2cc(Cc3ccccc3)cc(Nc3cc[nH]n3)n2)c1]

The title compound (3.8 mg, yield 45.0%) was obtained in the same manner as in Example 2, except that in step 2-2 of Example 2, t-butyl 3-amino-1H-pyrazole-1-carboxylate was used instead of t-butyl 3-amino-5-methyl-1H-pyrazole-1-carboxylate.

1H NMR (500 MHz, MeOD): 8.13 (s, 1H), 8.07 (d, 1H), 7.80 (d, 1H), 7.69 (t, 1H), 7.68 (d, 1H), 7.31-7.16 (m, 7H), 6.40-6.34 (m, 2H), 6.1 (m. 1H), 5.71-5.69 (d, 1H)

Example 12: Preparation of N-(3-(6-(5-methyl-1H-pyrazol-3-yl)amino)pyridin-2-yl)phenyl)acrylamide Step 12-1: Preparation of 2-chloro-6-(3-nitrophenyl)pyridine

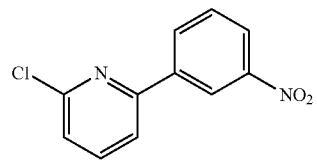 [SMILES: O=[N+]([O-])c1cccc(-c2cccc(Cl)n2)c1]

The title compound (1.6 g, yield: 45.7%) was obtained in the same manner as in step 2-1 of Example 2, except that 2,6-dichloropyridine was used in step 2-1 of Example 2.

Step 12-2: Preparation of N-(3-(6-(5-methyl-1H-pyrazol-3-yl)amino)pyridin-2-yl)phenyl)acrylamide

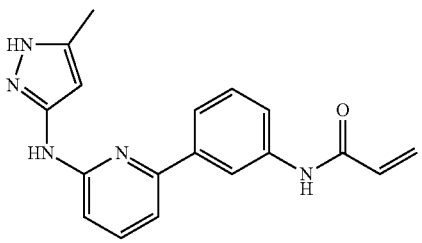 [SMILES: C=CC(=O)Nc1cccc(-c2cccc(Nc3cc(C)[nH]n3)n2)c1]

The title compound (3.8 mg, yield: 35.7%) was obtained in the same manner in steps 2-2 to 2-5 of Example 2, except that in step 2-2 of Example 2, the intermediate obtained in step 12-1 was used instead of the intermediate obtained in step 2-1.

1H NMR (500 MHz, DMSO): 8.34 (s, 1H), 7.72-7.70 (d, 1H), 7.65-7.59 (m, 2H), 7.43-7.40 (t, 1H), 7.22-7.20 (d, 1H), 6.89-6.88 (d, 1H), 6.50-6.37 (m, 2H), 5.79 (s, 1H), 5.77 (d, 1H), 2.27 (s, 3H)

Example 13: Preparation of N-(3-(6-((5-cyclopentyl-1H-pyrazol-3-yl)amino)pyridin-2-yl)phenyl)acrylamide

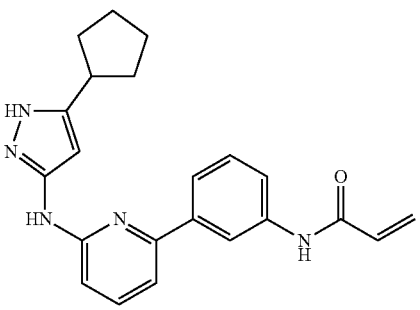 [SMILES: C=CC(=O)Nc1cccc(-c2cccc(Nc3cc(C4CCCC4)[nH]n3)n2)c1]

The title compound (5.7 mg, yield: 42.5%) was obtained in the same manner as in the steps 2-2 to 2-5 of Example 2, except that in step 2-2 of Example 2, the intermediate obtained in step 12-1 and the intermediate obtained in step 4-3 were used instead of the intermediate obtained in step 2-1 and the intermediate obtained in step 1-3, respectively.

1H NMR (500 MHz, DMSO): 8.44 (s, 1H), 7.70-7.68 (d, 1H), 7.60-7.57 (m, 2H), 7.41-7.38 (t, 1H), 7.15-7.14 (d, 1H), 7.09 (d, 1H), 6.48-6.42 (m, 2H), 6.28-6.25 (d, 1H), 5.77-5.74 (d, 1H), 3.03-3.00 (m, 1H), 2.0-1.96 (m, 2H), 1.69-1.67 (m, 2H), 1.62-1.58 (m, 4H)

Example 14: Preparation of N-(3-(6-(5-phenyl-1H-pyrazol-3-ylamino)pyridin-2-yl)phenyl)acrylamide

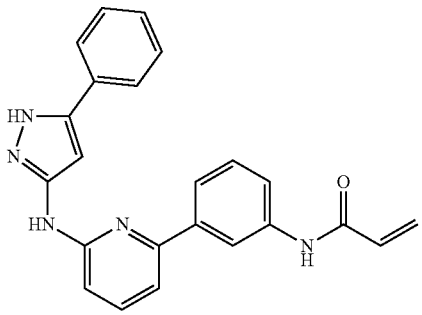 [SMILES: C=CC(=O)Nc1cccc(-c2cccc(Nc3cc(-c4ccccc4)[nH]n3)n2)c1]

The title compound (4.9 mg, yield: 39.7%) was obtained in the same manner as in the steps 2-2 to 2-5 of Example 2, except that in step 2-2 of Example 2, the intermediate obtained in step 12-1 and t-butyl 3-amino-5-phenyl-1H-pyrazole-1-carboxylate (prepared using methyl benzoate instead of 3-cyclopentyl-3-oxopropanenitrile in step 4-1) were used instead of the intermediate obtained in step 2-1 and the intermediate obtained in step 1-3, respectively.

1H NMR (500 MHz, DMSO): 12.6 (s, 1H), 10.29 (s, 1H), 9.41 (s, 1H), 8.58 (s, 1H), 7.77-7.09 (m, 12H), 6.51-6.46 (m, 1H), 6.31-6.30 (d, 1H), 6.27 (d, 1H)

Example 15: Preparation of N-(3-(6-(1H-pyrazol-3-ylamino)pyridin-2-yl)phenyl)acrylamide

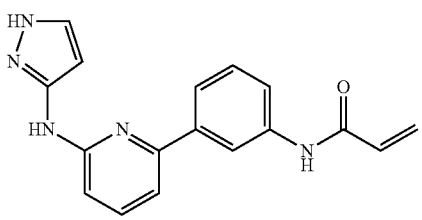 [SMILES: C=CC(=O)Nc1cccc(-c2cccc(Nc3cc[nH]n3)n2)c1]

The title compound (5.7 mg, yield: 42.5%) was obtained in the same manner as in the steps 2-2 to 2-5 of Example 2, except that in step 2-2 of Example 2, the intermediate obtained in step 12-1 and t-butyl t-butyl 3-amino-1H-pyrazole-1-carboxylate were used instead of the intermediate obtained in step 2-1 and the intermediate obtained in step 1-3, respectively.

1H NMR (500 MHz, MeOD): 8.27 (s, 1H), 7.75-7.74 (d, 1H), 7.71-7.70 (d, 1H), 7.65-7.62 (t, 1H), 7.51 (d, 1H), 7.44-7.41 (t, 1H), 7.2 (d, 1H), 6.9 (d, 1H), 6.50-6.37 (m, 3H), 5.8-5.77 (d, 1H)

Example 16: Preparation of N-(3-(4-methyl-6-(5-methyl-1H-pyrazol-3-ylamino)pyridin-2-yl)phenyl)acrylamide Step 16-1: Preparation of 2-chloro-4-methyl-6-(3-nitrophenyl)pyridine

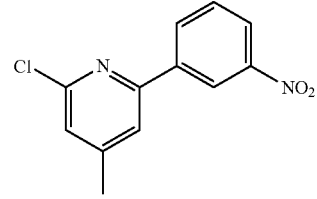 [SMILES: Cc1cc(Cl)nc(-c2cccc([N+](=O)[O-])c2)c1]

The title compound (280.0 mg, yield: 42.8%) was obtained in the same manner as in step 2-1 of Example 2, except that in step 2-1 of Example 2, 2,6-dichloro-4-methyl-pyridine was used instead of the intermediate obtained in step 1-1, Step 16-2: Preparation of N-(3-(4-methyl-6-(5-methyl-1H-pyrazol-3-ylamino)pyridin-2-yl)phenyl)acrylamide

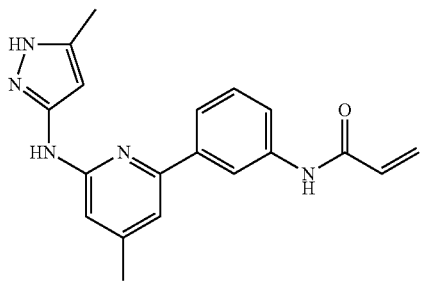 [SMILES: C=CC(=O)Nc1cccc(-c2cc(C)cc(Nc3cc(C)[nH]n3)n2)c1]

The title compound (6.7 mg, yield 48.7%) was obtained in the same manner as in steps 2-2 to 2-5 of Example 2, except that in step 2-2 of Example 2, the intermediate obtained in step 16-1 was used instead of the intermediate obtained in step 2-1.

1H NMR (500 MHz, MeOD): 8.3 (s, 1H), 7.70-7.69 (d, 1H), 7.65-7.63 (d, 1H), 7.42-7.39 (t, 1H), 7.07 (s, 1H), 6.73 (s, 1H), 6.50-6.37 (m, 2H), 6.1 (s, 1H), 5.79-5.77 (d, 1H), 2.32 (s, 3H), 2.26 (s, 3H)

Example 17: Preparation of N-(3-(6-(5-methyl-1H-pyrazol-3-yl)amino)-4-(trifluoromethyl)pyridin-2-yl)phenyl)acrylamide Step 17-1: Preparation of 2-chloro-6-(3-nitrophenyl)-4-(trifluoromethyl)pyridine

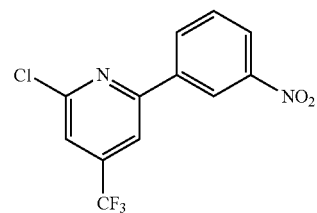 [SMILES: O=[N+]([O-])c1cccc(-c2cc(C(F)(F)F)cc(Cl)n2)c1]

The title compound (358.0 mg, yield: 41.8%) was obtained in the same manner as in step 2-1 of Example 2, except that in step 2-1 of Example 2, 2,6-dichloro-4-(trifluoromethyl)pyridine was used instead of the intermediate obtained in step 1-1.

Step 17-2: Preparation of N-(3-(6-(5-methyl-1H-pyrazol-3-yl)amino)-4-(trifluoromethyl)pyridin-2-yl)phenyl)acrylamide

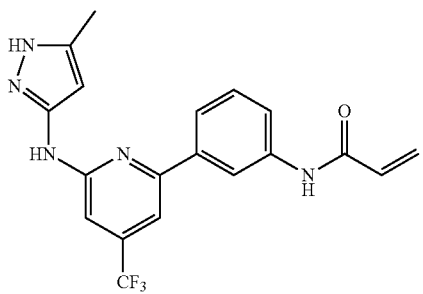 [SMILES: C=CC(=O)Nc1cccc(-c2cc(C(F)(F)F)cc(Nc3cc(C)[nH]n3)n2)c1]

The title compound (4.9 mg, yield: 42.8%) was obtained in the same manner as in the steps 2-2 to 2-5 of Example 2, except that in step 2-2 of Example 2, the intermediate obtained in step 17-1 was used instead of the intermediate obtained in step 2-1.

1H NMR (500 MHz, DMSO): 11.9 (s, 1H), 10.29 (s, 1H), 9.47 (s, 1H), 8.55 (s, 1H), 7.79-7.78 (d, 1H), 7.66-7.64 (d, 1H), 7.50 (s, 1H), 7.46-7.43 (t, 1H), 7.37 (s, 1H), 6.49-6.43 (m, 1H), 6.35 (s, 1H), 6.30-6.27 (d, 1H), 5.78-5.76 (d, 1H), 2.35 (s, 3H)

Example 18: Preparation of N-(3-(4-methyl-6-(pyridin-2-ylamino)pyridin-2-yl)phenyl)acrylamide

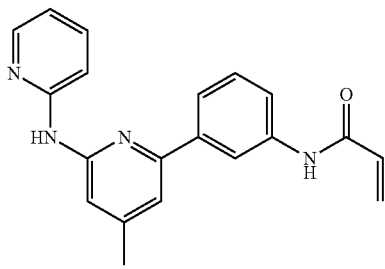 [SMILES: C=CC(=O)Nc1cccc(-c2cc(C)cc(Nc3ccccn3)n2)c1]

The title compound (7.8 mg, yield: 39.2%) was obtained in the same manner as in the steps 2-2 to 2-5 of Example 2, except that in step 2-2 of Example 2, the intermediate obtained in step 16-1 and pyridin-2-amine were used instead of the intermediate obtained in step 2-1 and the intermediate obtained in step 1-3, respectively.

1H NMR (500 MHz, CDCl$_3$): 8.26-8.25 (m, 1H), 8.04 (s, 1H), 7.71-7.59 (m, 4H), 7.37-7.34 (t, 1H), 7.17 (s, 1H), 7.09 (s, 1H), 6.83-6.81 (t, 1H), 6.45-6.42 (m, 1H), 6.32-6.30 (m, 1H), 5.72-5.70 (d, 1H), 2.30 (s, 3H)

Example 19: Preparation of N-(3-(4-((3,3-dimethylbutan-2-yl)amino)methyl)-6-(5-methyl-1H-pyrazol-3-yl)amino)pyridin-2-yl)phenyl)acrylamide Step 19-1: Preparation of 2,6-dichloro-N-(3,3-dimethylbutan-2-yl)isonicotinamide

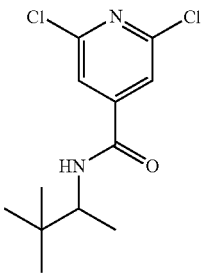 [SMILES: CC(NC(=O)c1cc(Cl)nc(Cl)c1)C(C)(C)C]

2,6-Dichloroisonicotinic acid (1.0 g, 1 eq) was dissolved in dimethylformamide (10.0 mL), and then 1,1'-carbonyldiimidazole (1.0 g, 1.2 eq) was added thereto. The mixture was stirred at room temperature (25~30° C.) for 1 hour under nitrogen gas, and then 3,3-dimethylbutane-2-amine (632.6 mg, 1.2 eg) was added and stirred at the same temperature for 2 hours to complete the reaction. Ethyl acetate (20.0 mL) and water (20.0 mL) were added for extraction, and the aqueous layer was re-extracted three times with ethyl acetate (20.0 mL). The ethyl acetate layer was dried over anhydrous sodium sulfate and then concentrated under reduced pressure. The resulting residue was purified by column chromatography (ethyl acetate: hexane=1:5) to give the title compound (1.3 g, yield: 94.0%).

Step 19-2: Preparation of N-((2,6-dichloropyridin-4-yl)methyl)-3,3-dimethylbutan-2-amine

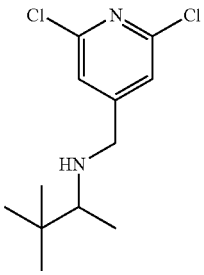 [SMILES: CC(NCc1cc(Cl)nc(Cl)c1)C(C)(C)C]

The intermediate (1.0 g, 1 eq) obtained in step 19-1 was dissolved in dichloromethane (10.0 mL) and then cooled to 0~10° C. under nitrogen gas. 1M borane-tetrahydrofuran (10.9 mL, 3.0 eq) was slowly added dropwise. The mixture was stirred at room temperature for 12 hours to complete the reaction. After the reaction solution was cooled to 0~10° C., 6N hydrochloric acid aqueous solution (12.1 mL, 20.0 eq) was slowly added dropwise, and then stirred at the same temperature for 1 hour. After adjusting the pH to 9~12 using 10N sodium hydroxide aqueous solution, the mixture was extracted twice with dichloromethane. The dichloromethane layer was separated, dried over anhydrous sodium sulfate, and then concentrated under reduced pressure. The resulting residue was purified by column chromatography (ethyl acetate:hexane=1:1) to give the title compound (0.76 g, yield: 80.0%).

Step 19-3: Preparation of N-((2-chloro-6-(3-nitrophenyl)pyridin-4-yl)methyl)-3,3-dimethylbutan-2-amine

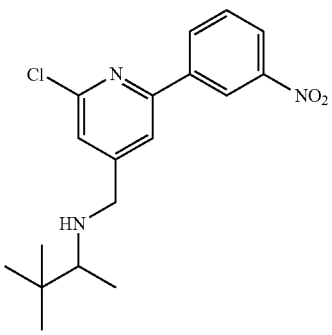 [SMILES: CC(NCc1cc(Cl)nc(-c2cccc([N+](=O)[O-])c2)c1)C(C)(C)C]

The intermediate (700.0 mg, 1 eq) obtained in step 19-2 was dissolved in 1,4-dioxane (7.0 mL). And, tetrakis(triphenylphosphine)palladium (300.0 mg, 0.1 eq), 3-nitrophenylboronic acid (447.4 mg, 1 eq), sodium carbonate (1.1 g, 4 eq) were added sequentially. The mixture was refluxed for 12 hours to complete the reaction. The reaction solution was cooled to 30° C. or less, and then extracted with water (15.0 mL) and ethyl acetate (15.0 mL). The ethyl acetate layer was separated, dried over anhydrous sodium sulfate, and then concentrated under reduced pressure. The resulting residue was purified by column chromatography (ethyl acetate:hexane=1:3) to give the title compound (504.4 mg, yield: 54.1%).

Step 19-4: Preparation of t-butyl 3-((4-(((3,3-dimethylbutan-2-yl)amino)methyl)-6-(3-nitrophenyl)pyridin-2-yl)amino)-5-methyl-1H-pyrazole-1-carboxylate

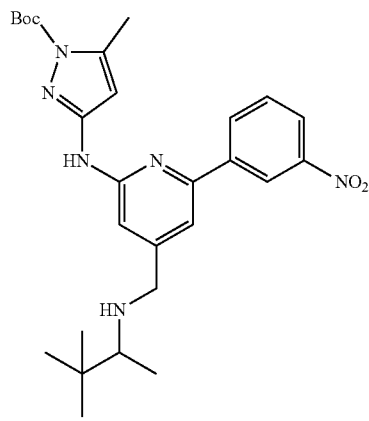

After the intermediate (0.5 g, 1 eq) obtained in step 19-3 was dissolved in 1,4-dioxane (5.0 mL), tris(dibenzylideneacetone)dipalladium(0) (263.3 mg, 0.2 eq), Xantphos (249.4 mg, 0.3 eq), t-butyl 3-amino-5-methyl-1H-pyrazole-1-carboxylate (283.4 mg, 1.0 eq), which is an intermediate obtained in step 1-3 of Example 1, and sodium carbonate (456.9 mg, 3.0 eq) were added sequentially, and the mixture was stirred under reflux for 4 hours to complete the reaction. After cooling to 30° C. or less, water (10.0 mL) and ethyl acetate (10.0 mL) were added, and the layers were separated. The ethyl acetate layer was dried over anhydrous sodium sulfate and then concentrated under reduced pressure. The resulting residue was purified by column chromatography (ethyl acetate:hexane=1:1) to give the title compound (438.2 mg, yield: 60.0%).

Step 19-5: Preparation of t-butyl 3-((6-(3-aminophenyl)-4-(((3,3-dimethylbutan-2-yl)amino)methyl)pyridin-2-yl)amino)-5-methyl-1H-pyrazole-1-carboxylate

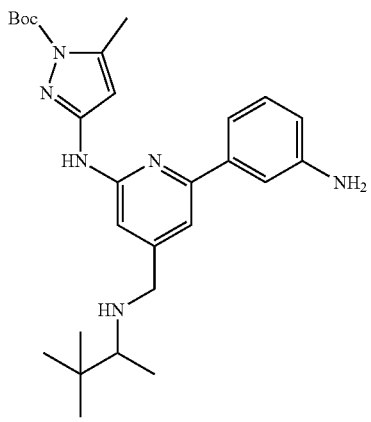 [SMILES: Cc1cc(Nc2cc(CNC(C)C(C)(C)C)cc(-c3cccc(N)c3)n2)nn1C(=O)OC(C)(C)C]

After the intermediate (400.0 mg, 1 eq) obtained in step 19-4 wad dissolved in methanol (4.0 mL) and dichloromethane (4.0 mL), 10% palladium/carbon (20.0 mg) was added and the mixture was stirred for 2 hours at room temperature using a hydrogen gas balloon to complete the reaction. The reaction mixture was filtered through celite and washed with methanol (4.0 mL) and dichloromethane (4.0 mL), and concentrated. The resulting residue was purified by column chromatography (ethyl acetate:hexane=1:1) to give the title compound (263.7 mg, yield: 70.0%).

Step 19-6: Preparation of t-butyl 3-((6-(3-acrylamidophenyl)-4-(((3,3-dimethylbutan-2-yl)amino)methyl)pyridin-2-yl)amino-1H-pyrazole-1-carboxylate

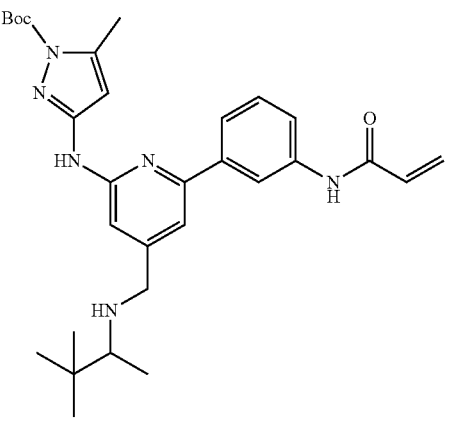 [SMILES: C=CC(=O)Nc1cccc(-c2cc(CNC(C)C(C)(C)C)cc(Nc3cc(C)n(C(=O)OC(C)(C)C)n3)n2)c1]

The intermediate (200 mg, 1 eq) obtained in step 19-5 was dissolved in dichloromethane (2.0 mL) and then cooled to 0~10° C. Diisopropylamine (80.1 uL, 1.1 eq) was slowly added dropwise thereto, and then acryloyl chloride (34.0 uL, 1.0 eq) was slowly added dropwise. The mixture was stirred at 0~5° C. for 1 hour to complete the reaction. After adding water (2.0 mL), the layers were separated, and the dichloromethane layer was dried over anhydrous sodium sulfate, and then concentrated under reduced pressure. The resulting residue was purified by column chromatography (ethyl acetate:hexane=1:1) to give the title compound (151.4 mg, yield: 68.0%).

Step 19-7: Preparation of N-(3-(4-((3,3-dimethylbutan-2-ylamino)methyl)-6-(5-methyl-1H-pyrazol-3-ylamino)pyridin-2-yl)phenyl)acrylamide

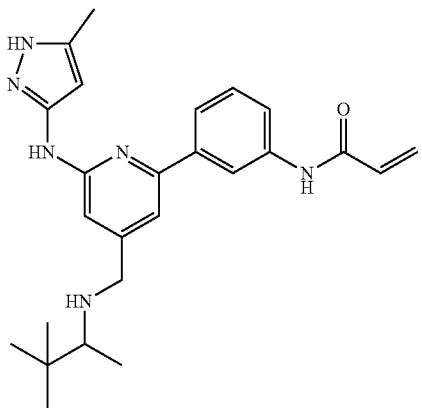 [SMILES: C=CC(=O)Nc1cccc(-c2cc(CNC(C)C(C)(C)C)cc(Nc3cc(C)[nH]n3)n2)c1]

The title compound (92.9 mg, yield: 54.0%) was obtained in the same manner as in Step 1-7 of Example 1, except that in step 1-7 of Example 1, the intermediate obtained in step 19-6 was used instead of the intermediate obtained in step 1-6.

1H NMR (500 MHz, DMSO) 8.13 (s, 1H), 8.07 (d, 1H), 7.69-7.68 (m, 2H), 7.19 (s, 1H), 6.48 (m, 1H), 6.25 (s, 1H), 6.09 (d, 1H), 5.74 (d, 1H), 4.60 (s, 2H). 2.43 (m, 1H), 2.30 (s, 3H), 1.06 (d, 3H), 0.89 (s, 9H)

Example 20: Preparation of 2-(3-acrylamidophenyl)-N-(3,3-dimethylbutan-2-yl)-6-(5-methyl-1H-pyrazol-3-ylamino)isonicotinamide Step 20-1: Preparation of 2-chloro-N-(3,3-dimethylbutan-2-yl)-6-(3-nitrophenyl)nicotinamide

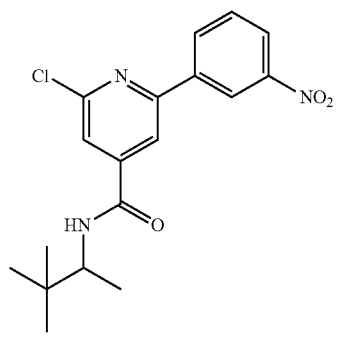 [SMILES: CC(NC(=O)c1cc(Cl)nc(-c2cccc([N+](=O)[O-])c2)c1)C(C)(C)C]

The title compound (450.0 mg, yield: 35.8%) was obtained in the same manner as in step 19-3 of Example 19, except that in step 19-3 of Example 19, the intermediate obtained in step 19-1 was used instead of the intermediate obtained in step 19-2.

Step 20-2: Preparation of 2-(3-acrylamidophenyl)-N-(3,3-dimethylbutan-2-yl)-6-(5-methyl-1H-pyrazol-3-ylamino)isonicotin amide

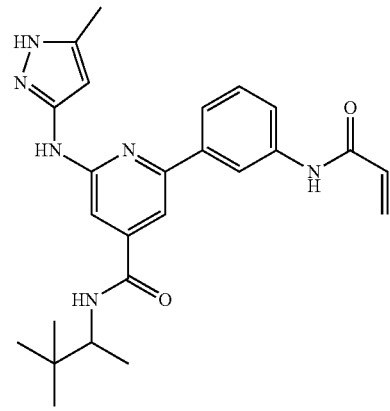 [SMILES: C=CC(=O)Nc1cccc(-c2cc(C(=O)NC(C)C(C)(C)C)cc(Nc3cc(C)[nH]n3)n2)c1]

The title compound (8.0 mg, yield 45.5%) was obtained in the same manner as in steps 19-4 to 19-7 of Example 19, except that in step 19-4 of Example 19, the intermediate obtained in step 20-1 was used instead of the intermediate obtained in step 19-3.

1H NMR (500 MHz, DMSO) 8.10 (s, 1H), 8.07 (d, 1H), 7.69-7.68 (m, 2H), 6.92 (s, 1H), 6.68 (s, 1H), 6.48 (m, 1H), 6.29 (s, 1H), 6.09 (d, 1H), 5.74 (d, 1H), 6.40 (m, 1H), 2.30 (s, 3H), 1.26 (d, 3H), 0.89 (s, 9H)

Example 21: Preparation of 2-(3-acrylamidophenyl)-N,N-dimethyl-6-((5-methyl-1H-pyrazol-3-yl)amino)isonicotinamide

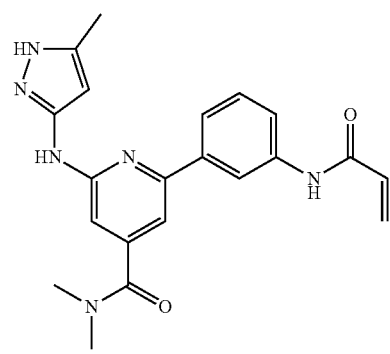 [SMILES: C=CC(=O)Nc1cccc(-c2cc(C(=O)N(C)C)cc(Nc3cc(C)[nH]n3)n2)c1]

An intermediate was prepared in the same manner in step 19-1 of Example 19, except that dimethylamine was used instead of 3,3-dimethylbutan-2-amine. The title compound (5.9 mg, yield: 57.4%) was obtained in the same manner as in steps 19-3 to 19-7 of Example 19, except that in step 19-3 of Example 19, the above intermediate was used instead of the intermediate obtained in Step 19-2.

1H NMR (500 MHz, CDCl$_3$): 7.9 (s, 1H), 7.8 (d, 1H), 7.6 (d, 1H), 7.4 (t, 1H), 7.1 (s, 1H), 6.4 (d, 1H), 6.5 (d, 1H), 6.3 (m, 1H), 5.8 (s, 1H), 5.76 (d, 1H), 3.1 (s, 3H), 3.0 (s, 3H), 2.3 (s, 3H)

Example 22: Preparation of N-(3-(6-((5-methyl-1H-pyrazol-3-yl)amino)-4-(morpholinomethyl)pyridin-2-yl)phenyl)acrylamide Step 22-1: Preparation of (2,6-dichloropyridin-4-yl)(morpholino)methanone

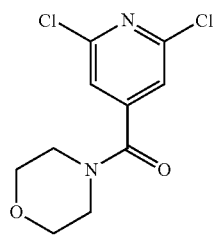 [SMILES: O=C(c1cc(Cl)nc(Cl)c1)N1CCOCC1]

2,6-dichloroisonicotinic acid (1.0 g, 1 eq) was dissolved in dimethylformamide (10.0 mL), and then 1,1-carbonyldiimidazole (1.0 g, 1.2 eq) was added thereto. After stirring for 1 hour at room temperature (25~30° C.) under nitrogen gas, morpholine (541.0 uL, 1.2 eq) was added and the mixture was stirred at the same temperature for 2 hours to complete the reaction. Ethyl acetate (20.0 mL) and water (20.0 mL) were added for extraction, and the aqueous layer was re-extracted three times with ethyl acetate (20.0 mL). The ethyl acetate layer was dried over anhydrous sodium sulfate and then concentrated under reduced pressure. The resulting residue was purified by column chromatography (ethyl acetate:hexane=1:5) to give the title compound (1.3 g, yield: 93.0%).

Step 22-2: Preparation of 4-((2,6-dichloropyridin-4-yl)methyl)morpholine

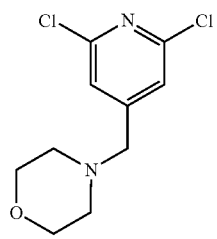 [SMILES: Clc1cc(CN2CCOCC2)cc(Cl)n1]

The intermediate (1.0 g, 1 eq) obtained in step 22-1 was dissolved in dichloromethane (10.0 mL) and then cooled to 0~10° C. under nitrogen gas. 1M borane-tetrahydrofuran (11.5 mL, 3.0 eq) was slowly added dropwise thereto. The mixture was stirred at room temperature for 12 hours to complete the reaction. After the reaction solution was cooled to 0~10° C., 6N hydrochloric acid aqueous solution (25.6 mL, 20.0 eq) was slowly added dropwise, and then stirred at the same temperature for 1 hour. After adjusting the pH to 9~12 using 10N sodium hydroxide aqueous solution, the mixture was extracted twice with dichloromethane. The dichloromethane layer was separated, dried over anhydrous sodium sulfate, and then concentrated under reduced pressure. The resulting residue was purified by column chromatography (ethyl acetate:hexane=1:1) to give the title compound (0.81 g, yield: 90.0%).

Step 22-3: Preparation of 4-((2-chloro-6-(3-nitrophenyl)pyridin-4-yl)methyl)morpholine

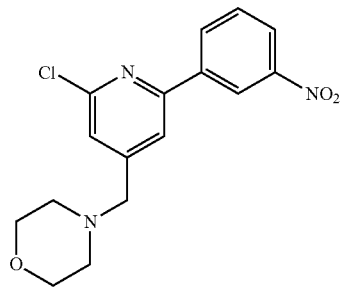 [SMILES: O=[N+]([O-])c1cccc(-c2cc(CN3CCOCC3)cc(Cl)n2)c1]

The intermediate (0.7 g, 1 eq) obtained in step 22-2 was dissolved in 1,4-dioxane (7.0 mL). And, tetrakis(triphenylphosphine)palladium (327.3 mg, 0.1 eq), 3-nitrophenyl boronic acid (472.4 mg, 1 eq), sodium carbonate (1.2 g, 4 eq) were added sequentially. The mixture was refluxed for 12 hours to complete the reaction. The reaction solution was cooled to 30° C. or less, and then extracted with water (15.0 mL) and ethyl acetate (15.0 mL). The ethyl acetate layer was separated, dried over anhydrous sodium sulfate, and then concentrated under reduced pressure. The resulting residue was purified by column chromatography (ethyl acetate:hexane=1:1) to give the title compound (486.45 mg, yield: 51.5%).

Step 22-4: Preparation of t-butyl 5-methyl-3-((4-(morpholinomethyl)-6-(3-nitrophenyl)pyridin-2-yl)amino-1H-pyrazole-1-carboxylate

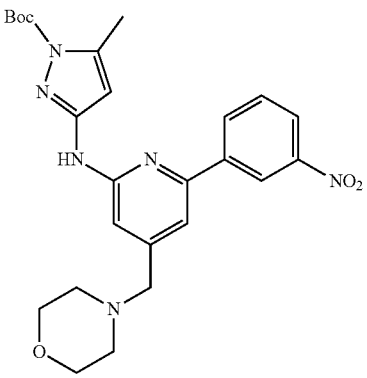 [SMILES: Cc1cc(Nc2cc(CN3CCOCC3)cc(-c3cccc([N+](=O)[O-])c3)n2)nn1C(=O)OC(C)(C)C]

After the intermediate (400.0 mg, 1 eq) obtained in step 22-3 was dissolved in 1,4-dioxane (4.0 mL), tris(dibenzylideneacetone)dipalladium(0) (219.5 mg, 0.2 eq), Xantphos (277.7 mg, 0.4 eq), t-butyl 3-amino-5-methyl-1H-pyrazole-1-carboxylate (236.3 mg, 1.0 eq), which is the intermediate obtained in step 1-3 of Example 1, and sodium carbonate (381.6 mg, 3.0 eq) were added sequentially, and the mixture was stirred under reflux for 4 hours to complete the reaction. After cooling to 30° C. or less, water (4.0 mL) and ethyl acetate (4.0 mL) were added, and then the layers were separated. The ethyl acetate layer was dried over anhydrous sodium sulfate and then concentrated under reduced pressure. The resulting residue was purified by column chromatography (ethyl acetate:hexane=5:1) to give the title compound (326.4 mg, yield: 55.0%).

Step 22-5: Preparation of t-butyl 3-((6-(3-amino-phenyl)-4-(morpholinomethyl)pyridin-2-yl)amino)-5-methyl-1H-pyrazole-1-carboxylate

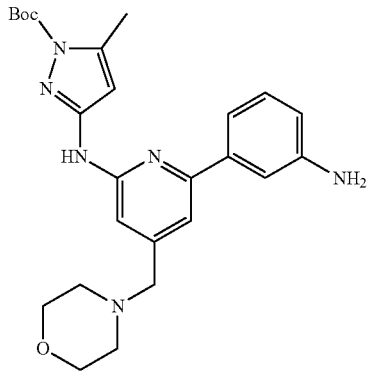

After the intermediate (100.0 mg, 1 eq) obtained in step 22-4 was dissolved in methanol (1.0 mL) and dichloromethane (1.0 mL), 10% palladium/carbon (20.0 mg) was added thereto, and the mixture was stirred at room temperature for 2 hours using a hydrogen gas balloon to complete the reaction. The mixture was filtrated through celite and washed with methanol (1.0 mL) and dichloromethane (1.0 mL) and concentrated. The resulting residue was purified by column chromatography (ethyl acetate:hexane=1:1) to give the title compound (65.0 mg, yield: 70.0%).

Step 22-6: Preparation of N-(3-(6-((5-methyl-1H-pyrazol-3-yl)amino)-4-(morpholinomethyl)pyridin-2-yl)phenyl)acrylamide

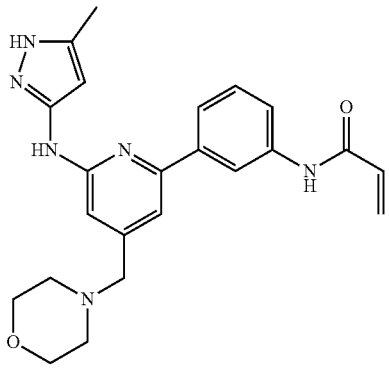 [SMILES: C=CC(=O)Nc1cccc(-c2cc(CN3CCOCC3)cc(Nc3cc(C)[nH]n3)n2)c1]

The title compound (6.9 mg, yield: 68.1%) was obtained in the same manner as in steps 2-4 and 2-5 of Example 2, except that in step 2-4 of Example 2, the intermediate obtained in step 22-5 was used instead of the intermediate obtained in step 2-3.

1H NMR (500 MHz, CDCl$_3$): 8.1 (s, 1H), 7.79-7.78 (d, 1H), 7.63-7.62 (d, 1H), 7.39-7.36 (t, 1H), 7.18 (s, 1H), 6.89 (s, 1H), 6.46-6.43 (d, 1H), 6.36-6.32 (m, 1H), 5.85 (s, 1H), 5.77-5.74 (d, 1H), 3.72-3.71 (t, 4H), 3.44 (s, 2H), 2.45 (t, 4H), 2.28 (s, 3H)

Example 23: Preparation of N-(3-(6-(5-methyl-1H-pyrazol-3-ylamino)-4-phenylpyridin-2-yl)phenyl)acrylamide

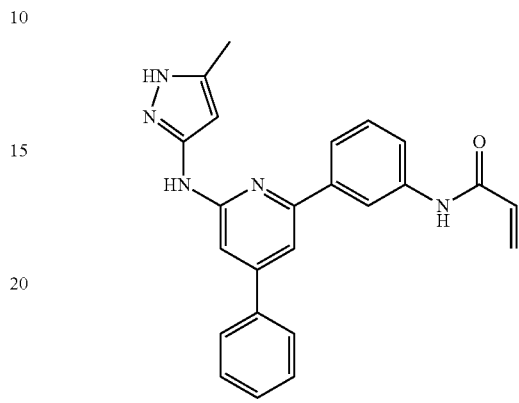

The title compound (3.2 mg, yield: 51.2%) was obtained in the same manner as in Example 2, except that in step 2-1 of Example 2, 2,6-dichloro-4-phenylpyridine was used instead of the intermediate obtained in step 1-1.

1H NMR (500 MHz, MeOD): 8.41 (s, 1H), 7.81 (d, 1H), 7.73 (s, 1H), 7.71 (t, 1H), 7.65 (d, 1H), 7.49-7.42 (m, 5H), 7.17 (s, 1H), 6.50-6.38 (m, 2H), 6.41 (s, 1H), 5.79-5.77 (d, 1H), 2.29 (s, 3H)

Example 24: Preparation of N-(3-(6-(5-ethyl-1H-pyrazol-3-ylamino)-4-methylpyridin-2-yl)phenyl)acrylamide

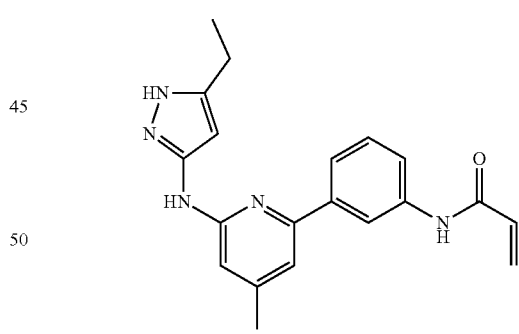

The title compound (3.3 mg, yield: 65.7%) was obtained in the same manner as in the steps 2-2 to 2-5 of Example 2, except that in step 2-2 of Example 2, the intermediate obtained in step 16-1 and t-butyl 3-amino-5-ethyl-1H-pyrazole-1-carboxylate were used instead of the intermediate obtained in step 2-1 and t-butyl 3-amino-5-methyl-1H-pyrazole-1-carboxylate, respectively.

1H NMR (500 MHz, CDCl$_3$): 8.38 (s, 1H), 7.80-7.79 (d, 1H), 7.57-5.71 (d, 1H), 7.45-7.42 (t, 1H), 7.18 (s, 1H), 6.95 (s, 1H), 6.60 (s, 1H), 6.48-6.45 (d, 1H), 6.31-6.29 (m, 1H), 5.80-5.78 (d, 1H), 2.71-2.69 (q, 2H), 2.36 (s, 3H), 1.3-1.38 (t, 1H)

Example 25: Preparation of N-(3-(6-((5-cyclopropyl-1H-pyrazol-3-yl)amino)-4-methylpyridin-2-yl)phenyl)acrylamide

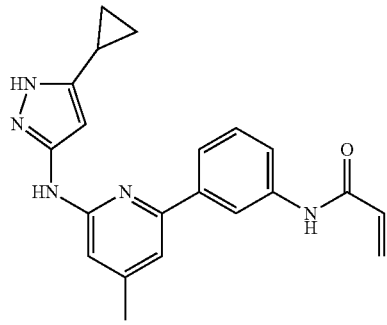 [SMILES: C=CC(=O)Nc1cccc(-c2cc(C)cc(Nc3cc(C4CC4)[nH]n3)n2)c1]

The title compound (5.2 mg, yield: 52.8%) was obtained in the same manner as in steps 2-2 to 2-5 of Example 2, except that in step 2-2 of Example 2, the intermediate obtained in step 16-1 and t-butyl 3-amino-5-cyclopropyl-1H-pyrazole-1-carboxylate were used instead of the intermediate obtained in step 2-1 and t-butyl 3-amino-5-methyl-1H-pyrazole-1-carboxylate, respectively.

1H NMR (500 MHz, MeOD): 8.27 (s, 1H), 7.70 (d, 1H), 7.69 (d, 1H), 7.08 (t, 1H), 6.71 (s, 1H), 6.49-6.38 (m, 2H), 5.80-5.78 (d, 1H), 2.33 (s, 3H), 1.89-1.88 (m, 11H), 0.92 (m, 2H), 0.73 (m, 2H)

Example 26: Preparation of N-(3-(4-methyl-6-((5-methylthiazol-2-yl)amino)pyridin-2-yl)phenyl)acrylamide

Step 26-1: Preparation of 5-methyl-N-(4-methyl-6-(3-nitrophenyl)pyridin-2-yl)thiazol-2-amine

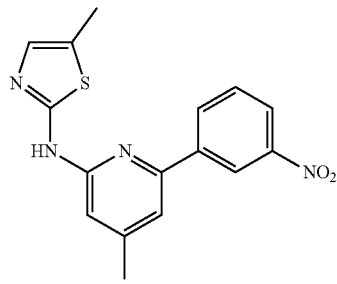 [SMILES: Cc1cc(Nc2ncc(C)s2)nc(-c2cccc([N+](=O)[O-])c2)c1]

The intermediate (500.0 mg, 1 eq) obtained in step 16-1 was dissolved in 1,4-dioxane (5.0 mL), and then palladium acetate (45.1 mg, 0.1 eq) and Xantphos (231.4 mg, 0.2 eq) were added thereto. 5-Methylthiazol-2-amine (228.3 mg, 1 eq) and cesium carbonate (1.9 g, 3 eq) were added thereto, and the mixture was reacted in a microwave reactor at 150° C. for 30 minutes. Ethyl acetate (10.0 mL) and water (10.0 mL) were added, and then the resulting solid was filtered to give the title compound (424.9 mg, yield: 65.4%).

Step 26-2: Preparation of N-(6-(3-aminophenyl)-4-methylpyridin-2-yl)-5-methylthiazol-2-amine

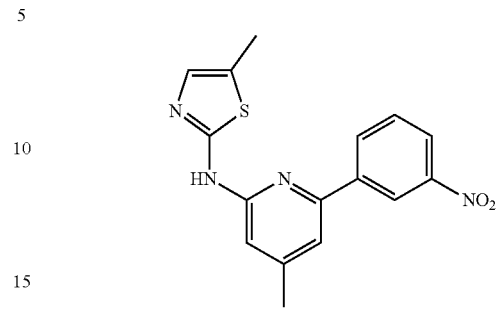

The intermediate (427.0 mg, 1 eq) obtained in step 26-1 was dissolved in 6N hydrochloric acid aqueous solution (1.1 mL, 5 eq). Water (4.0 mL), methanol (4.0 mL) and dichloromethane (4.0 mL) were added and then 10% palladium/carbon (400.0 mg) was added, and the mixture was stirred at 30~50° C. for 12 hours using a hydrogen gas balloon to complete the reaction. The reaction mixture was filtered through celite and washed with methanol (4.0 mL) and dichloromethane (4.0 mL), and then concentrated. After adjusting the pH to 9~12 using 12N-sodium hydroxide aqueous solution, ethyl acetate (2.0 mL) was added, and the solid was filtered to give the title compound (293.2 mg, yield: 75.2%).

Step 26-3: Preparation of N-(3-(4-methyl-6-((5-methylthiazol-2-yl)amino)pyridin-2-yl)phenyl)acrylamide

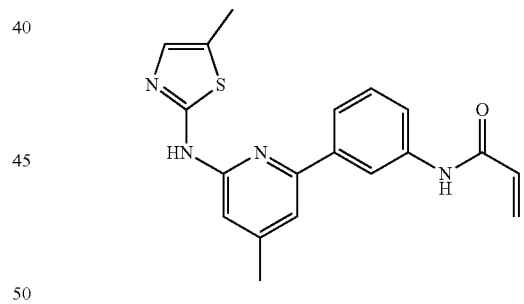

The intermediate (290.0 mg, 1 eq) obtained in step 26-2 was added to tetrahydrofuran (3.0 mL) and water (0.6 mL). Sodium bicarbonate (246.5 mg, 3.0 eq) was added thereto and then cooled to 0~10° C. Acryloyl chloride (79.5 uL, 1.0 eq) was slowly added dropwise. The mixture was stirred at 0~10° C. for 1 hour to compete the reaction. Water (6.0 mL) and dichloromethane (6.0 mL) were added and the layers were separated. The dichloromethane layer was dried over anhydrous sodium sulfate and then concentrated under reduced pressure. Ethyl acetate (1.5 mL) was added and the solid was filtered to give the title compound (180.0 mg, yield: 52.5%).

1H NMR (500 MHz, CDCl$_3$): 8.45 (s, 1H), 7.95-7.93 (d, 1H), 7.48-7.45 (m, 2H), 7.17 (s, 1H), 7.06 (s, 1H), 6.58 (s, 1H), 6.50-6.46 (d, 1H), 6.30 (m, 1H), 5.80-5.78 (d, 1H)

Example 27: Preparation of N-(3-(6-((5-cyclopropyl-1H-pyrazol-3-yl)amino)-4-(morpholinomethyl)pyridin-2-yl)phenyl)acrylamide

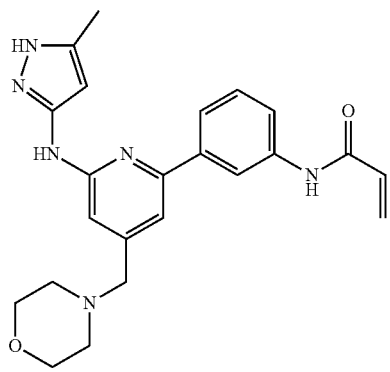

The title compound (3.8 mg, yield 50.5%) was obtained in the same manner as in Example 22, except that in step 22-4 of Example 22, t-butyl 3-amino-5-cyclopropyl-1H-pyrazole-1-carboxylate was used instead of t-butyl 3-amino-5-methyl-1H-pyrazole-1-carboxylate.

1H NMR (500 MHz, MeOD): 8.30 (s, 1H), 7.73-7.71 (d, 1H), 7.67-7.66 (d, 1H), 7.44-7.41 (t, 1H), 7.25 (s, 1H), 6.90 (s, 1H), 6.47-6.38 (m, 2H), 5.80-5.78 (d, 1H), 3.72 (t, 4H), 3.53 (s, 2H), 2.53 (t, 4H), 2.17 (q, 1H), 0.94-0.88 (m, 4H)

Example 28: Preparation of N-(3-(6-(5-cyclopropyl-1H-pyrazol-3-ylamino)-4-(morpholine-4-carbonyl)pyridin-2-yl)phenyl)acrylamide

Step 28-1: Preparation of (2-chloro-6-(3-nitrophenyl)pyridin-4-yl)(morpholino)methanone

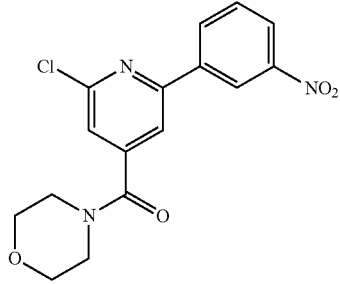 [SMILES: O=C(c1cc(Cl)nc(-c2cccc([N+](=O)[O-])c2)c1)N1CCOCC1]

The title compound (105.0 mg, yield 35.0%) was obtained in the same manner as in step 22-3 of Example 22, the intermediate obtained in step 22-1 was used instead of the intermediate obtained in step 22-2.

Step 28-2: Preparation of N-(3-(6-(5-cyclopropyl-1H-pyrazol-3-ylamino)-4-(morpholine-4-carbonyl)pyridin-2-yl)phenyl)acrylamide

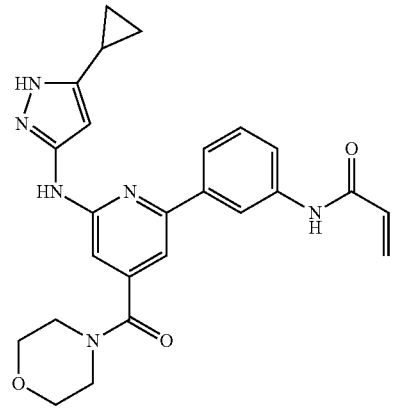 [SMILES: C=CC(=O)Nc1cccc(-c2cc(C(=O)N3CCOCC3)cc(Nc3cc(C4CC4)[nH]n3)n2)c1]

The title compound (15.2 mg, yield 40.0%) was obtained in the same manner as in steps 22-4 to 22-6 of Example 22, except that in step 22-4 of Example 22, the intermediate obtained in step 28-1 was used instead of the intermediate obtained in step 22-3.

1H NMR (500 MHz, MeOD): 8.39 (s, 1H), 7.77-7.75 (d, 1H), 7.64-7.62 (d, 1H), 7.44-7.41 (t, 1H), 7.19 (s, 1H), 6.96 (s, 1H), 6.46-6.41 (m, 2H), 6.10 (s, 1H), 5.79-5.77 (d, 1H), 3.89-3.87 (t, 4H), 3.76 (m, 2H), 3.64 (m, 2H), 1.91-1.90 (m, 1H), 0.96-0.92 (m, 2H), 0.76-0.73 (m, 2H)

Example 29: Preparation of N-(3-(6-((5-methylthiazol-2-yl)amino)-4-(morpholine-4-carbonyl)pyridin-2-yl)phenyl)acrylamide

Step 29-1: Preparation of (2-((5-methylthiazol-2-yl)amino)-6-(3-nitrophenyl)pyridin-4-yl) morpholino) methanone

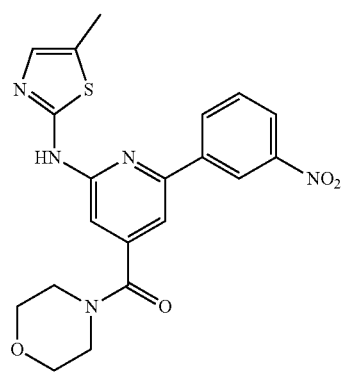 [SMILES: Cc1cnc(Nc2cc(C(=O)N3CCOCC3)cc(-c3cccc([N+](=O)[O-])c3)n2)s1]

The intermediate (200.0 mg, 1 eq) obtained in step 28-1 was dissolved in 1,4-dioxane (2.0 mL), and then palladium acetate (12.9 mg, 0.1 eq) and Xantphos (66.5 mg, 0.2 eq) were added thereto. 5-Methylthiazol-2-amine (37.7 mg, 1 eq) and cesium carbonate (562.0 g, 3 eq) were added thereto, and the mixture was reacted in a microwave reactor at 150° C. for 30 minutes. Ethyl acetate (4.0 mL) and water (4.0 mL)

were added and then the resulting solid was filtered to give the title compound (134.6 mg, yield: 55.0%).

Step 29-2: Preparation of N-(3-(6-((5-methylthiazol-2-yl)amino)-4-(morpholine-4-carbonyl)pyridin-2-yl)phenyl)acrylamide

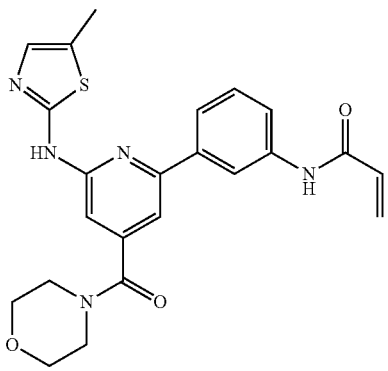 [SMILES: C=CC(=O)Nc1cccc(-c2cc(C(=O)N3CCOCC3)cc(Nc3ncc(C)s3)n2)c1]

The title compound (59.8 mg, yield: 60%) was obtained in the same manner as in steps 26-2 and 26-3 of Example 26, except that in step 26-2 of Example 26, the intermediate obtained in step 29-2 was used instead of the intermediate obtained in step 26-1.

1H NMR (500 MHz, MeOD): 8.74 (s, 1H), 7.97-7.96 (d, 1H), 7.56-7.55 (d, 1H), 7.50-7.47 (t, 1H), 7.40 (s, 1H), 7.02 (s, 1H), 6.92 (s, 1H), 6.51-6.39 (m, 2H) 5.81-5.78 (d, 1H), 3.79 (m, 4H), 3.60 (m, 2H), 3.50 (m, 2H), 2.43 (s, 3H)

Example 30: Preparation of N (3(6(5-methylthiazol-2-ylamino)-4-(morpholinomethyl)pyridin-2-yl)phenyl)acrylamide Step 30-1: Preparation of 5-methyl-N-(4-(morpholinomethyl)-6-(3-nitrophenyl)pyridin-2-yl)thiazol-2-amine

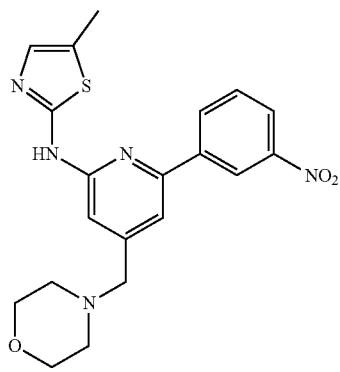 [SMILES: Cc1cnc(Nc2cc(CN3CCOCC3)cc(-c3cccc([N+](=O)[O-])c3)n2)s1]

The intermediate (200.0 mg, 1 eq) obtained in step 22-3 was dissolved in 1,4-dioxane (2.0 mL), and then palladium acetate (13.5 mg, 0.1 eq) and Xantphos (69.4 mg, 0.2 eq) were added thereto. 5-Methylthiazol-2-amine (68.5 mg, 1 eq) and cesium carbonate (586.5 g, 3 eq) were added thereto, and then the mixture was reacted in a microwave reactor at 150° C. for 30 minutes. Ethyl acetate (4.0 mL) and water (4.0 mL) were added, and the resulting solid was filtered to give the title compound (123.4 mg, yield: 50.0%).

Step 30-2: Preparation of N (3(6(5methylthiazol-2-ylamino)-4-(morpholinomethyl)pyridin-2-yl)phenyl)acrylamide

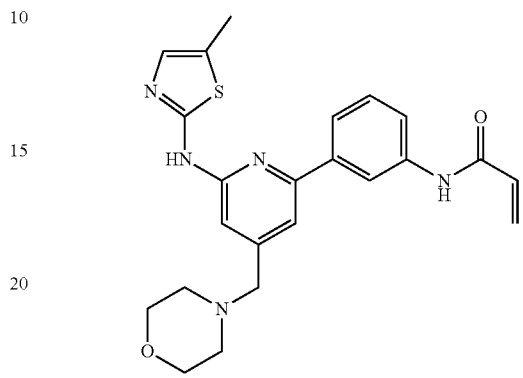

The title compound (55.5 mg, yield 60.2%) was obtained in the same manner as in steps 26-2 and 26-3 of Example 26, except that in step 26-2 of Example 26, the intermediate obtained in step 30-1 was used instead of the intermediate obtained in step 26-1.

1H NMR (500 MHz, MeOD): 8.34 (s, 1H), 7.74-7.73 (d, 1H), 7.65 (d, 1H), 7.4 (t, 1H), 7.25 (s, 1H), 6.90 (s, 1H), 6.48-6.41 (m, 2H), 6.35 (s, 1H), 5.80-5.77 (d, 1H), 3.54 (s, 2H), 2.52 (m, 4H), 2.28 (s, 3H), 1.64-1.62 (m, 4H), 1.49 (m, 2H)

Example 31: Preparation of N-(3-(6-((5-methyl-1H-pyrazol-3-yl)amino)-4-(morpholine-4-carbonyl)pyridin-2-yl)phenyl)acrylamide

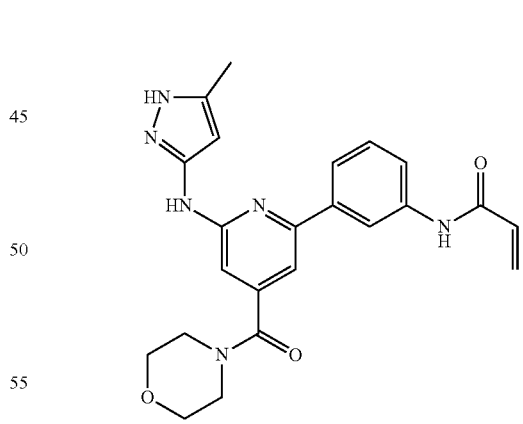

The title compound (15.5 mg, yield: 45.0%) was obtained in the same manner as in Example 28, except that in Example 28, t-butyl 3-amino-5-methyl-1H-pyrazole-1-carboxylate was used instead of t-butyl 3-amino-5-cyclopropyl-1H-pyrazole-1-carboxylate.

1H NMR (500 MHz, MeOD): 8.44 (s, 1H), 7.78-7.76 (d, 1H), 7.63-7.61 (d, 1H), 7.44-7.41 (t, 1H), 7.19 (s, 1H), 6.97 (s, 1H), 6.5-6.37 (m, 2H), 6.26 (d, 1H), 3.80 (m, 4H), 3.65 (m, 2H), 3.55 (m, 2H), 2.29 (s, 3H)

Example 32: Preparation of N-(3-(6-(5-methyl-1H-pyrazol-3-ylamino)-4-(piperidin-1-ylmethyl)pyridin-2-yl)phenyl)acrylamide

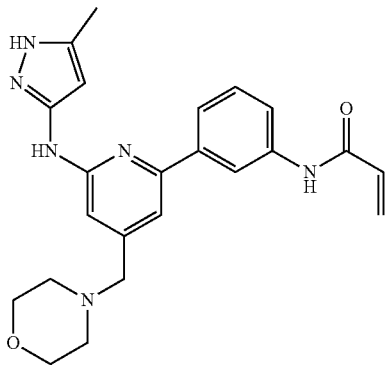

The title compound (15.0 mg, yield: 50.0%) was obtained in the same manner as in Example 22, except that in step 22-1 of Example 22, piperidine was used instead of morpholine.

1H NMR (500 MHz, MeOD): 8.44 (s, 1H), 7.78-7.76 (d, 1H), 7.63-7.61 (d, 1H), 7.44-7.41 (t, 1H), 7.19 (s, 1H), 6.97 (s, 1H), 6.50-6.37 (m, 2H), 6.37 (s, 1H), 5.79-5.77 (d, 1H), 3.80 (m, 4H), 3.65 (m, 2H), 3.45 (m, 2H), 3.27 (s, 3H)

Example 33: Preparation of 2-((6-(3-acrylamidophenyl)-4-(morpholinomethyl)pyridin-2-yl)amino)-N-(2-chloro-6-methylphenyl)thiazole-5-carboxamide

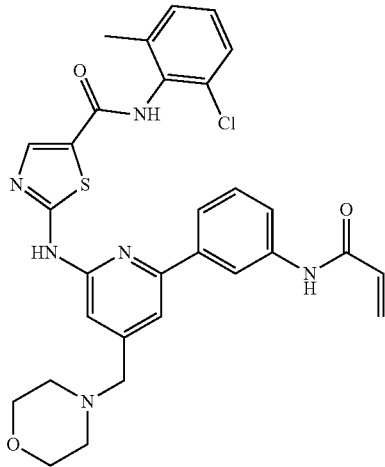 [SMILES: C=CC(=O)Nc1cccc(-c2cc(CN3CCOCC3)cc(Nc3ncc(C(=O)Nc4c(C)cccc4Cl)s3)n2)c1]

The title compound (12.0 mg, yield: 45.0%) was obtained in the same manner as in Example 30, except that in step 30-1 of Example 30, 2-amino-N-(2-chloro-6-methylphenyl)thiazole-5-carboxamide was used instead of 5-methylthiazol-2-amine.

1H NMR (500 MHz, MeOD): 8.84 (s, 1H), 8.19 (s, 1H), 7.88-7.87 (d, 1H), 7.57 (s, 1H), 7.55 (d, 1H), 7.48-7.45 (t, 1H), 7.35-7.34 (d, 1H), 7.26-7.21 (m, 2H), 7.07 (s, 1H), 6.32 (m, 1H), 6.03-6.00 (d, 1H), 5.48-5.45 (d, 1H), 3.75-3.73 (m, 4H), 3.26 (s, 2H), 2.54 (m, 4H), 2.32 (s, 3H)

Example 34: Preparation of N-(3-(4-((2,6-dimethylmorpholino)methyl)-6-(5-methylthiazol-2-yl)amino)pyridin-2-yl)phenyl)acrylamide

Step 34-1: Preparation of 4-((2,6-dichloropyridin-4-yl)methyl)-2,6-dimethylmorpholine

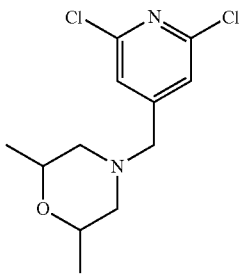 [SMILES: CC1CN(Cc2cc(Cl)nc(Cl)c2)CC(C)O1]

The title compound (429.7 mg, yield: 90.0%) was obtained in the same manner as in steps 22-1 and 22-2 of Example 22, except that in step 22-1 of Example 22, dimethylmorpholine was used instead of morpholine.

Step 34-2: Preparation of 4-((2-chloro-6-(3-nitrophenyl)pyridin-4-yl)methyl)-2,6-dimethylmorpholine

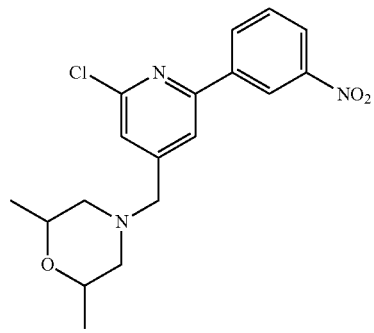 [SMILES: CC1CN(Cc2cc(Cl)nc(-c3cccc([N+](=O)[O-])c3)c2)CC(C)O1]

The title compound (131.5 mg, yield: 25.0%) was obtained in the same manner as in step 22-3 of Example 22, except that in step 22-3 of Example 22, the intermediate obtained in step 34-1 was used instead of the intermediate obtained in step 22-2.

Step 34-3: Preparation of N-(3-(4-((2,6-dimethylmorpholino)methyl)-6-(5-methylthiazol-2-yl)amino)pyridin-2-yl)phenyl)acrylamide

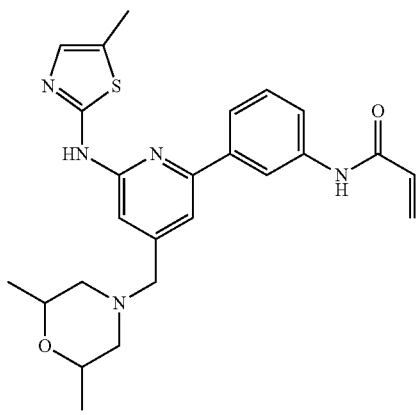 [SMILES: C=CC(=O)Nc1cccc(-c2cc(CN3CC(C)OC(C)C3)cc(Nc3ncc(C)s3)n2)c1]

The title compound (10.0 mg, yield: 40.0%) was obtained in the same manner as in Example 30, except that in step 30-1 of Example 30, 4-((2-chloro-6-(3-nitrophenyl)pyridin-4-yl)methyl)-2,6-dimethylmorpholine was used instead of the intermediate obtained in step 22-3.

1H NMR (500 MHz, CDCl$_3$): 8.49 (s, 1H), 7.97-7.96 (d, 1H), 7.58 (d, 1H), 7.50-7.47 (t, 1H), 7.32 (s, 1H), 7.09 (s, 1H), 6.82 (s, 1H), 6.50-6.47 (d, 1H), 6.33-6.27 (m, 1H), 5.82-5.20 (d, 1H), 3.75-3.74 (s, 2H), 2.73-2.71 (d, 2H), 2.44 (s, 3H), 1.83-1.79 (t, 2H), 1.16 (s, 3H), 1.14 (s, 3H)

Example 35: Preparation of N-(3-(4-(dimethylamino)-6-((5-methylthiazol-2-yl)amino)pyridin-2-yl)phenyl)acrylamide Step 35-1: Preparation of 2-chloro-N,N-dimethyl-6-(3-nitrophenyl)pyridin-4-amine

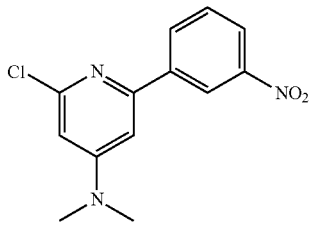 [SMILES: CN(C)c1cc(Cl)nc(-c2cccc([N+](=O)[O-])c2)c1]

The title compound (131.5 mg, yield: 28.0%) was obtained in the same manner as in step 22-3 of Example 22, except that in step 22-3 of Example 22, 2,6-dichloro-N,N-dimethylpyridin-4-amine was used instead of the intermediate obtained in step 22-2.

Step 35-2: Preparation of N-(3-(4-(dimethylamino)-6-((5-methylthiazol-2-yl)amino)pyridin-2-yl)phenyl)acrylamide

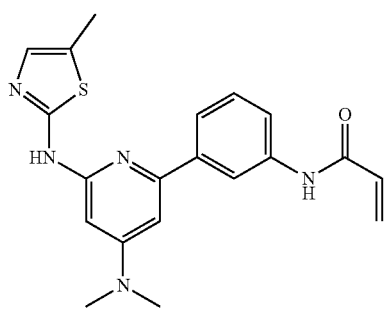 [SMILES: C=CC(=O)Nc1cccc(-c2cc(N(C)C)cc(Nc3ncc(C)s3)n2)c1]

The title compound (8.5 mg, yield: 50.0%) was obtained in the same manner as in Example 30, except that in step 30-1 of Example 30, the intermediate obtained in step 35-1 was used instead of the intermediate obtained in step 22-3.

1H NMR (500 MHz, CDCl$_3$): 8.26 (s, 1H), 7.85 (d, 2H), 7.45 (m, 2H), 7.05 (s, 1H), 6.70 (s, 1H), 6.48-6.44 (d, 1H), 6.33 (s, 1H), 6.31-6.29 (m, 1H), 5.80-5.78 (d, 1), 3.09 (s, 6H), 2.35 (s, 3H)

Example 36: Preparation of N-(3-(6-((5-methylthiazol-2-yl)amino)-4-morpholinopyridin-2-yl)phenyl)acrylamide Step 36-1: Preparation of 4-(2-chloro-6-(3-nitrophenyl)pyridin-4-yl)morpholine

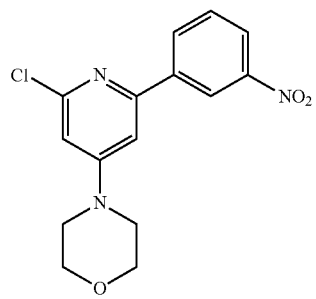 [SMILES: O=[N+]([O-])c1cccc(-c2cc(N3CCOCC3)cc(Cl)n2)c1]

The title compound (210.0 mg, yield: 28.0%) was obtained in the same manner as in step 22-3 of Example 22, except that in step 22-3 of Example 22, 4-(2,6-dichloropyridin-4-yl)morpholine was used instead of the intermediate obtained in step 22-2.

Step 36-2: Preparation of N-(3-(6-((5-methylthiazol-2-yl)amino)-4-morpholinopyridin-2-yl)phenyl)acrylamide

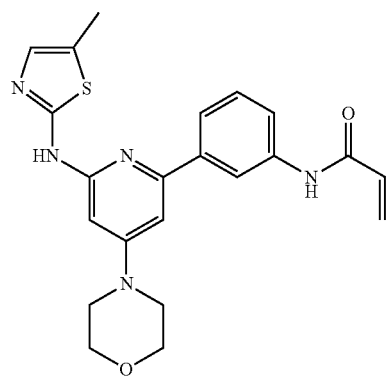 [SMILES: C=CC(=O)Nc1cccc(-c2cc(N3CCOCC3)cc(Nc3ncc(C)s3)n2)c1]

The title compound (10.5 mg, yield: 45.0%) was obtained in the same manner as in Example 30, except that in step 30-1 of Example 30, the intermediate obtained in step 36-1 was used instead of the intermediate obtained in step 22-3.

1H NMR (500 MHz, MeOD): 8.46 (s, 1H), 7.86-7.85 (d, 1H), 7.61-7.59 (d, 1H), 7.44-7.41 (t, 1H), 7.00 (s, 1H), 6.67 (s, 1H), 6.50-6.37 (m, 2H), 5.79-5.77 (d, 1H), 3.85 (m, 4H), 3.50 (m, 4H), 3.24 (s, 3H)

Example 37: Preparation of N-(3-(4-((4-methylpiperazin-1-yl)methyl)-6-(5-methylthiazol-2-ylamino)pyridin-2-yl)phenyl)acrylamide

Step 37-1: Preparation of 1-((2,6-dichloropyridin-4-yl)methyl)-4-methylpiperazine

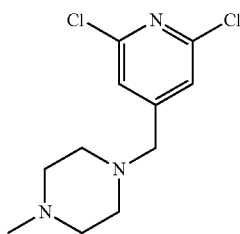 [SMILES: CN1CCN(Cc2cc(Cl)nc(Cl)c2)CC1]

The title compound (350.0 mg, yield: 80.0%) was obtained in the same manner as in steps 22-1 and 22-2, except that in step 22-1 of Example 22, 1-methylpiperazine was used instead of morpholine.

Step 37-2: Preparation of 1-((2-chloro-6-(3-nitrophenyl)pyridin-4-yl)methyl)-4-methylpiperazine

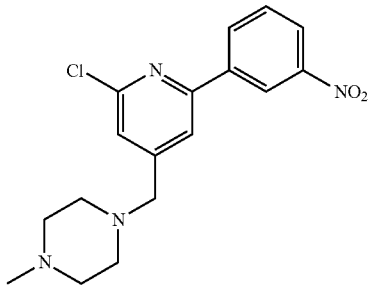 [SMILES: CN1CCN(Cc2cc(Cl)nc(-c3cccc([N+](=O)[O-])c3)c2)CC1]

The title compound (140.6 mg, yield: 30.0%) was obtained in the same manner as in step 22-3 of Example 22, except that in step 22-3 of Example 22, the intermediate obtained in step 37-1 was used instead of the intermediate obtained in step 22-2.

Step 37-3: Preparation of N-(3-(4-((4-methylpiperazin-1-yl)methyl)-6-(5-methylthiazol-2-ylamino)pyridin-2-yl)phenyl)acrylamide

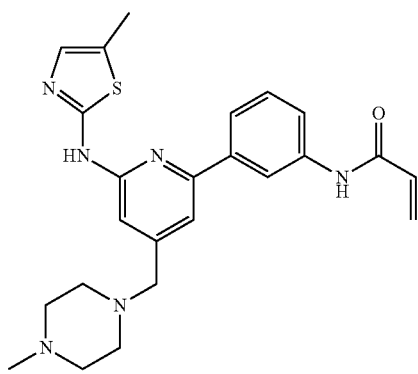 [SMILES: C=CC(=O)Nc1cccc(-c2cc(CN3CCN(C)CC3)cc(Nc3ncc(C)s3)n2)c1]

The title compound (15.0 mg, yield: 45.0%) was obtained in the same manner as in Example 30, except that in step 30-1 of Example 30, the intermediate obtained in step 37-2 was used instead of the intermediate obtained in step 22-3.

1H NMR (500 MHz, MeOD): 8.68 (s, 1H), 7.95-7.93 (d, 1H), 7.55 (d, 1H), 7.45 (t, 1H), 7.40 (s, 1H), 6.99 (s, 1H), 6.90 (s, 1H), 6.52-6.47 (m, 2H), 5.80 (d, 1H), 3.58 (s, 2H), 2.6 (m, 8H), 2.41 (s, 3H), 2.35 (s, 3H)

Example 38: Preparation of (E)-N-(3-(4-benzyl-6-(5-methyl-1H-pyrazol-3-ylamino)pyridin-2-yl)phenyl)but-2-enamide

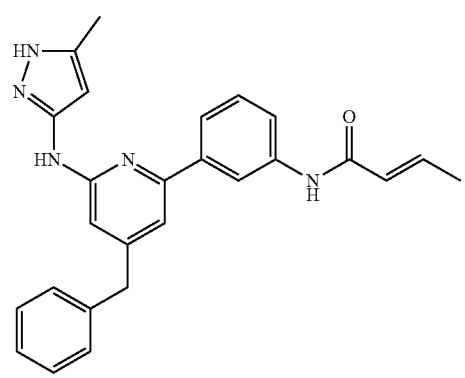 [SMILES: C/C=C/C(=O)Nc1cccc(-c2cc(Cc3ccccc3)cc(Nc3cc(C)[nH]n3)n2)c1]

The title compound (15.0 mg, yield: 35.0%) was obtained in the same manner as in Example 2, except that in step 2-4 of Example 2, (E)-but-2-enoyl chloride was used instead of acryloyl chloride.

1H NMR (500 MHz, MeOD): 8.22 (s, 1H), 7.65-7.62 (m, 2H), 7.40-7.37 (t, 1H), 7.31-7.26 (m, 5H), 7.22-7.19 (t, 1H), 7.08 (s, 1H), 6.97-6.93 (m, 1H), 6.69 (s, 1H), 6.16 (d, 1H), 3.95 (s, 2H), 2.25 (s, 3H), 1.94-1.91 (d, 3H)

Example 39: Preparation of N-(3-(6-(5-methyl-1,3,4-thiadiazol-2-ylamino)-4-(morpholinomethyl)pyridin-2-yl)phenyl)acrylamide

Step 39-1: Preparation of (2,6-dichloropyridin-4-yl)(morpholino)methanone

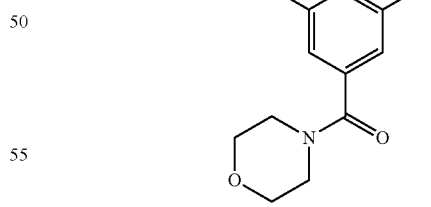

After 1,1'-carbonyldiimidazole (5.0 g, 1.2 eq) was dissolved in dimethylformamide (30.0 mL), 2,6-dichloroisonicotinic acid (5.0 g, 1.0 eq) was added thereto and the mixture was stirred at room temperature for 1 hour. Morpholine (2.7 mL, 1.2 eq) was added thereto, and the mixture was stirred at room temperature for 2 hours. Water was added and the mixture was extracted with ethyl acetate. The separated organic layer was dried over anhydrous sodium sulfate and then concentrated under reduced pressure. The resulting residue was slurried with dichloromethane and filtered to give the title compound (white solid, 5.5 g, yield: 81%).

Step 39-2: Preparation of 4-((2,6-dichloropyridin-4-yl)methyl)morpholine

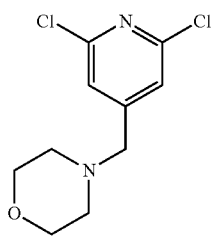 [SMILES: Clc1cc(CN2CCOCC2)cc(Cl)n1]

The intermediate (5.5 g, 1.0 eq) obtained in step 39-1 was dissolved in dichloromethane (60.0 mL), and then 0.9 M borane tetrahydrofuran solution (87.0 mL, 3.7 eq) was added thereto. The mixture was stirred at room temperature for 72 hours. Water was added and the mixture was extracted with dichloromethane. The separated organic layer was dried over anhydrous sodium sulfate and then concentrated under reduced pressure. The resulting residue was purified by column chromatography (ethyl acetate:hexane=1:1) to give the title compound (white solid, 3.4 g, yield: 66%).

Step 39-3: Preparation of N-(6-chloro-4-(morpholinomethyl)pyridin-2-yl)-5-methyl-1,3,4-thiadiazol-2-amine

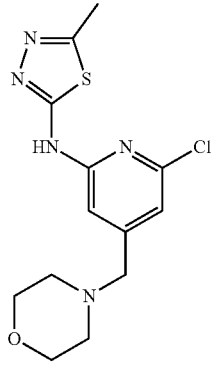 [SMILES: Cc1nnc(Nc2cc(CN3CCOCC3)cc(Cl)n2)s1]

After the intermediate (100.0 mg, 1.0 eq) obtained in step 39-2 was dissolved in 1,4-dioxane (10.0 mL), sodium carbonate (127.2 mg, 3.0 eq), tris(dibenzylideneacetone)dipalladium(0) (73.3 mg, 0.2 eq), Xantphos (92.6 mg, 0.4 eq) and 5-methyl-1,3,4-thiadiazol-2-amine (46.6 mg, 1.0 eq) were added sequentially. The mixture was stirred at 140° C. for 12 hours. Water was added and the mixture was extracted with dichloromethane. The separated organic layer was dried over anhydrous sodium sulfate and then concentrated under reduced pressure. The resulting residue was slurried in dichloromethane and then filtered to give the title compound (white solid, 24.1 mg, yield: 19%).

Step 39-4: Preparation of (3-acrylamidophenyl)boronic acid

After (3-aminophenyl)boronic acid (10.0 g, 1.0 eq) was dissolved in dichloromethane (80.0 mL), diisopropylethylamine (11.2 mL, 1.0 eq) and acryloyl chloride (5.24 mL, 10 eq) were added sequentially at 0~5° C. The mixture was stirred at 0~5° C. for 1 hour. Water was added and the mixture was extracted with dichloromethane. The separated organic layer was dried over anhydrous sodium sulfate and then concentrated under reduced pressure. The resulting residue was purified by column chromatography (dichloromethane:methanol=10:1) to give the title compound (yellow solid, 5.0 g, yield: 41%).

Step 39-5: Preparation of N-(3-(6-(5-methyl-1,3,4-thiadiazol-2-ylamino)-4-(morpholinomethyl)pyridin-2-yl)phenyl)acrylamide

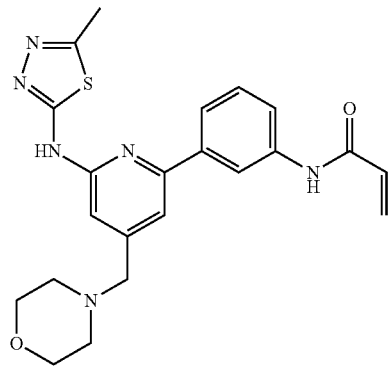

After the intermediate (20.0 mg, 1.0 eq) obtained in step 39-3 was dissolved in 1,4-dioxane (3.0 mL), the intermediate obtained in step 39-4 (11.7 mg, 1.0 eq), sodium carbonate (25.4 mg, 4.0 eq), water (1.0 mL) and tetrakis(triphenylphosphine)palladium(0) (6.9 mg, 0.1 eq) were added sequentially. The mixture was stirred at 140° C. for 12 hours. Water was added and the mixture was extracted with dichloromethane. The separated organic layer was dried over anhydrous sodium sulfate and then concentrated under reduced pressure. The resulting residue was purified by column chromatography (ethyl acetate:hexane=4:1) to give the title compound (yellow solid, 3.3 mg, yield: 13%).

1H NMR (500 MHz, MeOD): 8.78 (s, 1H), 7.85 (d, 1H), 7.50-7.43 (m, 3H), 7.01 (s, 1H), 6.51 (m, 1H), 6.42 (m, 1H), 5.80 (d, 1H), 3.73 (m, 4H), 3.60 (s, 2H), 2.70 (s, 3H), 2.50 (m, 4H)

Example 40: Preparation of N-(3-(6-((5-methyl-isoxazol-3-ylamino)-4-(morpholino)methyl)pyridin-2-yl)phenyl)acrylamide

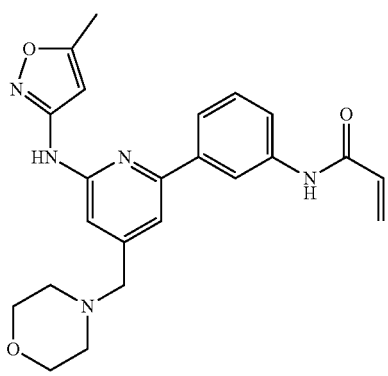

The title compound (8.6 mg, yield: 27%) was obtained in the same manner as in Example 39, except that in step 39-3 of Example 39, 5-methylisoxazol-3-amine was used instead of 5-methyl-1,3,4-thiadiazol-2-amine.

1H NMR (500 MHz, MeOD): 8.28 (s, 1H), 7.81 (d, 1H), 7.68 (m, 2H), 7.51 (t, 1H), 7.34 (s, 1H), 6.46 (m, 1H), 6.37 (d, 1H), 5.79 (d, 1H), 3.73 (m, 4H), 3.65 (s, 2H), 2.54 (m, 4H), 2.26 (s, 3H)

Example 41: Preparation of N-(3-(6-((5-methyl-1,3,4-oxadiazol-2-yl)amino)-4-(morpholinomethyl)pyridin-2-yl)phenyl)acrylamide

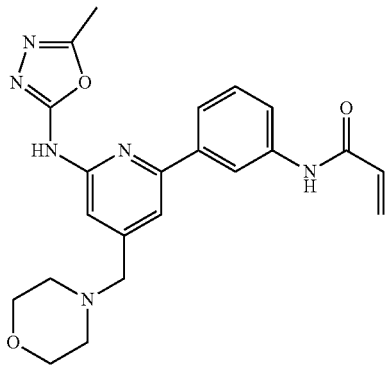 [SMILES: C=CC(=O)Nc1cccc(-c2cc(CN3CCOCC3)cc(Nc3nnc(C)s3)n2)c1]

The title compound (16.0 mg, yield: 21%) was obtained in the same manner as in Example 39, except that in step 39-3 of Example 39, 5-methyl-1,3,4-oxadiazol-2-amine was used instead of 5-methyl-1,3,4-thiadiazol-2-amine.

1H NMR (500 MHz, MeOD): 8.40 (s, 1H), 7.82 (d, 1H), 7.78 (m, 1H), 7.53 (d, 1H), 7.43 (s, 1H), 7.36 (t, 1H), 6.43 (m, 1H), 6.38 (d, 1H), 5.79 (d, 1H), 3.73 (m, 4H), 3.62 (s, 2H), 2.53 (m, 4H), 2.49 (s, 3H)

Example 42: Preparation of N-(6-(3-acrylamidophenyl)-4-(morpholinomethyl)pyridin-2-yl)cyclopropanecarboxamide

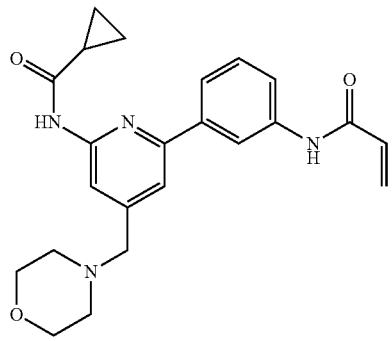 [SMILES: C=CC(=O)Nc1cccc(-c2cc(CN3CCOCC3)cc(NC(=O)C3CC3)n2)c1]

The title compound (22.1 mg, yield: 20%) was obtained in the same manner as in Example 39, except that in step 39-3 of Example 39, cyclopropanecarboxamide was used instead of 5-methyl-1,3,4-thiadiazol-2-amine.

1H NMR (500 MHz, MeOD): 8.41 (s, 1H), 8.05 (s, 1H), 7.81 (d, 1H), 7.59 (m, 2H), 7.42 (t, 1H), 6.46 (m, 1H), 6.38 (d, 1H), 5.79 (d, 1H), 3.72 (m, 4H), 3.59 (s, 2H), 2.51 (m, 4H), 1.92 (m, 1H), 1.00 (m, 2H), 0.92 (m, 2H)

Example 43: Preparation of N-(3-(4-((4-(2-hydroxyethyl)piperazin-1-yl)methyl)-6-(5-methylthiazol-2-ylamino)pyridin-2-yl)phenyl)acrylamide

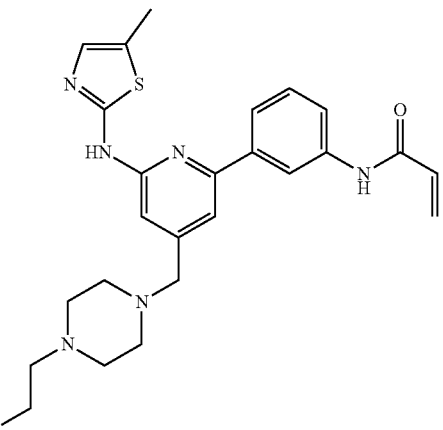

The title compound (10.0 mg, yield: 50.0%) was obtained in the same manner as in Example 37, except that in step 37-1 of Example 37, 2-(pyrerazin-1-yl)ethan-1-ol was used instead of 1-methylpiperazine.

1H NMR (500 MHz, MeOD): 8.67 (s, 1H), 7.96-7.94 (d, 1H), 7.56-7.55 (d, 1H), 7.48-7.45 (t, 1H), 7.43 (s, 1H), 6.99 (s, 1H), 6.92 (s, 1H), 6.52-6.39 (m, 1H), 5.81-5.79 (d, 1H), 4.59 (s, 2H), 3.68 (t, 2H), 2.6-2.8 (m, 8H), 2.42 (s, 3H)

Example 44: Preparation of N-(3-(6-((1,2,4-thiadiazol-5-yl)amino)-4-(morpholinomethyl)pyridin-2-yl)phenyl)acrylamide

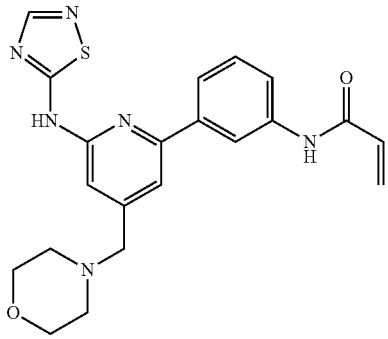 [SMILES: C=CC(=O)Nc1cccc(-c2cc(CN3CCOCC3)cc(Nc3ncns3)n2)c1]

The title compound (5.3 mg, yield: 9%) was obtained in the same manner as in Example 39, except that in step 39-3 of Example 39, 1,2,4-thiadiazol-5-amine was used instead of 5-methyl-1,3,4-thiadiazol-2-amine.

1H NMR (500 MHz, MeOD): 8.49 (s, 1H), 8.23 (s, 1H), 7.91 (d, 1H), 7.70 (d, 1H), 7.51 (m, 2H), 7.13 (s, 1H), 6.50 (m, 1H), 6.42 (d, 1H), 5.80 (d, 1H), 3.74 (m, 4H), 3.64 (s, 2H), 2.53 (m, 4H)

Example 45: Preparation of N-(3-(4-((4-cyclopropylpiperazin-1-yl)methyl)-6-((5-methylthiazol-2-yl)amino)pyridin-2-yl)phenyl)acrylamide

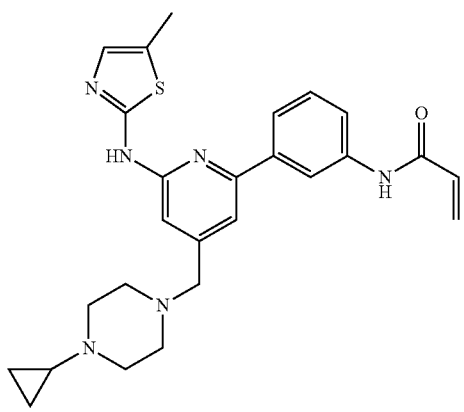 [SMILES: C=CC(=O)Nc1cccc(-c2cc(CN3CCN(C4CC4)CC3)cc(Nc3ncc(C)s3)n2)c1]

The title compound (13.0 mg, yield: 52.0%) was obtained in the same manner as in Example 37, except that in step 37-1 of Example 37, 1-cyclopropylpiperazine was used instead of 1-methylpiperazine.

1H NMR (500 MHz, CDCl$_3$): 8.44 (s, 1H), 7.97-7.96 (d, 1H), 7.62 (d, 1H), 7.50-7.47 (t, 1H), 7.29 (s, 1H), 7.14 (s, 1H), 6.81 (s, 1H), 6.50-6.47 (d, 1H), 6.33-6.27 (m, 1H), 5.82-5.80 (d, 1H), 3.52 (s, 3H), 2.69 (m, 4H), 2.50 (m, 4H), 2.46 (s, 3H), 0.80 (m, 1H), 0.45-0.44 (m, 2H), 0.41-0.40 (m, 2H)

Example 46: Preparation of N-(3-(4-(((2S,6R)-2,6-dimethylmorpholino)methyl)-6-(5-methylthiazol-2-ylamino)pyridin-2-yl)phenyl)acrylamide

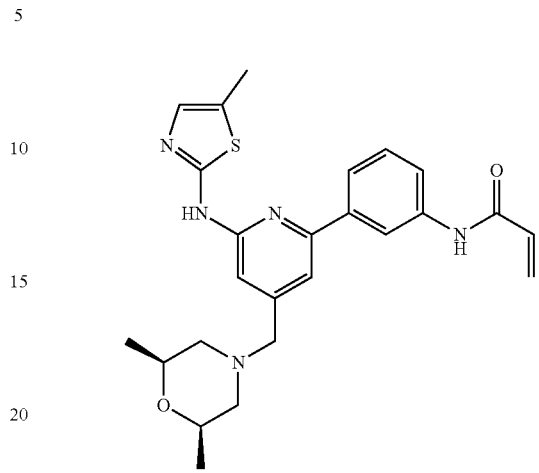

The title compound (12.0 mg, yield: 45.0%) was obtained in the same manner as in Example 37, except that in step 37-1 of Example 37, (2S,6R)-2,6-dimethylmorpholine was used instead of 1-methylpiperazine.

1H NMR (500 MHz, CDCl$_3$): 8.48 (s, 1H), 7.98-7.96 (d, 1H), 7.58 (d, 1H), 7.50-7.49 (t, 1H), 7.32 (s, 1H), 7.09 (s, 1H), 6.81 (s, 1H), 6.50-6.47 (d, 1H), 6.30 (m, 1H), 5.82-5.80 (d, 1H), 3.75-3.72 (m, 2H), 3.49 (s, 2H), 2.74-2.72 (d, 2H), 2.45 (s, 3H), 1.83-1.79 (t, 2H), 1.16-1.13 (d, 6H)

Example 47: Preparation of N-(3-(6-((5-methylthiazol-2-yl)amino)-4-(pyrrolidin-1-ylmethyl)pyridin-2-yl)phenyl)acrylamide

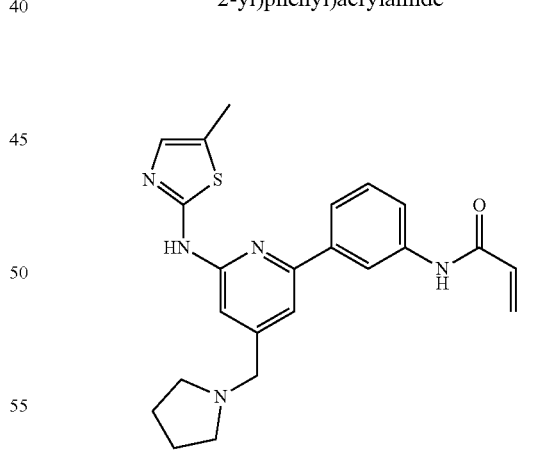

The title compound (18.0 mg, yield: 40.0%) was obtained in the same manner as in Example 37, except that in step 37-1 of Example 37, pyrrolidine was used instead of 1-methylpiperazine.

1H NMR (500 MHz, CDCl$_3$): 8.43 (s, 1H), 7.96-7.95 (d, 1H), 7.49-7.46 (m, 2H), 7.38 (s, 1H), 7.01 (s, 1H), 6.81 (s, 1H), 6.49-6.46 (d, 1H), 6.3 (m, 1H), 5.81-5.79 (d, 1H)

Example 48: Preparation of N-(3-(6-((5-methylthiazol-2-yl)amino)-4-((4-propylpiperazin-1-yl)methyl)pyridin-2-yl)phenyl)acrylamide

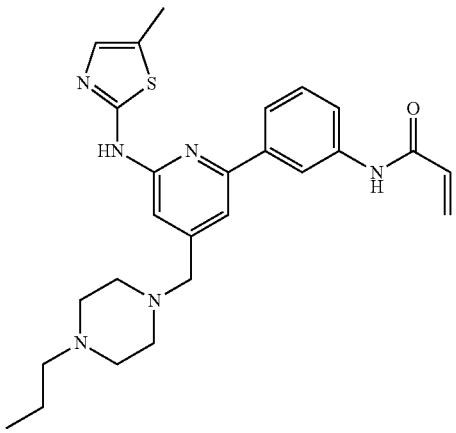 [SMILES: C=CC(=O)Nc1cccc(-c2cc(CN3CCN(CCC)CC3)cc(Nc3ncc(C)s3)n2)c1]

The title compound (8.0 mg, yield: 35.0%) was obtained in the same manner as in Example 37, that in step 37-1 of Example 37, 1-propylpiperazine was used instead of 1-methylpiperazine.

1H NMR (500 MHz, CDCl$_3$): 8.43 (s, 1H), 7.97-7.95 (d, 1H), 7.64-7.62 (m, 2H), 7.49-7.45 (t, 1H), 7.17 (s, 1H), 6.87 (s, 1H), 6.50-6.46 (d, 1H), 6.35-6.29 (1H), 5.81-5.78 (d, 1H), 2.54 (m. 4H), 2.34-2.31 (t, 2H), 1.79 (4H), 1.54-1.49 (m, 4H), 0.91-0.88 (t, 3H)

Example 49: Preparation of N-(3-(4-((4-(2-methoxyethyl)piperazin-1-yl)methyl)-6-(5-methylthiazol-2-ylamino)pyridin-2-yl)phenyl)acrylamide

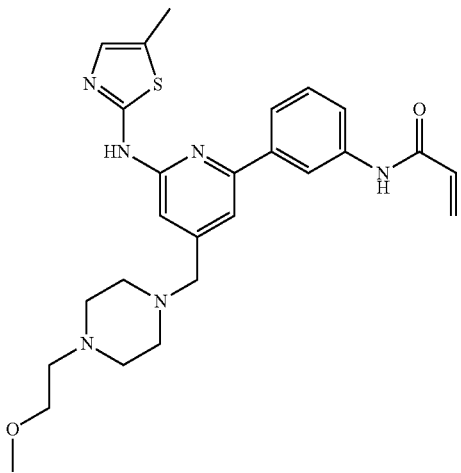 [SMILES: C=CC(=O)Nc1cccc(-c2cc(CN3CCN(CCOC)CC3)cc(Nc3ncc(C)s3)n2)c1]

The title compound (6.8 mg, yield: 40.0%) was obtained in the same manner as in Example 37, except that in step 37-1 of Example 37, 1-(2-methoxyethyl) piperazine was used instead of 1-methylpiperazine.

1H NMR (500 MHz, CDCl$_3$): 8.41 (s, 1H), 7.96-7.94 (d, 1H), 7.76 (d, 1H), 7.47-7.43 (t, 1H), 7.21 (s, 1H), 6.49-6.46 (d, 1H), 6.46-6.30 (m, 1H), 5.79-5.77 (d, 1H), 3.52-3.49 (t, 2H), 3.48 (s, 1H), 3.34 (s, 3H), 2.60-2.59 (t, 2H), 2.54 (m, 4H), 2.36 (s, 3H)

Example 50: Preparation of N (3(6(5methylthiazol-2-ylamino)-4-((4-(2,2,2-trifluoroethyl)piperazin-1-yl)methyl)pyridin-2-yl)phenyl)acrylamide

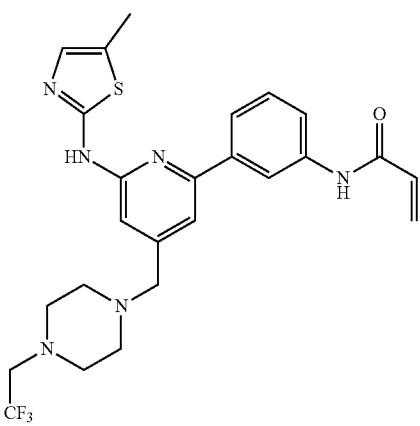 [SMILES: C=CC(=O)Nc1cccc(-c2cc(CN3CCN(CC(F)(F)F)CC3)cc(Nc3ncc(C)s3)n2)c1]

The title compound (10.0 mg, yield: 40.0%) was obtained in the same manner as in Example 37, except that in step 37-1 of Example 37, 1-(2,2,2-trifluoroethyl)piperazine was used instead of 1-methylpiperazine.

1H NMR (500 MHz, DMSO): 8.63 (s, 1H), 7.87-7.85 (d, 1H), 7.64-7.62 (d, 1H), 7.47-7.44 (t, 1H), 7.30 (s, 1H), 7.03 (s, 1H), 6.94 (s, 1H), 6.50-6.45 (m, 1H), 6.30-6.26 (d, 1H), 5.7-5.73 (m, 1H), 3.49 (s, 2H), 3.16-3.14 (m, 2H), 2.64 (m, 4H), 2.42 (m, 4H), 2.36 (s, 3H)

Example 51: Preparation of N-(3-(4-(morpholinomethyl)-6-((5-(trifluoromethyl)thiazol-2-ylamino)pyridin-2-yl)phenyl)acrylamide

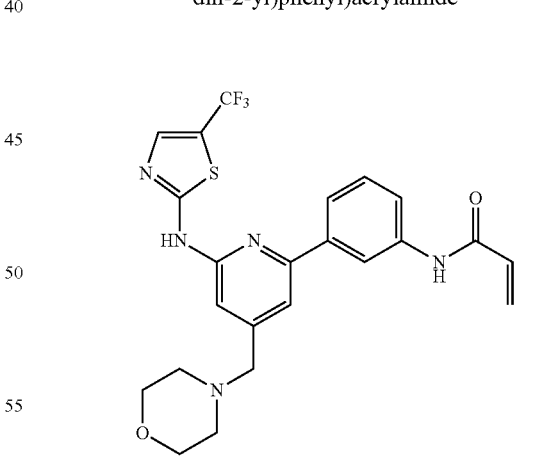

The title compound (7.0 mg, yield: 42.0%) was obtained in the same manner as in Example 30, except that in step 30-1 of Example 30, 5-(trifluoromethyl) thiazol-2-amine was used instead of 5-methylthiazol-2-amine.

1H NMR (500 MHz, MeOD): 8.53 (s, 1H), 7.89-7.88 (d, 1H), 7.74 (s, 1H), 7.58-7.52 (d, 1H), 7.50-7.46 (t, 1H), 7.42 (s, 1H), 6.86 (s, 1H), 6.50-6.47 (d, 1H), 3.31-3.25 (m, 1H), 5.83-5.81 (d, 1H), 3.75-3.74 (m, 4H), 3.62 (s, 2H), 2.50 (m, 4H).

Example 52: Preparation of N-(4-fluoro-3-(6-(5-methylthiazol-2-yl)amino)-4-(morpholinomethyl)pyridin-2-yl)phenyl)acrylamide

Step 52-1: Preparation of 4-((2-chloro-6-(2-fluoro-5-nitrophenyl)pyridin-4-yl)methyl)morpholine

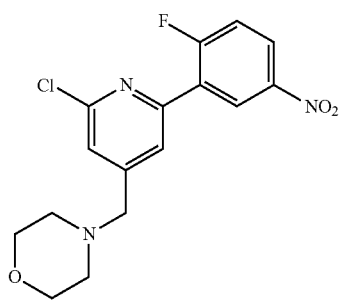 [SMILES: O=[N+]([O-])c1ccc(F)c(-c2cc(CN3CCOCC3)cc(Cl)n2)c1]

The title compound (150.0 mg, yield 25.0%) was obtained in the same manner as in step 22-3 of Example 22, except that in step 22-3 of Example 22, (2-fluoro-5-nitrophenyl) boronic acid was used instead of 3-nitrophenyl boronic acid.

Step 52-2: Preparation of N-(4-fluoro-3-(6-(5-methylthiazol-2-yl)amino)-4-(morpholinomethyl)pyridin-2-yl)phenyl)acrylamide

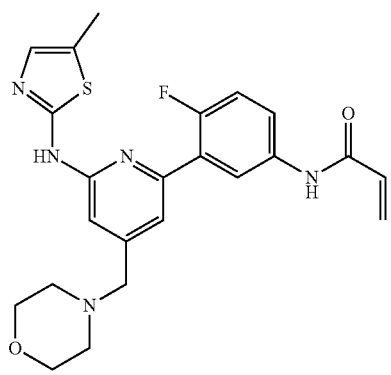 [SMILES: C=CC(=O)Nc1ccc(F)c(-c2cc(CN3CCOCC3)cc(Nc3ncc(C)s3)n2)c1]

The title compound (25.0 mg, yield: 35.0%) was obtained in the same manner as in Example 30, except that in step 30-1 of Example 30, the intermediate obtained in Step 52-1 was used instead of the intermediate obtained in Step 22-3.

1H NMR (500 MHz, DMSO): 11.06 (s, 1H), 10.29 (s, 1H), 8.66-8.64 (m, 1H), 7.62-7.61 (m, 1H), 7.32-7.28 (m, 2H), 7.02 (s, 1H), 6.99 (s, 1H), 6.48-6.35 (m, 1H), 6.29-6.25 (d, 1H), 5.77-5.75 (d, 1H), 3.59-3.58 (m, 4H), 3.49 (s, 2H), 2.39 (m, 4H), 2.31 (s, 3H)

Example 53: Preparation of N-(3-(4-((4-ethylpiperazin-1-yl)methyl)-6-(5-methylthiazol-2-yl)amino)pyridin-2-yl)phenylacrylamide

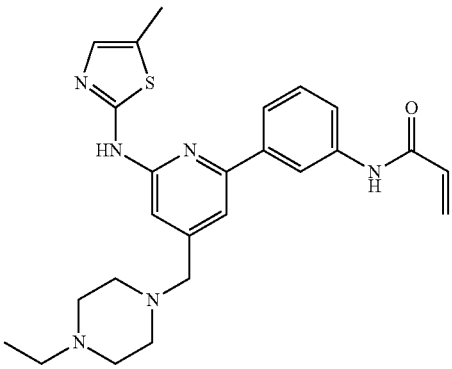 [SMILES: C=CC(=O)Nc1cccc(-c2cc(CN3CCN(CC)CC3)cc(Nc3ncc(C)s3)n2)c1]

The title compound (7.0 mg, yield 38.0%) was obtained in the same manner as in Example 37, except that in step 37-1 of Example 37, 1-ethylpiperazine was used instead of 1-methylpiperazine.

1H NMR (500 MHz, CDCl$_3$): 8.45 (s, 1H), 7.96-7.95 (d, 1H), 7.67 (s, 1H), 7.65-7.63 (d, 1H), 7.48-7.45 (t, 1H), 7.16 (s, 1H), 6.90 (s, 1H), 6.50-6.46 (d, 1H), 6.35-6.30 (m, 1H), 5.80-5.78 (d, 1H), 3.50 (s, 2H), 2.50 (m, 8H), 2.39 (q, 2H), 2.37 (s, 3H), 1.11-1.08 (t, 3H)

Example 54: Preparation of N-(3-(4-((4-isopropylpiperazin-1-yl)methyl)-6-(5-methylthiazol-2-yl)amino)pyridin-2-yl)phenyl)acrylamide

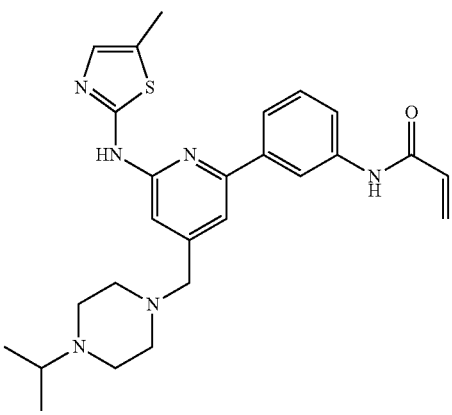 [SMILES: C=CC(=O)Nc1cccc(-c2cc(CN3CCN(C(C)C)CC3)cc(Nc3ncc(C)s3)n2)c1]

The title compound (15.0 mg, yield 40.0%) was obtained in the same manner as in Example 37, except that in step 37-1 of Example 37, 1-isopropylpiperazine was used instead of 1-methylpiperazine.

1H NMR (500 MHz, CDCl$_3$): 8.844 (s, 1H), 7.97-7.95 (d, 1H), 7.63 (d, 1H), 7.50-7.48 (m, 2H), 7.31 (s, 1H), 7.08 (s, 1H), 6.79 (s, 1H), 6.50-6.46 (d, 1H), 6.31 (m, 1H), 5.81-5.79 (d, 1H), 3.53 (s, 2H), 2.75 (m, 1H), 2.59 (m, 8H), 2.44 (s, 3H), 1.08 (s, 3H), 1.06 (s, 3H)

Example 55: Preparation of N-(3-(4-((4-methyl-1,4-diazepan-1-yl)methyl)-6-(5-methylthiazol-2-ylamino)pyridin-2-yl)phenyl)acrylamide

Step 55-1: Preparation of ethyl 2,6-dichloroisonicotinate

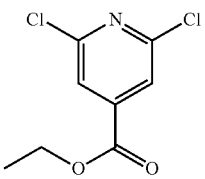

2,6-Dichloroisonicotinic acid (5.0 g, 26.0 mmol) was dissolved in ethanol (50 mL), cooled to 0° C., and then thionyl chloride (78.1 mL, 78.1 mmol, 1 M dichloromethane solution) was slowly added dropwise thereto. The reaction solution was stirred for 20 hours and concentrated under reduced pressure. The concentrated residue was dissolved in a small amount of dichloromethane, and water was slowly added dropwise, and then filtered under reduced pressure to give the title compound (3.5 g, yield: 61.1%).

Step 55-2: Preparation of ethyl 2-chloro-6-(3-nitrophenyl)isnicotinate

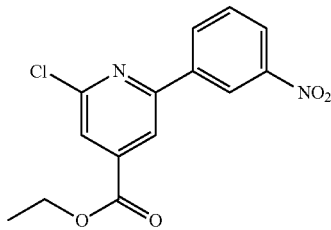 [SMILES: CCOC(=O)c1cc(Cl)nc(-c2cccc([N+](=O)[O-])c2)c1]

The intermediate (500.0 mg, 2.3 mmol) obtained in step 55-1, cesium carbonate (1.1 g, 3.4 mmol), and [1,1'-bis(diphenylphosphino)ferrocene]dichloropalladium(II) (166.3 mg, 0.02 mmol) were dissolved in 1,4-dioxane:$H_2O$ (6:1 solution, 10 mL), and then stirred for 10 minutes. 3-Nitrophenyl boronic acid (379.0 mg, 2.3 mmol) was slowly added dropwise to the reaction solution, and the mixture was stirred for 2 hours at room temperature. Water was added to the reaction solution, the organic layer was separated, treated with magnesium sulfate, filtered, and the filtrate was concentrated and purified by column chromatography (dichloromethane:n-hexane=1:10→dichloromethane:n-hexane=1:5) to give the title compound (292.0 mg, yield 41.9%).

Step 55-3: Preparation of ethyl 2-((5-methylthiazol-2-yl)amino)-6-(3-nitrophenyl)isonicotinate

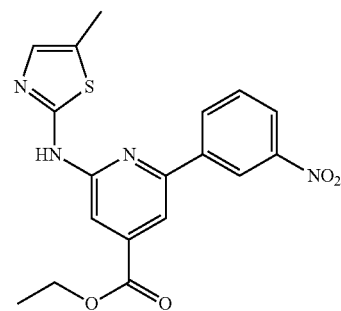 [SMILES: CCOC(=O)c1cc(Nc2ncc(C)s2)nc(-c2cccc([N+](=O)[O-])c2)c1]

The intermediate (140.0 mg, 0.5 mmol) obtained in step 55-2, palladium acetate (10.3 mg, 0.05 mmol), cesium carbonate (446.2 mg, 1.4 mmol), and 4,5-bis(diphenylphosphino)-9,9-dimethylxanthene (52.8 mg, 0.09 mmol) were dissolved in 1,4-dioxane (5 mL) and then stirred for 10 minutes. 2-Aminothiazole (52.1 mg, 0.5 mmol) was added dropwise to the reaction solution and reacted in a microwave reactor at 150° C. for 30 minutes. 5 mL of ethyl acetate was added dropwise to the reaction, and then water was added, stirred for 30 minutes, and filtered under reduced pressure to give the title compound (150 mg, yield: 88.9%).

Step 55-4: Preparation of 2-((5-methylthiazol-2-yl)amino)-6-(3-nitrophenyl)isonicotinic acid

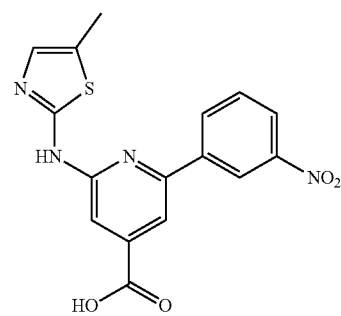 [SMILES: Cc1cnc(Nc2cc(C(=O)O)cc(-c3cccc([N+](=O)[O-])c3)n2)s1]

The intermediate (360.0 mg, 1.0 mmol) obtained in step 55-3 was dissolved in ethanol (3 mL), and then 1M sodium hydroxide aqueous solution (8 mL) was slowly added dropwise thereto. The reaction solution was stirred at 100° C. for 3 hours. After cooling the reaction solution to room temperature, water was added dropwise and filtered to give the title compound (189 mg, yield: 56.8%).

Step 55-5: Preparation of (4-methyl-1,4-diazepane-1-yl)(2-((5-methylthiazol-2-yl)amino)-6-(3-nitrophenyl)pyridine-4-yl)methanone

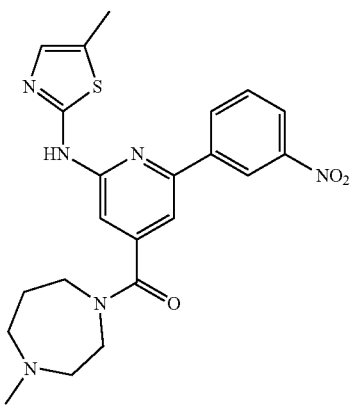 [SMILES: Cc1cnc(Nc2cc(C(=O)N3CCCN(C)CC3)cc(-c3cccc([N+](=O)[O-])c3)n2)s1]

The intermediate (180.0 mg, 0.5 mmol) obtained in step 55-4, 1-hydroxybenzothiazole (97.0 mg, 0.6 mmol), and 1-ethyl-3-(3-dimethylaminopropyl)carbodiimide hydrochloride (121.3 mg, 0.6 mmol) were dissolved in N,N-dimethylformamide (3 mL) and stirred for 30 minutes. 1-Methylhomopiperazine (68.9 uL, 0.6 mmol) was added dropwise and stirred at room temperature for 16 hours.

Water was added to the reaction solution, which was extracted with ethyl acetate. The organic layer was treated with sodium sulfate, then filtered and dried to give the title compound (180.0 mg, yield: 75.6%).

Step 55-6: Preparation of 5-methyl-N-(4-((4-methyl-1,4-diazepin-1-yl)methyl)-6-(3-nitrophenyl)pyridin-2-yl)thiazole-2-amine

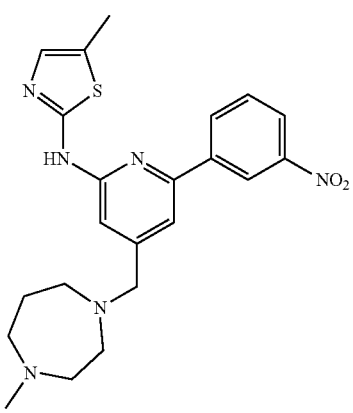 [SMILES: Cc1cnc(Nc2cc(CN3CCCN(C)CC3)cc(-c3cccc([N+](=O)[O-])c3)n2)s1]

The intermediate (170.0 mg, 0.4 mmol) obtained in step 56-5 was dissolved in dichloromethane (1 mL). After substitution with nitrogen atmosphere, borane (0.9 M tetrahydrofuran solution, 1.3 mL) was added dropwise at room temperature. The reaction solution was stirred at 50° C. for 16 hours. The reaction solution was cooled to 0° C., 4N hydrochloric acid aqueous solution (2 mL, 7.5 mmol) was slowly added dropwise and stirred at room temperature for 1 hour. The reaction solution was neutralized to pH 12 with 50 wt % sodium hydroxide aqueous solution, and extracted with dichloromethane. The organic layer was treated with sodium sulfate, filtered and then concentrated to give the title compound (120.0 mg, yield: 72.8%).

Step 55-7: Preparation of N-(6-(3-aminophenyl)-4-((4-methyl-1,4-diazepane-1-yl)methyl)pyridin-2-yl)-5-methylthiazole-2-amine

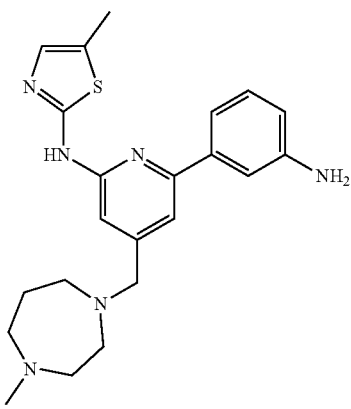 [SMILES: Cc1cnc(Nc2cc(CN3CCCN(C)CC3)cc(-c3cccc(N)c3)n2)s1]

The intermediate (100.0 mg, 0.2 mmol) obtained in step 55-6 was dissolved in methanol (1 mL), and 1M hydrochloric acid (ethyl acetate solution, 5 drops) was slowly added dropwise thereto, and the mixture was stirred under hydrogen atmosphere for 15 hours. The reaction solution was cooled to room temperature, filtered through celite, and then concentrated under reduced pressure to give the title compound (56.0 mg, yield: 93.2%).

Step 55-8: Preparation of N-(3-(4-((4-methyl-1,4-diazepan-1-yl)methyl)-6-(5-methylthiazol-2-yl)amino)pyridin-2-yl)phenyl)acrylamide

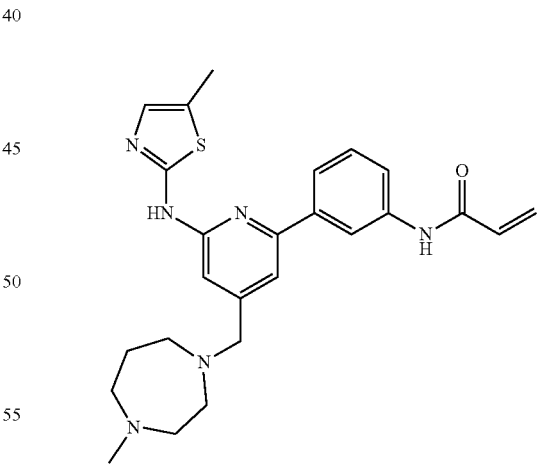

The intermediate (56.0 mg, 0.1 mmol) obtained in steps 55-7, sodium bicarbonate (23.0 mg, 0.3 mmol) were dissolved in a tetrahydrofuran:water mixed solution (2 mL: 0.3 mL), and acryloyl chloride (11.1 μL, 0.1 mmol) was slowly added dropwise thereto, and then the reaction solution was stirred at room temperature for 1 hour. Water was added to the reaction solution, which was extracted with ethyl acetate, and the organic layer was treated with magnesium sulfate, filtered, and then concentrated. The concentrated residue was purified by column chromatography (dichloromethane:methanol=10:1) to give the title compound (10.0 mg, yield: 15.8%).

1H NMR (500 MHz, CDCl₃): 10.05 (s, 1H), 8.38 (s, 1H), 7.83-7.59 (m, 2H), 7.40-7.32 (t, 1H), 7.02-6.82 (m, 3H), 6.55-6.52 (m, 2H), 6.43-6.40 (m, 1H), 5.71-5.83 (d, 2H), 3.77-3.79 (m, 4H), 3.58-3.35 (m, 4H), 2.75 (s, 2H), 2.60-2.48 (m, 2H) 2.40 (s, 3H), 2.01 (s, 3H).

Example 56: Preparation of N-(2-fluoro-5-(6-((5-methylthiazol-2-yl)amino)-4-(morpholinomethyl)pyridin-2-yl)phenyl)acrylamide

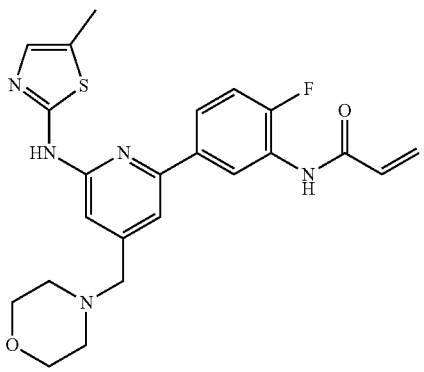 [SMILES: C=CC(=O)Nc1cc(-c2cc(CN3CCOCC3)cc(Nc3ncc(C)s3)n2)ccc1F]

The title compound (12.0 mg, yield: 35.0%) was obtained in the same manner as in Example 52, except that in step 52-1 of Example 52, (4-fluoro-3-nitrophenyl)boronic acid was used instead of (2-fluoro-5-nitrophenyl)boronic acid.

1H NMR (500 MHz, CDCl₃): 9.29 (d, 1H), 7.98-7.95 (m, 1H), 7.54 (s, 1H), 7.46 (s, 1H), 7.10 (s, 1H), 6.82 (s, 1H), 6.52-6.49 (d, 1H), 6.37-3.61 (m, 1H), 5.86-5.54 (d, 1H), 3.76 (m, 4H), 3.52 (s, 2H), 2.5 (m, 4H), 2.47 (s, 3H)

Example 57: Preparation of N-(3-fluoro-5-(6-((5-methylthiazol-2-yl)amino)-4-(morpholinomethyl)pyridin-2-yl)phenyl)acrylamide

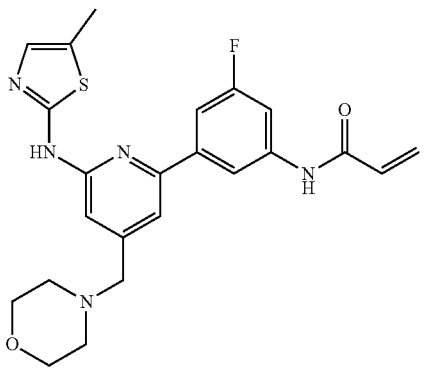 [SMILES: C=CC(=O)Nc1cc(F)cc(-c2cc(CN3CCOCC3)cc(Nc3ncc(C)s3)n2)c1]

The title compound (12.0 mg, yield 35.0%) was obtained in the same manner as in Example 52, except that in step 52-1 of Example 52, (3-fluoro-5-nitrophenyl)boronic acid was used instead of (2-fluoro-5-nitrophenyl)boronic acid.

1H NMR (500 MHz, CDCl₃): 8.15 (s, 1H), 7.80 (s, 1H), 7.55 (s, 1H), 7.53 (s, 1H), 7.10 (s, 1H), 6.85 (s, 1H), 6.51-6.47 (d, 1H), 6.32-6.42 (m, 1H), 5.84-5.82 (d, 1H), 3.74 (m, 4H), 3.84 (s, 2H), 2.49 (m, 4H), 2.44 (s, 3H)

Example 58: Preparation of N-(2-methyl-5-(6-((5-methylthiazol-2-yl)amino)-4-(morpholinomethyl)pyridin-2-yl)phenylacrylamide

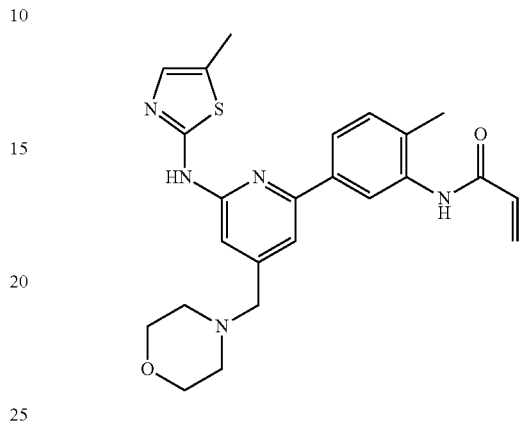

The title compound (20.0 mg, yield: 45.0%) was obtained in the same manner as in Example 52, except that in step 52-1 of Example 52, (4-methyl-3-nitrophenyl)boronic acid was used instead of (2-fluoro-5-nitrophenyl)boronic acid.

1H NMR (500 MHz, CDCl₃): 7.80 (s, 1H), 7.75 (s, 1H), 7.55 (s, 1H), 7.15 (s, 1H), 6.95 (s, 1H), 6.90 (s, 1H), 6.40 (d, 1H), 6.30 (m, 1H), 5.8 (d, 1H), 3.80 (m, 4H), 3.50 (s, 2H), 2.49 (m, 4H), 2.40 (s, 3H)

Example 59: Preparation of N-(4-methyl-3-(6-((5-methylthiazol-2-yl)amino)-4-(morpholinomethyl)pyridin-2-yl)phenyl)acrylamide

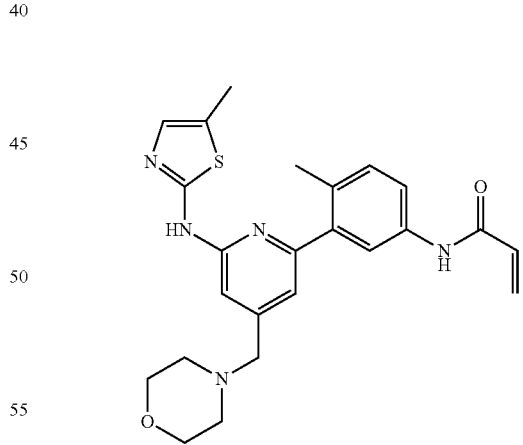

The title compound (15.0 mg, yield: 40.0%) was obtained in the same manner as in Example 52, except that in step 52-1 of Example 52, (2-methyl-3-nitrophenyl)boronic acid was used instead of (2-fluoro-5-nitrophenyl)boronic acid.

1H NMR (500 MHz, CDCl₃): 8.80 (s, 1H), 7.95 (d, 1H), 7.35 (d, 1H), 7.30 (s, 1H), 7.10 (s, 1H), 6.80 (s, 1H), 6.50 (d, 1H), 6.30-6.40 (m, 1H), 5.85 (d, 1H), 3.80-3.90 (m, 4H), 3.50 (s, 2H), 2.5 (m, 4H), 2.4-2.50 (s, 3H), 2.30-2.40 (s, 3H)

Example 60: Preparation of N-(3-(4-((4-acetylpiperazin-1-yl)methyl)-6-(5-methylthiazol-2-ylamino)pyridin-2-yl)phenyl)acrylamide Step 60-1: Preparation of tert-butyl 4-(2-((5-methylthiazol-2-yl)amino)-6-(3-nitrophenyl)isonicotinoyl)piperazine-1-carboxylate

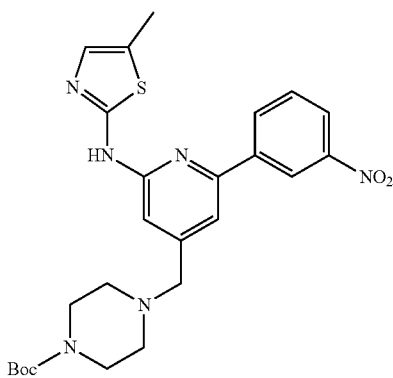 [SMILES: Cc1cnc(Nc2cc(CN3CCN(C(=O)OC(C)(C)C)CC3)cc(-c3cccc([N+](=O)[O-])c3)n2)s1]

The intermediate (2.8 g, 7.9 mmol) obtained in step 55-4, 1-hydroxybenzothiazole (1.4 g, 9.4 mmol), and 1-ethyl-3-(3-dimethylaminopropyl)carbodiimide hydrochloride (1.4 g, 9.4 mmol) were dissolved in N,N-dimethylformamide (20 mL) and stirred for 30 minutes. Tert-butylpiperazine-1-carboxylate (1.5 g, 8.3 mmol) was added dropwise thereto and stirred at room temperature for 16 hours. Water was added to the reaction solution and extracted with ethyl acetate. The organic layer was treated with sodium sulfate, filtered and dried to give the title compound (3.5 g, yield: 83.7%).

Step 60-2: Preparation of 1-(4-((2-((5-methylthiazol-2-yl)amino-6-(3-nitrophenyl)pyridin-4-yl)methyl)piperazin-1-yl)ethane-1-one

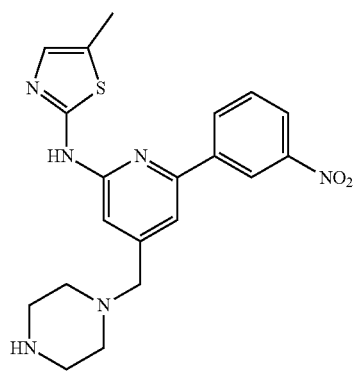 [SMILES: Cc1cnc(Nc2cc(CN3CCNCC3)cc(-c3cccc([N+](=O)[O-])c3)n2)s1]

The intermediate (3.4 g, 6.5 mmol) obtained in step 60-1 was dissolved in dichloromethane (15 mL). After substitution with nitrogen atmosphere, borane (0.9M tetrahydrofuran solution, 22 mL) was added dropwise at room temperature. The reaction solution was stirred at 50° C. for 16 hours. The reaction solution was cooled to 0° C., 4N hydrochloric acid aqueous solution (32.4 mL, 0.1 mol) was slowly added dropwise thereto and stirred at room temperature for 1 hour. The reaction solution was neutralized to pH 12 with 50 wt % sodium hydroxide aqueous solution, and extracted with dichloromethane. The organic layer was treated with sodium sulfate, filtered and then concentrated to give the title compound (1.94 g, yield: 72.8%).

Step 60-3: Preparation of 1-(4-((2-((5-methylthiazol-2-yl)amino-6-(3-nitrophenyl)pyridin-4-yl)methyl)piperazin-1-yl)ethane-1-one

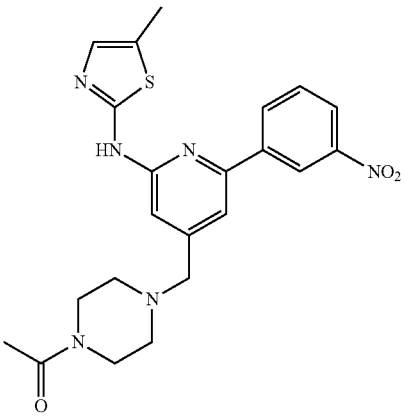 [SMILES: CC(=O)N1CCN(Cc2cc(Nc3ncc(C)s3)nc(-c3cccc([N+](=O)[O-])c3)c2)CC1]

After the intermediate (100.0 mg, 0.2 mmol) obtained in step 60-2 was dissolved in tetrahydrofuran (1 mL), triethylamine (51.0 µL, 0.4 mmol) and acetylchloride (17.4 µL, 0.2 mmol) were added dropwise sequentially and the mixture was stirred at room temperature for 30 minutes. The reaction solution was concentrated under reduced pressure, and then purified by column chromatography (ethyl acetate:methanol=15:1) to give the title compound (59.0 mg, yield: 55.3%).

Step 60-4: Preparation of 1-(4-((2-(3-aminophenyl)-6-((5-methylthiazol-2-yl)amino)pyridin-4-yl)methyl)piperazin-1-yl)ethan-1-one

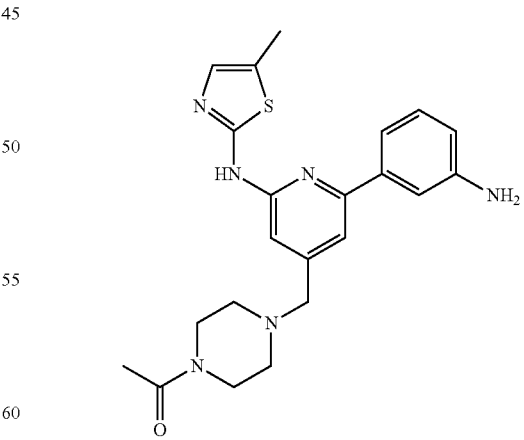

After the intermediate (59.0 mg, 0.1 mmol) obtained in step 60-3 was dissolved in methanol (2 mL), 1M hydrochloric acid (ethyl acetate solution, 5 drops) was slowly added dropwise thereto and stirred under hydrogen atmosphere for 15 hours. The reaction solution was cooled to room temperature, filtered through celite, and concentrated under reduced pressure to give the title compound (50.0 mg, yield: 90.9%).

Step 60-5: Preparation of N-(3-(4-((4-acetylpiperazin-1-yl)methyl)-6-((5-methylthiazol-2-yl)amino)pyridin-2-yl)phenyl)acrylamide

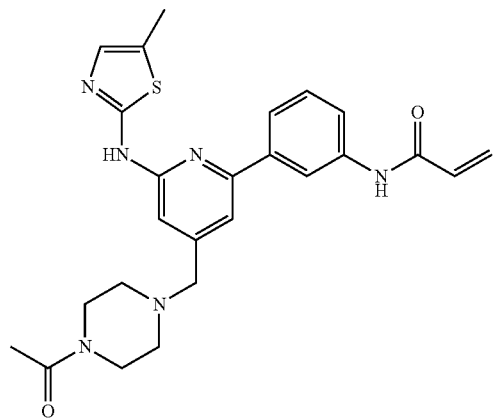 [SMILES: C=CC(=O)Nc1cccc(-c2cc(CN3CCN(C(C)=O)CC3)cc(Nc3ncc(C)s3)n2)c1]

After the intermediate (50.0 mg, 0.1 mmol) obtained in step 60-4 and sodium bicarbonate (20.6 mg, 0.2 mmol) were dissolved in a tetrahydrofuran:water mixed solution (2 mL: 0.3 mL), acryloyl chloride (10.0 uL, 0.1 mmol) was added slowly dropwise thereto, and then the reaction solution was stirred at room temperature for 1 hour. Water was added to the reaction solution, which was extracted with ethyl acetate, and the organic layer was treated with magnesium sulfate, filtered, and then concentrated. The concentrated residue was purified by column chromatography (dichloromethane: methanol=10:1) to give the title compound (14.8 mg, yield: 24.8%).

1H NMR (500 MHz, DMSO-$d_6$): 11.05 (s, 1H), 10.26 (s, 1H), 8.64 (s, 1H), 7.87 (d, 1H), 7.62 (d, 1H), 7.46 (t, 1H), 7.33 (s, 1H), 7.04 (s, 1H), 6.96 (s, 1H), 6.50-6.45 (m, 1H), 6.28 (d, 1H), 5.78-5.74 (m, 1H), 3.53 (s, 2H), 3.44 (brs, 4H), 3.27 (s, 3H), 2.41-2.34 (m, 4H), 1.97 (s, 3H), MS M/z: 477.33 [m+1].

Example 61: Preparation of N (3(6(5methylthiazol-2-ylamino)-4-((4-propionylpiperazin-1-yl)methyl) pyridin-2-yl)phenyl)acrylamide

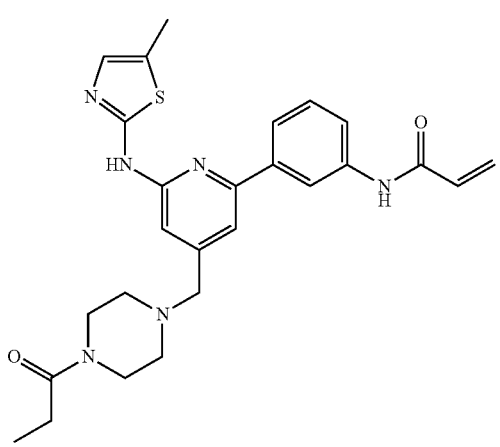 [SMILES: C=CC(=O)Nc1cccc(-c2cc(CN3CCN(C(=O)CC)CC3)cc(Nc3ncc(C)s3)n2)c1]

The title compound (total yield: 5.9%, 3 steps) was obtained in the same manner as in steps 60-3 to 60-5 of Example 60, except that in step 60-3 of Example 60, propionylchloride was used instead of acetylchloride.

1H NMR (500 MHz, DMSO-$d_6$): 11.05 (s, 1H), 10.26 (s, 1H), 8.65 (s, 1H), 7.87 (d, 1H), 7.62 (d, 1H), 7.48 (t, 1H), 7.33 (s, 1H), 7.18 (s, 1H), 7.04 (s, 1H), 6.96 (s, 1H), 6.50-6.45 (m, 1H), 6.28 (d, 1H), 5.78-5.76 (m, 1H), 5.32-5.30 (m, 2H), 3.44 (brs, 4H), 3.28 (s, 3H), 2.01-1.96 (m, 4H), 0.79-0.9 (m, 3H), MS M/z: 491.41 [m+1]

Example 62: Preparation of N (3(4((4-isobutyrylpiperazin-1-yl)methyl)-6-(5-methylthiazol-2-ylamino)pyridin-2-yl)phenyl)acrylamide

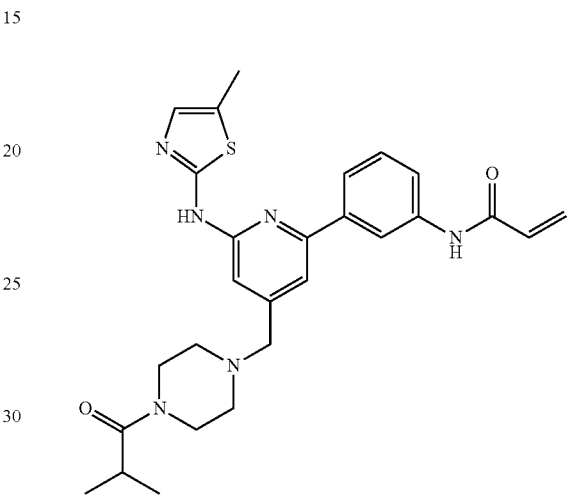

The title compound (total yield: 9.0%, 3 steps) was obtained in the same manner as in steps 60-3 to 60-5 of Example 60, except that in step 60-3 of Example 60, isobutyrylchloride was used instead of acetylchloride.

1H NMR (500 MHz, DMSO-$d_6$): 11.04 (s, 1H), 10.26 (s, 1H), 8.64 (s, 1H), 7.87 (d, 1H), 7.62 (d, 1H), 7.46 (t, 1H), 7.34 (s, 1H), 7.04 (s, 1H), 6.96 (s, 1H), 6.50-6.45 (m, 1H), 6.28 (d, 1H), 5.78-5.74 (m, 1H), 3.53-3.50 (m, 4H), 2.62 (s, 2H), 2.35 (s, 3H), 3.30 (s, 2H), 1.97-1.99 (m, 3H), 0.97-0.96 (m, 4H), MS M/z: 505.37 [m+1]

Example 63: Preparation of N (3(4((4-(cyclopropanecarbonyl)piperazin-1-yl)methyl)-6-(5-methylthiazol-2-ylamino)pyridin-2-yl) phenyl)acrylamide

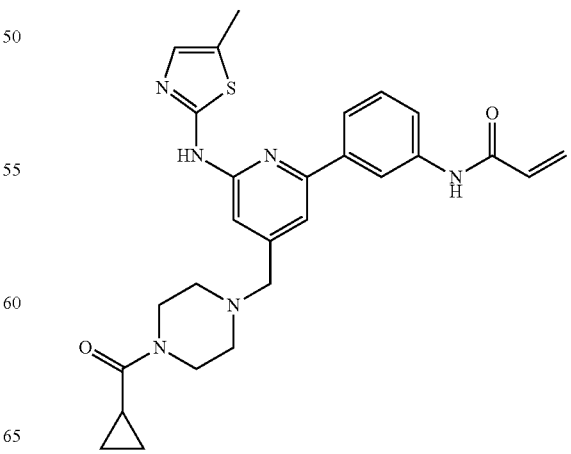

The title compound (total yield 12.1%, 3 steps) was obtained in the same manner as in steps 60-3 to 60-5 of Example 60, except that in step 60-3 of Example 60, cyclopropanecarbonyl chloride was used instead of acetylchloride.

Example 64: Preparation of N-(4-chloro-3-(6-((5-methylthiazol-2-yl)amino)-4-(morpholinomethyl) pyridin-2-yl)phenylacrylamide

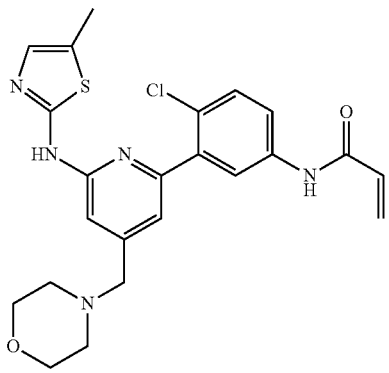 [SMILES: C=CC(=O)Nc1ccc(Cl)c(-c2cc(CN3CCOCC3)cc(Nc3ncc(C)s3)n2)c1]

The title compound (10.0 mg, yield: 42.0%) was obtained in the same manner as in Example 52, except that in step 52-1 of Example 52, (2-chloro-3-nitrophenyl)boronic acid was used instead of (2-fluoro-5-nitrophenyl)boronic acid.

1H NMR (500 MHz, DMSO): 10.18 (s, 1H), 9.22 (s, 1H), 8.07 (s, 1H), 9.82 (d, 1H), 7.71 (d, 1H), 7.19 (s, 1H), 6.53-6.48 (m, 2H), 6.25 (s, 1H), 6.09 (d, 1H), 5.74 (d, 1H), 4.44 (s, 2H), 3.57 (m, 4H), 2.42 (m, 4H), 2.30 (s, 3H)

Example 65: Preparation of N-methyl-N-(3-(6-((5-methylthiazol-2-yl)amino)-4-(morpholinomethyl) pyridin-2-yl)phenylacrylamide

Step 65-1: Preparation of t-butyl (3-(6-chloro-4-(morpholinomethyl)pyridin-2-yl)phenyl)carbamate

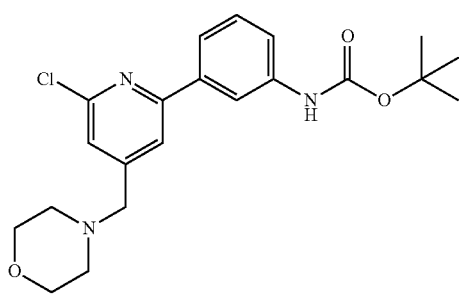 [SMILES: CC(C)(C)OC(=O)Nc1cccc(-c2cc(CN3CCOCC3)cc(Cl)n2)c1]

The title compound (450.0 mg, yield: 35.0%) was obtained in the same manner as in step 22-3 of Example 22, except that in step 22-3 of Example 22, 3-((1-t-butoxy) carbonyl)amino)phenyl)boronic acid was used instead of 3-nitrophenyl boronic acid.

Step 65-2: Preparation of t-butyl (3-(6-((-5-methylthiazol-2-yl)amino)-4-(morpholinomethyl) pyridin-2-yl)phenyl)carbamate

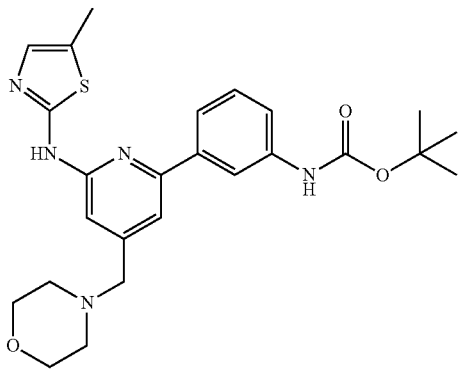 [SMILES: Cc1cnc(Nc2cc(CN3CCOCC3)cc(-c3cccc(NC(=O)OC(C)(C)C)c3)n2)s1]

The title compound (348.8 mg, yield 60.0%) was obtained in the same manner as in Example 30, except that in step 30-1 of Example 30, the intermediate obtained in step 65-1 was used instead of the intermediate obtained in step 22-3.

Step 65-3: Preparation of t-butyl methyl(3-(6-(5-methylthiazol-2-yl)amino)-4-(morpholinomethyl) pyridin-2-yl)phenyl)carbamate

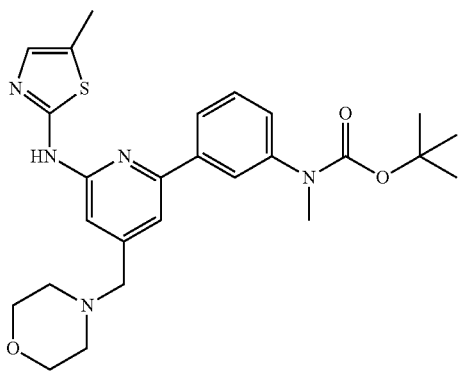 [SMILES: Cc1cnc(Nc2cc(CN3CCOCC3)cc(-c3cccc(N(C)C(=O)OC(C)(C)C)c3)n2)s1]

The intermediate (340.0 mg, 1 eq) obtained in step 65-2 was dissolved in tetrahydrofuran (3.4 mL), and then, under nitrogen, sodium hydride (56.5 mg, 2 eq) was added and methyl iodide (100.2 mg, 1 eq) was added. The mixture was stirred at 40~50° C. for 12 hours to complete the reaction. After adding ethyl acetate (7.0 mL) and water (7.0 mL), the ethyl acetate layer was dried over anhydrous sodium sulfate and then concentrated under reduced pressure. The resulting residue was purified by column chromatography (ethyl acetate:hexane=1:1) to give the title compound (235.9 mg, yield: 74.0%).

Step 65-4: Preparation of 5-methyl-N-(6-(3-methyl-amino)phenyl)-4-(morpholinomethyl)pyridin-2-yl)thiazol-2-amine

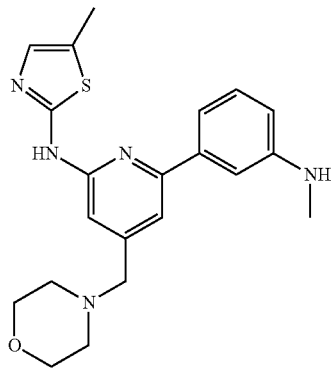 [SMILES: CNc1cccc(-c2cc(CN3CCOCC3)cc(Nc3ncc(C)s3)n2)c1]

The intermediate (200.0 mg, 1 eq) obtained in step 65-3 was dissolved in tetrahydrofuran (2.0 mL). 6N hydrochloric acid aqueous solution (670.2 uL, 10 eq) was added and then the mixture was stirred at room temperature for 6 hours to complete the reaction. After adjusting the pH to 9~12 with 12N sodium hydroxide aqueous solution, the organic solvent was concentrated to give the title compound (95.8 mg, yield: 60.0%) as a solid.

Step 65-5: Preparation of N-methyl-N-(3-(6-((5-methylthiazol-2-yl)amino)-4-(morpholinomethyl)pyridin-2-yl)phenyl)acrylamide

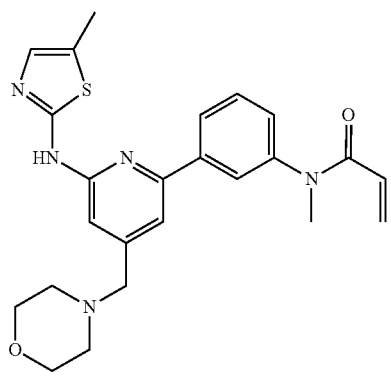

The intermediate (90.0 mg, 1 eq) obtained in step 65-4 was added to tetrahydrofuran (1.0 mL) and water (2.0 mL) was added. Sodium bicarbonate (57.5 mg, 3 eq) was added and then cooled to 0~10° C. Acryloyl chloride (18.5 uL, 1 eq) was slowly added dropwise thereto, and then the mixture was stirred at the same temperature for 30 minutes to complete the reaction. Dichloromethane (2.0 mL) and water (2.0 mL) were added and the layers separated. The dichloromethane layer was dried over anhydrous sodium sulfate and then concentrated under reduced pressure. The resulting residue was purified by column chromatography (dichloromethane:methanol=15:1) to give the title compound (51.3 mg, yield: 50.0%).

1H NMR (500 MHz, DMSO): 8.14 (s, 1H), 8.13-8.12 (d, 1H), 7.61-7.58 (t, 1H), 7.44 (s, 1H), 7.38-7.36 (d, 1H), 7.04 (s, 1H), 6.99 (s, 1H), 6.18-6.19 (m, 2H), 5.60-5.58 (d, 1H), 3.6-6.7 (m, 4H), 3.50 (s, 3H), 2.40 (m, 4H), 2.3 (s, 3H), 1.21 (s, 3H)

Example 66: Preparation of N-ethyl-N-(3-(6-(5-methylthiazol-2-ylamino)-4-(morpholinomethyl)pyridin-2-yl)phenyl)acrylamide

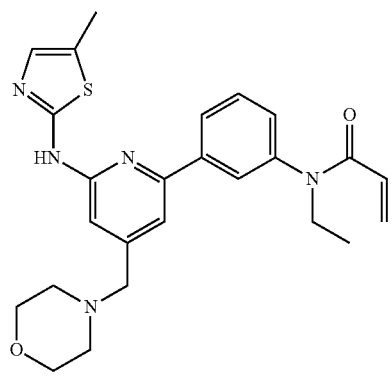 [SMILES: C=CC(=O)N(CC)c1cccc(-c2cc(CN3CCOCC3)cc(Nc3ncc(C)s3)n2)c1]

The title compound (18.0 mg, yield: 65.0%) was obtained in the same manner as in Example 65, except that in step 65-3 of Example 65, ethyl iodide was used instead of methyl iodide.

1H NMR (500 MHz, DMSO): 8.12 (s, 1H), 8.11-8.10 (d, 1H), 7.62-7.59 (t, 1H), 7.44 (s, 1H), 7.35-7.33 (d, 1H), 7.04 (s, 1H), 6.99 (s, 1H), 6.19 (d, 1H), 6.04 (m, 1H), 5.56-5.54 (d, 1H), 3.81-3.79 (q, 2H), 3.60-3.58 (m, 4H), 3.50 (s, 2H), 2.40 (m, 4H), 2.28 (s, 3H), 1.10 (t, 3H)

Example 67: Preparation of N-(3-(6-(3-methylureido)-4-(morpholinomethyl)pyridin-2-yl)phenyl)acrylamide

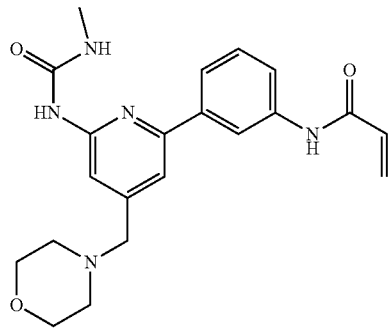 [SMILES: C=CC(=O)Nc1cccc(-c2cc(CN3CCOCC3)cc(NC(=O)NC)n2)c1]

The title compound (8.0 mg, yield: 50.0%) was obtained in the same manner as in Example 30, except that in step 30-1 of Example 30, 1-methylurea was used instead of 5-methylthiazol-2-amine.

1H NMR (500 MHz, DMSO): 8.44 (s, 1H), 7.63-7.61 (d, 1H), 7.59-7.57 (d, 1H), 7.44-7.41 (t, 1H), 7.34 (s, 1H), 7.27 (s, 1H), 6.48-6.44 (t, 1H), 6.29-6.25 (d, 1H), 5.78-5.75 (d, 1H), 3.59-3.57 (m, 4H), 3.48 (s, 2H), 2.79-2.78 (m, 4H), 2.38 (s, 3H)

Example 68: Preparation of N-(3-(4-(morpholinomethyl)-6-propionamidopyridin-2-yl)phenyl)acrylamide

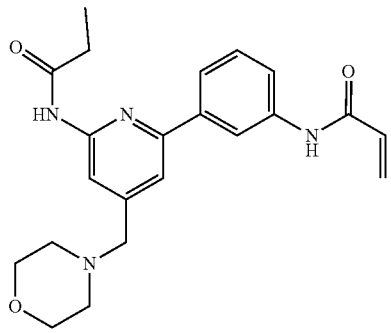 [SMILES: C=CC(=O)Nc1cccc(-c2cc(CN3CCOCC3)cc(NC(=O)CC)n2)c1]

The title compound (6.0 mg, yield: 11%) was obtained in the same manner as in Example 39, except that in step 39-3 of Example 39, propionamide was used instead of 5-methyl-1,3,4-thiadiazol-2-amine.

1H NMR (500 MHz, MeOD): 8.40 (s, 1H), 8.09 (s, 1H), 7.80 (d, 1H), 7.59 (m, 2H), 7.42 (t, 1H), 6.47 (m, 1H), 6.38 (d, 1H), 5.79 (d, 1H), 3.72 (m, 4H), 3.58 (s, 2H), 2.51-2.43 (m, 6H), 1.23 (t, 3H)

Example 69: Preparation of 4-((2-(3-acrylamidophenyl)-6-((5-methylthiazol-2-yl)amino)pyridin-4-yl)methyl)-N-ethylpiperazine-1-carboxamide Step 69-1: Preparation of t-butyl 2-chloro-6-(3-nitrophenyl)isonicotinate

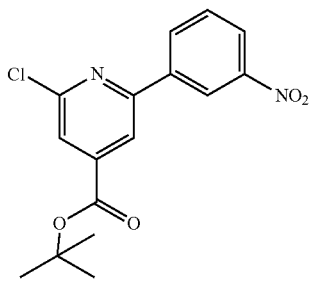 [SMILES: CC(C)(C)OC(=O)c1cc(Cl)nc(-c2cccc([N+](=O)[O-])c2)c1]

After t-butyl 2,6-dichloroisonicotinate (15.0 g, 1.0 eq) was dissolved in 1,4-dioxane (200.0 mL), (3-nitrophenyl)boronic acid (10.1 g, 1.0 eq), sodium carbonate (25.6 g, 4.0 eq), water (50.0 mL), and tetrakis(triphenylphosphine)palladium(0) (7.0 g, 0.1 eq) were added sequentially. The mixture was reacted at 110° C. for 8 hours. Water was added and the mixture was extracted with dichloromethane. The separated organic layer was dried over anhydrous sodium sulfate and then concentrated under reduced pressure. The resulting residue was slurried with ethyl acetate, filtered and the filtrate was collected and concentrated under reduced pressure. The resulting residue was purified by column chromatography (ethyl acetate:hexane=1:4) to give the title compound (white solid, 7.3 g, yield: 36%).

Step 69-2: Preparation of t-butyl 2-((5-methylthiazol-2-yl)amino)-6-(3-nitrophenyl) isonicotinate

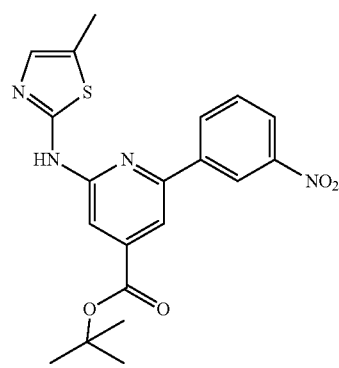 [SMILES: Cc1cnc(Nc2cc(C(=O)OC(C)(C)C)cc(-c3cccc([N+](=O)[O-])c3)n2)s1]

After the intermediate (1.0 g, 1.0 eq) obtained in step 69-1 was dissolved in 1,4-dioxane (10.0 mL), cesium carbonate (2.9 g, 3.0 eq), palladium acetate (67.4 mg, 0.1 eq), Xantphos (549.4 mg, 0.2 eq), and 5-methylthiazol-2-amine (341.1 mg, 1.0 eq) were added sequentially. The mixture was reacted in a microwave reactor at 150° C. for 30 minutes. Water and ethyl acetate were added and then filtered to give the title compound (yellow solid, 768.6 mg, yield: 62%).

Step 69-3: Preparation of 2-(3-nitrophenyl)-6-(thiazol-2-ylamino)isonicotinic acid

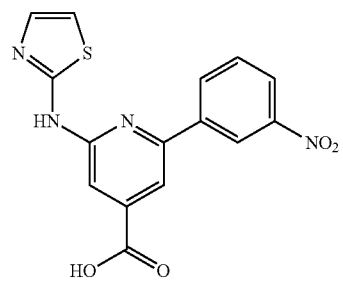 [SMILES: O=C(O)c1cc(Nc2nccs2)nc(-c2cccc([N+](=O)[O-])c2)c1]

After the intermediate (5.4 g, 1.0 eq) obtained in step 69-2 was dissolved in dichloromethane (100.0 mL), trifluoroacetic acid (20.0 mL, 20.0 eq) was added dropwise and the mixture was reacted at room temperature for 6 hours. A saturated sodium bicarbonate solution was added until crystals formed, and filtered to give the title compound (yellow solid, 4.8 g, yield: 99%).

Step 69-4: Preparation of t-butyl 4-(2-((5-methylthiazol-2-yl)amino)-6-(3-nitrophenyl)isonicotinoyl)piperazine-1-carboxylate

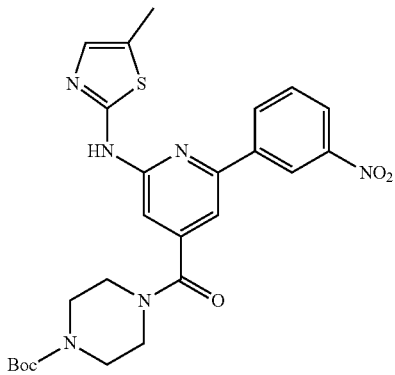 [SMILES: Cc1cnc(Nc2cc(C(=O)N3CCN(C(=O)OC(C)(C)C)CC3)cc(-c3cccc([N+](=O)[O-])c3)n2)s1]

After the intermediate (5.45 g, 1.0 eq) obtained in step 69-3 was dissolved in dimethylformamide (50.0 mL), 2-(1H-benzotriazol-1-yl)-1,1,3,3-tetramethyluronium hexafluorophosphate) (8.7 g, 1.5 eq), diisopropylamine (5.9 g, 3.0 eq), t-butyl piperazine-1-carboxylate (3.4 g, 1.2 eq) were added sequentially. The mixture was reacted at room temperature for 12 hours. Water was added and the mixture was extracted with dichloromethane. The separated organic layer was dried over anhydrous sodium sulfate and then concentrated under reduced pressure. The resulting residue was slurried with ethyl acetate and then filtered to give the title compound (yellow solid, 5.3 g, yield: 66%).

Step 69-5: Preparation of 5-methyl-N-(6-(3-nitrophenyl)-4-(piperazin-1-ylmethyl)pyridin-2-yl)thiazol-2-amine

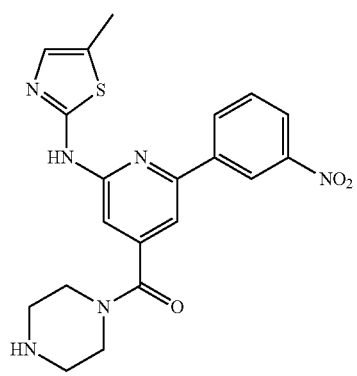 [SMILES: Cc1cnc(Nc2cc(C(=O)N3CCNCC3)cc(-c3cccc([N+](=O)[O-])c3)n2)s1]

After the intermediate (5.3 g, 1.0 eq) obtained in step 69-4 was dissolved in dichloromethane (200.0 mL), 0.9 M borane tetrahydrofuran solution (45.0 mL, 4.0 eq) was added. The mixture was reacted at room temperature for 48 hours. Water was added and the mixture was extracted with dichloromethane. The separated organic layer was dried over anhydrous sodium sulfate and then concentrated under reduced pressure. The resulting residue was slurried with dichloromethane and then filtered to give the title compound (yellow solid, 2.1 g, yield: 51%).

Step 69-6: Preparation of N-ethyl-4-((2-((5-methylthiazol-2-yl)amino)-6-(3-nitrophenyl)pyridin-4-yl)methyl)piperazin-1-carboxamide

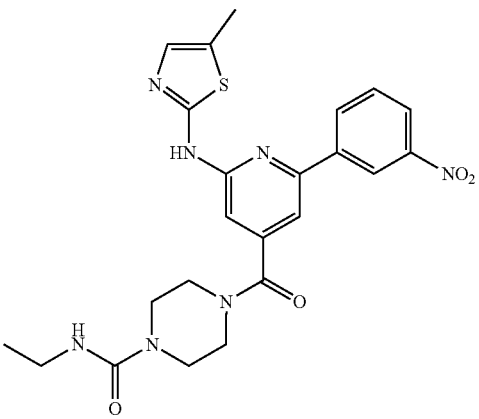 [SMILES: CCNC(=O)N1CCN(C(=O)c2cc(Nc3ncc(C)s3)nc(-c3cccc([N+](=O)[O-])c3)c2)CC1]

After the intermediate (100.0 mg, 1.0 eq) obtained in step 69-5 was dissolved in dimethylformamide (5.0 mL), triethylamine (50.9 μL, 1.5 eq), isocyanatoethane (13.6 μL, 1.1 eq) was added sequentially. The mixture was reacted at 30° C. for 12 hours. Water was added and the mixture was extracted with dichloromethane. The separated organic layer was dried over anhydrous sodium sulfate and then concentrated under reduced pressure. The resulting residue was slurried with dichloromethane, then filtered, slurried once more with methanol and then filtered to give the title compound (yellow solid, 33.0 mg, yield: 29%).

Step 69-7: Preparation of 4-((2-(3-aminophenyl)-6-((5-methylthiazol-2-yl)amino)pyridin-4-yl)methyl)-N-ethylpiperazine-1-carboxamide The intermediate (33.0 mg, 1.0 eq) obtained in step 69-6 was dissolved in methanol (10.0 mL) and then reacted for 6 hours at room temperature in the presence of a palladium carbon and a hydrogen gas. The mixture was filtered through celite and then concentrated under reduced pressure. The resulting residue was purified by column chromatography (dichloromethane:methanol=9:1) to obtain the title compound (white solid, 18.6 mg, yield: 60%).

Step 69-8: Preparation of 4-((2-(3-acrylamidophe-nyl)-6-((5-methylthiazol-2-yl)amino)pyridin-4-yl)methyl)-N-ethylpiperazine-1-carboxamide

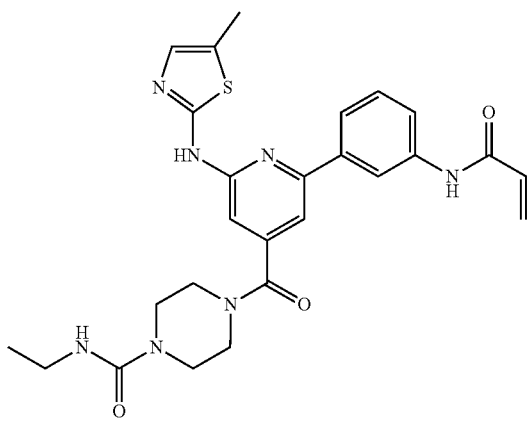 [SMILES: C=CC(=O)Nc1cccc(-c2cc(C(=O)N3CCN(C(=O)NCC)CC3)cc(Nc3ncc(C)s3)n2)c1]

After the intermediate (18.6 mg, 1.0 eq) obtained in step 69-7 was dissolved in tetrahydrofuran (2.0 mL), sodium bicarbonate (6.9 mg, 2.0 eq), water (0.5 mL) and acryloyl chloride (3.4 μL, 1.0 eq) were added sequentially. The mixture was reacted at room temperature for 30 minutes. Water was added and the mixture was extracted with ethyl acetate. The separated organic layer was dried over anhydrous sodium sulfate and then concentrated under reduced pressure. The resulting residue was slurried with dichloromethane and then filtered to obtain the title compound (white solid, 8.8 mg, yield: 43%).

1H NMR (500 MHz, DMSO): 11.05 (s, 1H), 10.27 (s, 1H), 8.64 (s, 1H), 7.87 (d, 1H), 7.63 (d, 1H), 7.46 (t, 1H), 7.32 (s, 1H), 7.04 (s, 1H), 6.96 (s, 1H), 6.46 (m, 1H), 6.28 (d, 1H), 5.76 (d, 1H), 3.51 (s, 2H), 3.29 (m, 4H), 3.00 (m, 2H), 2.35 (m, 4H), 0.98 (t, 3H)

Example 70: Preparation of 4-((2-(3-acrylamidophenyl)-6-((5-methylthiazol-2-yl)amino)pyridin-4-yl)methyl)-N-isopropylpiperazine-1-carboxamide

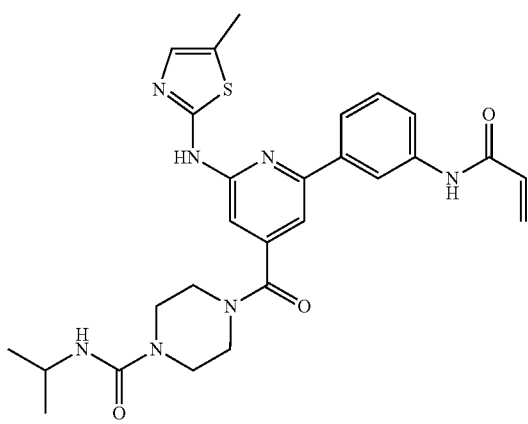 [SMILES: C=CC(=O)Nc1cccc(-c2cc(C(=O)N3CCN(C(=O)NC(C)C)CC3)cc(Nc3ncc(C)s3)n2)c1]

The title compound (9.2 mg, yield: 42%) was obtained in the same manner as in Example 69, except that in step 69-6 of Example 69, 2-isocyanatopropane was used instead of isocyanatoethane.

1H NMR (500 MHz, DMSO): 11.06 (s, 1H), 10.27 (s, 1H), 8.64 (s, 1H), 7.87 (d, 1H), 7.63 (d, 1H), 7.46 (t, 1H), 7.32 (s, 1H), 7.04 (s, 1H), 6.96 (s, 1H), 6.47 (m, 1H), 6.28 (d, 1H), 6.13 (d, 1H), 5.77 (d, 1H), 3.72 (m, 1H), 3.51 (s, 2H), 3.29 (m, 4H), 2.35 (m, 6H), 1.01 (d, 6H)

Example 71: Preparation of 4-((2-(3-acrylamidophenyl)-6-((5-methylthiazol-2-yl)amino)pyridin-4-yl)methyl)-N-methylpiperazine-1-carboxamide

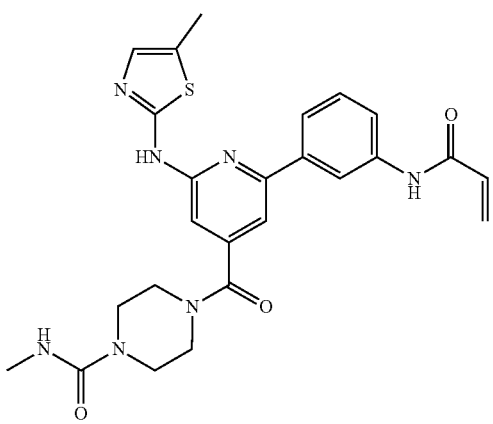 [SMILES: C=CC(=O)Nc1cccc(-c2cc(C(=O)N3CCN(C(=O)NC)CC3)cc(Nc3ncc(C)s3)n2)c1]

The title compound (4.8 mg, yield: 21%) was obtained in the same manner as in Example 69, except that in step 69-6 of Example 69, isocyanatomethane was used instead of isocyanatoethane.

1H NMR (500 MHz, DMSO): 11.04 (s, 1H), 10.26 (s, 1H), 8.64 (s, 1H), 7.87 (d, 1H), 7.63 (d, 1H), 7.46 (t, 1H), 7.32 (s, 1H), 7.04 (s, 1H), 6.96 (s, 1H), 6.47 (m, 1H), 6.30 (m, 1H), 6.27 (d, 1H), 5.77 (d, 1H), 3.51 (s, 2H), 2.54 (m, 4H), 2.36 (m, 6H)

Example 72: Preparation of N-(3-(6-((5-methyl-1H-pyrazol-3-yl)amino)-4-(pyridin-3-ylmethyl)pyridin-2-yl)phenyl)acrylamide Step 72-1: Preparation of 2,6-dichloro-4-(pyridin-3-ylmethyl)pyridine

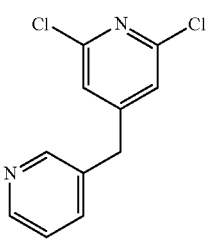

After (2,6-dichloropyridin-4-yl)boronic acid (1.0 g, 1.0 eq) was dissolved in 1,4-dioxane (80.0 mL), 3-(bromomethyl)pyridine hydrobromide (1.3 g, 1.0 eq), sodium carbonate (1.7 g, 3.0 eq), water (20.0 mL), and [1,1'-bis(diphenylphosphino)ferrocene]dichloropalladium(II) (381.2 mg, 0.1 eq) were added sequentially. The mixture was reacted at 80° C. for 3 hours. Water was added and the mixture was extracted with dichloromethane. The separated organic layer was dried over anhydrous sodium sulfate and then concentrated under reduced pressure. The resulting residue was purified by column chromatography (ethyl acetate:hexane=1:1) to give the title compound (brown solid, 416.7 mg, yield: 34%).

Step 72-2: Preparation of N-(3-(6-chloro-4-(pyridin-3-ylmethyl)pyridin-2-yl)phenyl)acrylamide

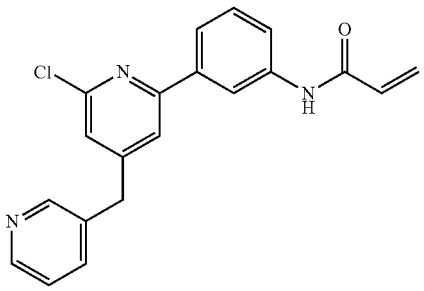 [SMILES: C=CC(=O)Nc1cccc(-c2cc(Cc3cccnc3)cc(Cl)n2)c1]

After the intermediate (416.7 mg, 1.0 eq) obtained in step 72-1 was dissolved in 1,4-dioxane (10.0 mL), sodium carbonate (737.7 mg, 4.0 eq), water (2.0 mL), tetrakis(triphenylphosphine)palladium(0) (208.0 mg, 0.1 eq), and (3-acrylamidophenyl)boronic acid (332.9 mg, 1.0 eq) were added sequentially. The mixture was reacted at 120° C. for 3 hours. Water was added and the mixture was extracted with dichloromethane. The separated organic layer was dried over anhydrous sodium sulfate and then concentrated under reduced pressure. The resulting residue was slurried with dichloromethane and then filtered to give the title compound (white solid, 104.1 mg, yield: 17%).

Step 72-3: Preparation of N-(3-(6-((5-methyl-1H-pyrazol-3-yl)amino)-4-(pyridin-3-ylmethyl)pyridin-2-yl)phenyl)acrylamide

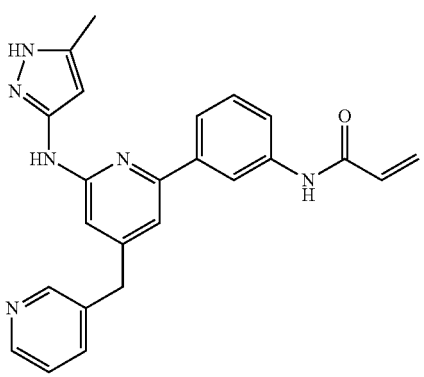 [SMILES: C=CC(=O)Nc1cccc(-c2cc(Cc3cccnc3)cc(Nc3cc(C)[nH]n3)n2)c1]

After the intermediate (50.0 mg, 1.0 eq) obtained in step 72-2 was dissolved in 1,4-dioxane (4.0 mL), sodium carbonate (44.5 mg, 3.0 eq), tris(dibenzylideneacetone)dipalladium(0) (64.1 mg, 0.5 eq), Xantphos (40.5 mg, 0.5 eq), and t-butyl 3-amino-5-methyl-1H-pyrazole-1-carboxylate (41.4 mg, 2.0 eq) were added sequentially. The mixture was reacted in a microwave reactor at 140° C. for 2 hours. Water was added and the mixture was extracted with dichloromethane. The separated organic layer was dried over anhydrous sodium sulfate and then concentrated under reduced pressure. The resulting residue was purified by column chromatography (dichloromethane:methanol=9:1), dissolved in dichloromethane (10.0 mL), and then trifluoroacetic acid (1.0 mL) was added dropwise, and the mixture was reacted at room temperature for 12 hours. Water was added and the mixture was extracted with dichloromethane. The separated organic layer was dried over anhydrous sodium sulfate and then concentrated under reduced pressure. The resulting residue was purified by column chromatography (dichloromethane:methanol=9:1) to give the title compound (brown solid, 1.9 mg, yield: 4%).

1H NMR (500 MHz, MeOD): 8.51 (s, 1H), 8.41 (d, 1H), 8.31 (s, 1H), 7.76 (d, 1H), 7.70 (d, 1H), 7.63 (d, 1H), 7.43-7.38 (m, 2H), 7.12 (s, 1H), 6.76 (s, 1H), 6.46 (m, 1H), 6.38 (d, 1H), 5.78 (d, 1H), 4.03 (s, 2H), 2.27 (s, 3H)

Example 73: Preparation of N-(3-(6-((5-methylthiazol-2-yl)amino)-4-(pyridin-3-ylmethyl)pyridin-2-yl)phenyl)acrylamide

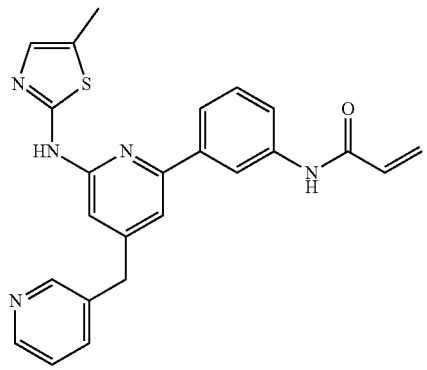 [SMILES: C=CC(=O)Nc1cccc(-c2cc(Cc3cccnc3)cc(Nc3ncc(C)s3)n2)c1]

The title compound (8.6 mg, yield: 23%) was obtained in the same manner as in Example 72, except that in step 72-3 of Example 72, 5-methylthiazol-2-amine was used instead of t-butyl 3-amino-5-methyl-1H-pyrazole-1-carboxylate.

1H NMR (500 MHz, MeOD): 8.63 (s, 1H), 8.51 (s, 1H), 8.41 (s, 1H), 7.90 (d, 1H), 7.75 (d, 1H), 7.53 (d, 1H), 7.46-7.38 (m, 2H), 7.29 (s, 1H), 6.96 (s, 1H), 6.69 (s, 1H), 6.46 (m, 1H), 6.38 (d, 1H), 5.78 (d, 1H), 4.05 (s, 2H), 2.39 (s, 3H)

Experimental Example: Inhibitory Activity Against BTK and ITK

Inhibitory activities against BTK and ITK were measured for the compounds prepared in the above Examples as follows.

The inhibitory activities against BTK were evaluated using 'ADP-Glo™+BTK Kinase enzyme system' kit (Promega Corporation). In a white 96-well plate, 10 ul of BTK enzyme prepared so as to have a final concentration of 1 ng/ul was mixed with 5 μl of compounds having a final concentration of 1 ul in the case of evaluating a single concentration of compound and a concentration of 1000, 300, 100, 30, 10, 3, 1, 0.3, 0.1 and 0.03 nM in the case of IC50 evaluation, and then reacted at room temperature for 15 minutes. 5 ul of substrate and 5 ul of ATP prepared so as to have a final concentration of 10 μM were added to the plate on which reactions were completed, and then allowed to react at 30° C. for 1 hour. All wells of the plate were treated with 25 ul of ADP-Glo™ reagent and allowed to react at 30° C. for 40 minutes. After that, all wells were treated with 50 ul of kinase detection buffer, and then reacted at 30° C. for 30 minutes under light shielding conditions. For the plate on which all reactions were completed, luminescence was measured and the results were calculated. Evaluation was carried out in duplicate, and negative control and positive control were calculated depending on whether or not the enzyme was added without treatment of the compound. The $IC_{50}$ was calculated based on the calculated values.

The inhibitory activity against ITK was evaluated using 'ADP-Glo™+ITK Kinase enzyme system' kit (Promega Corporation). In a white 96-well plate, 10 ul of ITK enzyme prepared so as to have a final concentration of 0.4 ng/ul was mixed with 5 ul of compounds having a final concentration of 1 uM in the case of evaluating a single concentration of compound and a concentration of 1000, 300, 100, 30, 10, 3, 1, 0.3, 0.1 and 0.03 nM in the case of $IC_{50}$ evaluation, and then reacted at room temperature for 15 minutes. To the plate on which reactions were completed, 5 ul of substrate and 5 ul of ATP prepared so as to have a final concentration of 25 ul were added and then allowed to react at 30° C. for 1 hour. All wells of the plate were treated with 25 ul of ADP-Glo™ reagent and then allowed to react at 30° C. for 40 minutes. After that, all wells were treated with 50 ul of kinase detection buffer, and then allowed to react at 30° C. for 30 minutes under light shielding conditions. For the plate on which all reactions were completed, luminescence was measured and the results were calculated. Evaluation was carried out in duplicate, and negative control and positive control were calculated depending on whether or not the enzyme was added without treatment of the compound. The $IC_{50}$ was calculated based on the calculated values.

TABLE 1

| Compound No. | Inhibitory activity | |
|---|---|---|
| | ITK $IC_{50}$ (nM) | BTK $IC_{50}$ (nM) |
| 1 | 289.3 | >1000 |
| 2 | 88.2 | 24.1 |
| 3 | 23.5 | 45.9 |
| 4 | 91.4 | 634.0 |
| 5 | 316.6 | 777.3 |
| 6 | >500 | >1000 |
| 7 | >500 | 123.4 |
| 8 | 572.5 | 308.2 |
| 9 | >1000 | >1000 |
| 10 | 501.8 | 65.1 |
| 11 | 134.0 | 17.5 |
| 12 | 995.2 | 7.8 |
| 13 | 266.2 | 138.2 |
| 14 | 399.4 | 349.8 |
| 15 | >500 | 18.0 |
| 16 | 192.0 | 6.1 |
| 17 | 131.3 | 11.1 |
| 18 | >1000 | 28.7 |
| 19 | >500 | 74.7 |
| 20 | 253.8 | 28.1 |
| 21 | >500 | 52.6 |
| 22 | 77.8 | 6.1 |
| 23 | 128.3 | 13.1 |
| 24 | 159.1 | 10.9 |
| 25 | 59.3 | 8.6 |
| 26 | 76.4 | 10.5 |
| 27 | 36.9 | 68.7 |
| 28 | 68.1 | 310.3 |
| 29 | 18.6 | 5.2 |
| 30 | 4.3 | 3.1 |
| 31 | 56.9 | 17.6 |
| 32 | 25.7 | 20.3 |
| 33 | >1000 | 1.9 |
| 34 | 3.1 | 2.4 |

TABLE 1-continued

| Compound No. | Inhibitory activity | |
|---|---|---|
| | ITK $IC_{50}$ (nM) | BTK $IC_{50}$ (nM) |
| 35 | >1000 | >400 |
| 36 | 394.2 | >100 |
| 37 | 5.5 | 0.9 |
| 38 | 535.5 | >400 |
| 39 | >1000 | 252.4 |
| 40 | >1000 | >400 |
| 41 | >1000 | >400 |
| 42 | >1000 | >400 |
| 43 | 2.1 | 2.3 |
| 44 | 12.0 | 2.0 |
| 45 | 2.1 | 3.0 |
| 46 | 1.6 | 1.7 |
| 47 | 8.2 | 3.0 |
| 48 | 4.3 | 1.1 |
| 49 | 3.1 | 1.3 |
| 50 | 5.0 | 2.2 |
| 51 | 2.2 | 5.2 |
| 52 | 2.2 | 1.9 |
| 53 | 3.8 | 2.3 |
| 54 | 2.9 | 1.9 |
| 55 | 13.4 | 10.6 |
| 56 | 4.2 | 1.8 |
| 57 | 23.2 | >6.3 |
| 58 | 14.1 | 6.4 |
| 59 | 18.1 | 8.3 |
| 60 | 2.2 | 1.9 |
| 61 | 13.5 | 9.5 |
| 62 | 8.1 | 6.3 |
| 63 | 9.0 | 6.7 |
| 64 | 15.7 | 18.1 |
| 65 | 2.1 | 1.9 |
| 66 | 3.7 | 1.3 |
| 67 | >200 | 64.1 |
| 68 | >1000 | >400 |
| 69 | 6.7 | 2.6 |
| 70 | 6.0 | 3.1 |
| 71 | 2.0 | 0.9 |
| 72 | 8.0 | 3.3 |
| 73 | 2.3 | 2.5 |

The invention claimed is:

1. A compound represented by the following Chemical Formula 1, or a pharmaceutically acceptable salt thereof:

[Chemical Formula 1]

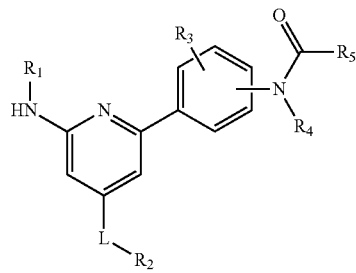

wherein, in Chemical Formula 1,
$R_1$ is —CO—($C_{1-4}$ alkyl); —CO—($C_{3-6}$ cycloalkyl); —CONH—($C_{1-4}$ alkyl); or 5- or 6-membered heteroaryl including 1 to 3 heteroatoms each independently selected from the group consisting of N, O and S, with the proviso that the 5- or 6-membered heteroaryl contains at least one N,
the 5- or 6-membered heteroaryl is unsubstituted or substituted with $C_{1-4}$ alkyl, $C_{1-4}$ haloalkyl, $C_{3-6}$ cycloalkyl, phenyl, phenoxyphenyl, —($C_{1-4}$ alkylene)-(phenyl unsubstituted or substituted with $C_{1-4}$ alkyl), or —CONH-(phenyl unsubstituted or substituted with $C_{1-4}$ alkyl and/or halogen), L is a bond, $C_{1-4}$ alkylene, or —CO—, $R_2$ is hydrogen; $C_{1-4}$ alkyl; $C_{1-4}$ haloalkyl; amino; NH($C_{1-10}$ alkyl); N($C_{1-10}$ alkyl)$_2$; phenyl; pyridinyl; or heterocycloalkyl selected from the group consisting of diazefanyl, morpholino, piperazinyl, piperidinyl, and pyrrolidinyl, the heterocycloalkyl is unsubstituted or substituted with $C_{1-4}$ alkyl, two $C_{1-4}$ alkyl, $C_{1-4}$ haloalkyl, $C_{3-6}$ cycloalkyl, $C_{1-4}$ alkyl substituted with $C_{1-4}$ alkoxy, $C_{1-4}$ hydroxyalkyl, —CO—($C_{1-4}$ alkyl), —CO—($C_{3-6}$ cycloalkyl), or —CONH—($C_{1-4}$ alkyl), $R_3$ is hydrogen, $C_{1-4}$ alkyl, or halogen, $R_4$ is hydrogen, or $C_{1-4}$ alkyl, and $R_5$ is $C_{2-4}$ alkenyl, or $C_{2-4}$ alkynyl.

2. The compound or a pharmaceutically acceptable salt thereof according to claim 1, wherein the 5- or 6-membered heteroaryl of $R_1$ is isoxazolyl, oxadiazolyl, pyrazolyl, pyridinyl, thiadiazolyl, or thiazolyl.

3. The compound or a pharmaceutically acceptable salt thereof according to claim 1, wherein the $R_1$ is —CO-(ethyl); —CO-(cyclopropyl); —CONH-(methyl); isoxazolyl substituted with methyl; oxadiazolyl substituted with methyl; pyrazolyl unsubstituted or substituted with methyl, ethyl, cyclopropyl, cyclopentyl, phenyl, phenoxyphenyl, methylbenzyl, 1-(methylphenyl)ethyl, or phenethyl; unsubstituted pyridinyl; thiadiazolyl unsubstituted or substituted with methyl; or thiazolyl substituted with methyl, trifluoromethyl, or —CONH— (phenyl substituted with methyl and chloro).

4. The compound or a pharmaceutically acceptable salt thereof according to claim 1, wherein L is a bond, methylene, or —CO—.

5. The compound or a pharmaceutically acceptable salt thereof according to claim 1, wherein $R_2$ is hydrogen; methyl; trifluoromethyl; dimethylamino; 3,3-dimethylbutan-2-ylamino; phenyl; pyridinyl; diazefanyl substituted with methyl; morpholino unsubstituted or substituted with two methyls; piperazinyl substituted with methyl, ethyl, propyl, isopropyl, 2,2,2-trifluoroethyl, cyclopropyl, 2-methoxyethyl, 2-hydroxyethyl, —CO-(methyl), —CO-(ethyl)-, —CO-(isopropyl), —CO-(cyclopropyl), —CONH-(methyl), —CONH-(ethyl)-, or —CO-(isopropyl); unsubstituted piperidinyl; or unsubstituted pyrrolodinyl.

6. The compound or a pharmaceutically acceptable salt thereof according to claim 1, wherein $R_3$ is hydrogen, methyl, fluoro, or chloro.

7. The compound or a pharmaceutically acceptable salt thereof according to claim 1, wherein $R_4$ is hydrogen, methyl, or ethyl.

8. The compound or a pharmaceutically acceptable salt thereof according to claim 1, wherein $R_5$ is —CH=CH$_2$, —CH=CHCH$_3$, or —C≡CH.

9. The compound or a pharmaceutically acceptable salt thereof according to claim 1, wherein Chemical Formula 1 is represented by the following Formula 1-1:

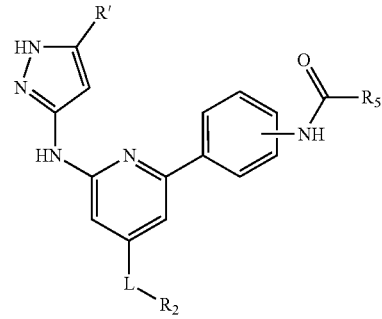

[Chemical Formula 1-1]

wherein, in Chemical Formula 1-1,

R' is hydrogen, $C_{1-4}$ alkyl, $C_{3-6}$ cycloalkyl, phenyl, phenoxyphenyl, —($C_{1-4}$ alkylene)-(phenyl unsubstituted or substituted with $C_{1-4}$ alkyl), or —CONH-(phenyl unsubstituted or substituted with $C_{1-4}$ alkyl and/or halogen), L is a bond, $C_{1-4}$ alkylene, or —CO—, $R_2$ is hydrogen; $C_{1-4}$ alkyl; $C_{1-4}$ haloalkyl; amino; NH($C_{1-10}$ alkyl); N($C_{1-10}$ alkyl)$_2$;

phenyl; pyridinyl; morpholino; or piperidinyl, and $R_5$ is $C_{2-4}$ alkenyl, or $C_{2-4}$ alkynyl.

10. The compound or a pharmaceutically acceptable salt thereof according to claim 1, wherein Chemical Formula 1 is represented by the following Chemical Formula 1-2:

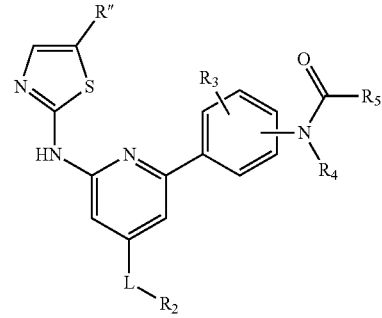

[Chemical Formula 1-2]

wherein, in Chemical Formula 1-2,

R" is $C_{1-4}$ alkyl, $C_{1-4}$ haloalkyl, or —CONH-(phenyl unsubstituted or substituted with $C_{1-4}$ alkyl and/or halogen), L is a bond, $C_{1-4}$ alkylene, or —CO—, $R_2$ is $C_{1-4}$ alkyl; amino; NH($C_{1-10}$ alkyl); N($C_{1-10}$ alkyl)$_2$; pyridinyl; or heterocycloalkyl selected from the group consisting of diazefanyl, morpholino, piperazinyl, and pyrrolodinyl, the heterocycloalkyl is unsubstituted or substituted with $C_{1-4}$ alkyl, two $C_{1-4}$ alkyls, $C_{1-4}$ haloalkyl, $C_{3-6}$ cycloalkyl, $C_{1-4}$ alkyl substituted with $C_{1-4}$ alkoxy, $C_{1-4}$ hydroxyalkyl, —CO—($C_{1-4}$ alkyl), —CO—($C_{3-6}$ cycloalkyl), or —CONH—($C_{1-4}$ alkyl), $R_3$ is hydrogen, $C_{1-4}$ alkyl, or halogen, $R_4$ is hydrogen or $C_{1-4}$ alkyl, and $R_5$ is $C_{2-4}$ alkenyl, or $C_{2-4}$ alkynyl.

11. The compound or a pharmaceutically acceptable salt thereof according to claim 1, wherein the compound represented by Chemical Formula 1 is any one selected from the group consisting of the following:

1) N-(4-(4-benzyl-6-(5-methyl-1H-pyrazol-3-ylamino)pyridin-2-yl)phenyl)acrylamide,
2) N-(3-(4-benzyl-6-(5-methyl-1H-pyrazol-3-ylamino)pyridin-2-yl)phenyl)acrylamide,
3) N-(4-(4-benzyl-6-(5-methyl-1H-pyrazol-3-ylamino)pyridin-2-yl)phenyl)propiolamide,
4) N-(3-(4-benzyl-6-(5-cyclopentyl-1H-pyrazol-3-ylamino)pyridin-2-yl)phenyl)acrylamide,
5) N-(3-(4-benzyl-6-(5-phenyl-1H-pyrazol-3-ylamino)pyridin-2-yl)phenyl)acrylamide,
6) N-(3-(4-benzyl-6-(5-methyl-1H-pyrazol-3-ylamino)pyridin-2-yl)phenyl)propiolamide,
7) N-(3-(4-benzyl-6-(5-(4-phenoxyphenyl)-1H-pyrazol-3-ylamino)pyridin-2-yl)phenyl)acrylamide,
8) N-(3-(4-benzyl-6-(5-(4-methylbenzyl)-1H-pyrazol-3-ylamino)pyridin-2-yl)phenyl)acrylamide,
9) N-(3-(4-benzyl-6-((5-(1-p-tolylethyl)-1H-pyrazol-3-yl)amino)pyridin-2-yl)phenyl)acrylamide,
10) N-(3-(4-benzyl-6-(5-phenethyl-1H-pyrazol-3-ylamino)pyridin-2-yl)phenyl)acrylamide,
11) N-(3-(6-(1H-pyrazol-3-ylamino)-4-benzylpyridin-2-yl)phenyl)acrylamide,
12) N-(3-(6-(5-methyl-1H-pyrazol-3-ylamino)pyridin-2-yl)phenyl)acrylamide,
13) N-(3-(6-(5-cyclopentyl-1H-pyrazol-3-ylamino)pyridin-2-yl)phenyl)acrylamide,
14) N-(3-(6-(5-phenyl-1H-pyrazol-3-ylamino)pyridin-2-yl)phenyl)acrylamide,
15) N-(3-(6-(1H-pyrazol-3-ylamino)pyridin-2-yl)phenyl)acrylamide,
16) N-(3-(4-methyl-6-(5-methyl-1H-pyrazol-3-ylamino)pyridin-2-yl)phenyl)acrylamide,
17) N-(3-(6-(5-methyl-1H-pyrazol-3-ylamino)-4-(trifluoromethyl)pyridin-2-yl)phenyl)acrylamide,
18) N-(3-(4-methyl-6-(pyridin-2-ylamino)pyridin-2-yl)phenyl)acrylamide,
19) N-(3-(4-((3,3-dimethylbutan-2-ylamino)methyl)-6-(5-methyl-1H-pyrazol-3-ylamino)pyridin-2-yl)phenyl)acrylamide,
20) 2-(3-acrylamidophenyl)-N-(3,3-dimethylbutan-2-yl)-6-(5-methyl-1H-pyrazol-3-ylamino)isonicotinamide,
21) 2-(3-acrylamidophenyl)-N,N-dimethyl-6-(5-methyl-1H-pyrazol-3-ylamino)isonicotinamide,
22) N-(3-(6-(5-methyl-1H-pyrazol-3-ylamino)-4-(morpholinomethyl)pyridin-2-yl)phenyl)acrylamide,
23) N-(3-(6-(5-methyl-1H-pyrazol-3-ylamino)-4-phenylpyridin-2-yl)phenyl)acrylamide,
24) N-(3-(6-(5-ethyl-1H-pyrazol-3-ylamino)-4-methylpyridin-2-yl)phenyl)acrylamide,
25) N-(3-(6-(5-cyclopropyl-1H-pyrazol-3-ylamino)-4-methylpyridin-2-yl)phenyl)acrylamide,
26) N-(3-(4-methyl-6-(5-methylthiazol-2-ylamino)pyridin-2-yl)phenyl)acrylamide,
27) N-(3-(6-(5-cyclopropyl-1H-pyrazol-3-ylamino)-4-(morpholinomethyl)pyridin-2-yl)phenyl)acrylamide,
28) N-(3-(6-(5-cyclopropyl-1H-pyrazol-3-ylamino)-4-(morpholine-4-carbonyl)pyridin-2-yl)phenyl)acrylamide,
29) N-(3-(6-(5-methylthiazol-2-ylamino)-4-(morpholine-4-carbonyl)pyridin-2-yl)phenyl)acrylamide,
30) N-(3-(6-(5-methylthiazol-2-ylamino)-4-(morpholinomethyl)pyridin-2-yl)phenyl)acrylamide,
31) N-(3-(6-(5-methyl-1H-pyrazol-3-ylamino)-4-(morpholine-4-carbonyl)pyridin-2-yl)phenyl)acrylamide,
32) N-(3-(6-(5-methyl-1H-pyrazol-3-ylamino)-4-(piperidin-1-ylmethyl)pyridin-2-yl)phenyl)acrylamide,
33) 2-(6-(3-acrylamidophenyl)-4-(morpholinomethyl)pyridin-2-ylamino)-N-(2-chloro-6-methylphenyl)thiazole-5-carboxamide,
34) N-(3-(4-((2,6-dimethylmorpholino)methyl)-6-(5-methylthiazol-2-ylamino)pyridin-2-yl)phenyl)acrylamide,
35) N-(3-(4-(dimethylamino)-6-(5-methylthiazol-2-ylamino)pyridin-2-yl)phenyl)acrylamide,
36) N-(3-(6-(5-methylthiazol-2-ylamino)-4-morpholinopyridin-2-yl)phenyl)acrylamide,
37) N-(3-(4-((4-methylpiperazin-1-yl)methyl)-6-(5-methylthiazol-2-ylamino)pyridin-2-yl)phenyl)acrylamide,
38) (E)-N-(3-(4-benzyl-6-(5-methyl-1H-pyrazol-3-ylamino)pyridin-2-yl)phenyl)but-2-enamide,
39) N-(3-(6-(5-methyl-1,3,4-thiadiazol-2-ylamino)-4-(morpholinomethyl)pyridin-2-yl)phenyl)acrylamide,
40) N-(3-(6-(5-methylisoxazol-3-ylamino)-4-(morpholinomethyl)pyridin-2-yl)phenyl)acrylamide,
41) N-(3-(6-(5-methyl-1,3,4-oxadiazol-2-ylamino)-4-(morpholinomethyl)pyridin-2-yl)phenyl)acrylamide,
42) N-(6-(3-acrylamidophenyl)-4-(morpholinomethyl)pyridin-2-yl)cyclopropanecarboxamide,
43) N-(3-(4-((4-(2-hydroxyethyl)piperazin-1-yl)methyl)-6-(5-methylthiazol-2-ylamino)pyridin-2-yl)phenyl)acrylamide,
44) N-(3-(6-(1,2,4-thiadiazol-5-ylamino)-4-(morpholinomethyl)pyridin-2-yl)phenyl)acrylamide,
45) N-(3-(4-((4-cyclopropylpiperazin-1-yl)methyl)-6-(5-methylthiazol-2-ylamino)pyridin-2-yl)phenyl)acrylamide,
46) N-(3-(4-(((2S,6R)-2,6-dimethylmorpholino)methyl)-6-(5-methylthiazol-2-ylamino)pyridin-2-yl)phenyl)acrylamide,
47) N-(3-(6-(5-methylthiazol-2-ylamino)-4-(pyrrolidin-1-ylmethyl)pyridin-2-yl)phenyl)acrylamide,
48) N-(3-(6-(5-methylthiazol-2-ylamino)-4-((4-propylpiperazin-1-yl)methyl)pyridin-2-yl)phenyl)acrylamide,
49) N-(3-(4-((4-(2-methoxyethyl)piperazin-1-yl)methyl)-6-(5-methylthiazol-2-ylamino)pyridin-2-yl)phenyl)acrylamide,
50) N-(3-(6-(5-methylthiazol-2-ylamino)-4-((4-(2,2,2-trifluoroethyl)piperazin-1-yl)methyl)pyridin-2-yl)phenyl)acrylamide,
51) N-(3-(4-(morpholinomethyl)-6-(5-(trifluoromethyl)thiazol-2-ylamino)pyridin-2-yl)phenyl)acrylamide,
52) N-(4-fluoro-3-(6-(5-methylthiazol-2-ylamino)-4-(morpholinomethyl)pyridin-2-yl)phenyl)acrylamide,
53) N-(3-(4-((4-ethylpiperazin-1-yl)methyl)-6-(5-methylthiazol-2-ylamino)pyridin-2-yl)phenyl)acrylamide,
54) N-(3-(4-((4-isopropylpiperazin-1-yl)methyl)-6-(5-methylthiazol-2-ylamino)pyridin-2-yl)phenyl)acrylamide,
55) N-(3-(4-((4-methyl-1,4-diazepan-1-yl)methyl)-6-(5-methylthiazol-2-ylamino)pyridin-2-yl)phenyl)acrylamide,
56) N-(2-fluoro-5-(6-(5-methylthiazol-2-ylamino)-4-(morpholinomethyl)pyridin-2-yl)phenyl)acrylamide,
57) N-(3-fluoro-5-(6-(5-methylthiazol-2-ylamino)-4-(morpholinomethyl)pyridin-2-yl)phenyl)acrylamide,
58) N-(2-methyl-5-(6-(5-methylthiazol-2-ylamino)-4-(morpholinomethyl)pyridin-2-yl)phenyl)acrylamide,
59) N-(4-methyl-3-(6-(5-methylthiazol-2-ylamino)-4-(morpholinomethyl)pyridin-2-yl)phenyl)acrylamide, 60) N-(3-(4-((4-acetylpiperazin-1-yl)methyl)-6-(5-methylthiazol-2-ylamino)pyridin-2-yl)phenyl)acrylamide,
61) N-(3-(6-(5-methylthiazol-2-ylamino)-4-((4-propionylpiperazin-1-yl)methyl)pyridin-2-yl)phenyl)acrylamide,
62) N-(3-(4-((4-isobutyrylpiperazin-1-yl)methyl)-6-(5-methylthiazol-2-ylamino)pyridin-2-yl)phenyl)acrylamide,
63) N-(3-(4-((4-(cyclopropanecarbonyl)piperazin-1-yl)methyl)-6-(5-methylthiazol-2-ylamino)pyridin-2-yl)phenyl)acrylamide,
64) N-(4-chloro-3-(6-(5-methylthiazol-2-ylamino)-4-(morpholinomethyl)pyridin-2-yl)phenyl)acrylamide,
65) N-methyl-N-(3-(6-(5-methylthiazol-2-ylamino)-4-(morpholinomethyl)pyridin-2-yl)phenyl)acrylamide,
66) N-ethyl-N-(3-(6-(5-methylthiazol-2-ylamino)-4-(morpholinomethyl)pyridin-2-yl)phenyl)acrylamide,
67) N-(3-(6-(3-methylureido)-4-(morpholinomethyl)pyridin-2-yl)phenyl)acrylamide,
68) N-(3-(4-(morpholinomethyl)-6-propionamidopyridin-2-yl)phenyl)acrylamide,
69) 4-((2-(3-acrylamidophenyl)-6-(5-methylthiazol-2-ylamino)pyridin-4-yl)methyl)-N-ethylpiperazine-1-carboxamide,
70) 4-((2-(3-acrylamidophenyl)-6-(5-methylthiazol-2-ylamino)pyridin-4-yl)methyl)-N-isopropylpiperazine-1-carboxamide,
71) 4-((2-(3-acrylamidophenyl)-6-(5-methylthiazol-2-ylamino)pyridin-4-yl)methyl)-N-methylpiperazine-1-carboxamide,
72) N-(3-(6-(5-methyl-1H-pyrazol-3-ylamino)-4-(pyridin-3-ylmethyl)pyridin-2-yl)phenyl)acrylamide, and
73) N-(3-(6-(5-methylthiazol-2-ylamino)-4-(pyridin-3-ylmethyl)pyridin-2-yl)phenyl)acrylamide.

12. A pharmaceutical composition comprising the compound according to claim 1 or a pharmaceutically acceptable salt thereof as an active ingredient.

13. A method of treating B-cell cancers or inhibiting Bruton's Tyrosine Kinase (BTK) and Interleukin-2 Tyrosine Kinase (ITK), comprising administering to a subject in need thereof an effective amount of the compound according to claim 1 or a pharmaceutically acceptable salt thereof.

* * * * *